United States Patent
Gray et al.

(10) Patent No.: US 11,248,007 B2
(45) Date of Patent: Feb. 15, 2022

(54) INHIBITORS OF MALT1 AND USES THEREOF

(71) Applicants: Cornell University, Ithaca, NY (US); Dana-Farber Cancer Institute, Inc., Boston, MA (US)

(72) Inventors: Nathanael S. Gray, Boston, MA (US); David A. Scott, Newton, MA (US); John Hatcher, Marlborough, MA (US); Ari M. Melnick, New York, NY (US); Lorena Fontan Gabas, New York, NY (US)

(73) Assignees: Cornell University, Ithaca, NY (US); Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 16/492,066

(22) PCT Filed: Mar. 8, 2018

(86) PCT No.: PCT/US2018/021481
§ 371 (c)(1),
(2) Date: Sep. 6, 2019

(87) PCT Pub. No.: WO2018/165385
PCT Pub. Date: Sep. 13, 2018

(65) Prior Publication Data
US 2020/0385405 A1    Dec. 10, 2020

Related U.S. Application Data

(60) Provisional application No. 62/553,336, filed on Sep. 1, 2017, provisional application No. 62/468,758, filed on Mar. 8, 2017.

(51) Int. Cl.
*C07D 513/04* (2006.01)
*C07D 401/12* (2006.01)
*C07D 401/14* (2006.01)
*C07D 405/14* (2006.01)
*C07D 417/14* (2006.01)

(52) U.S. Cl.
CPC ......... *C07D 513/04* (2013.01); *C07D 401/12* (2013.01); *C07D 401/14* (2013.01); *C07D 405/14* (2013.01); *C07D 417/14* (2013.01)

(58) Field of Classification Search
CPC .. C07D 513/04; C07D 401/12; C07D 401/14; C07D 405/14; C07D 417/14
USPC .................................................. 514/210.21
See application file for complete search history.

(56) References Cited

U.S. PATENT DOCUMENTS

| 5,596,001 A | 1/1997 | Hamanaka |
| 9,090,592 B2 * | 7/2015 | Turner ............... A61P 25/28 |
| 2015/0297570 A1 | 10/2015 | Melnick et al. |

FOREIGN PATENT DOCUMENTS

| GB | 2504550 | 2/2014 | |
| WO | WO-2012089828 A2 * | 7/2012 | ........... C07D 471/04 |
| WO | WO 2014/074815 A1 | 5/2014 | |
| WO | WO 2014/086478 A1 | 6/2014 | |
| WO | WO 2015/181747 A1 | 12/2015 | |
| WO | WO 2018/020474 A1 | 2/2018 | |
| WO | WO 2018/085247 A1 | 5/2018 | |

OTHER PUBLICATIONS

Extended European Search Report for EP 18763780.6, dated Sep. 9, 2020.
Li et al., Automatic tailoring and transplanting: a practical method that makes virtual screening more useful. J Chem Inf Model. Jun. 27, 2011;51(6):1474-91. doi: 10.1021/ci200036m. Epub May 13, 2011. PMID: 21520918.
PCT/US2018/021481, Apr. 13, 2018, Invitation to Pay Additional Fees.
PCT/US2018/021481, Jun. 6, 2018, International Search Report and Written Opinion.
PCT/US2018/021481, Sep. 19, 2019, International Preliminary Report on Patentability.
International Preliminary Report on Patentability dated Sep. 19, 2019 for Application No. PCT/US2018/021481.
International Search Report and Written Opinion dated Jun. 6, 2018 for International Application No. PCT/US2018/021481.
Invitation to Pay Additional Fees dated Apr. 13, 2018 for International Application No. PCT/US2018/021481.

* cited by examiner

*Primary Examiner* — Kahsay Habte
(74) *Attorney, Agent, or Firm* — Wolf, Greenfield & Sacks, P.C.

(57) ABSTRACT

Provided herein are compounds that inhibit MALT1, a protein whose activity is responsible for constitutive NF-κB signaling in certain cancers (e.g., activated B-cell diffuse large B-cell lymphoma (ABC-DLBCL)). Also provided are pharmaceutical compositions and kits comprising the compounds, and methods of treating MALT1-related diseases and disorders (e.g., cancer) with the compounds in a subject, by administering the compounds and/or compositions described herein.

20 Claims, No Drawings

INHIBITORS OF MALT1 AND USES THEREOF

RELATED APPLICATIONS

This application is a national stage filing under 35 U.S.C. § 371 of international application PCT/US2018/021481, filed Mar. 8, 2018, which claims priority under 35 U.S.C. § 119(e) to U.S. Provisional Patent Application, U.S. Ser. No. 62/468,758, filed Mar. 8, 2017, and U.S. Provisional Patent Application, U.S. Ser. No. 62/553,336, filed Sep. 1, 2017. The entirety of each is incorporated herein by reference.

FIELD OF THE INVENTION

The present invention relates generally to compounds that inhibit MALT1 and uses of the compounds in the treatment of MALT1-related diseases or disorders (e.g., cancer).

BACKGROUND OF THE INVENTION

Diffuse large B-cell lymphoma (DLBCL) is a cancer of B cells and is the most common type of non-Hodgkin's lymphoma in adults. DLBCL is an aggressive tumor which can arise in almost any part of the body. Typically, DLBCL arises from normal B cells, but it can also represent a malignant transformation of other types of lymphoma or leukemia with underlying immunodeficiency being a significant risk factor. Despite advances in treatment, one third of DLBCL patients either do not respond or relapse within a short time. There are two major biologically distinct molecular subtypes of DLBCL: germinal center B-cell (GCB) and activated B-cell (ABC). ABC-DLBCL is derived from B cells that are in the process of differentiating from germinal center B cells to plasma cells. Typically, patients diagnosed with the ABC subtype have poorer outcomes than GCB patients.

Mucosa-associated lymphoid tissue lymphoma translocation protein 1 (MALT1) is part of the paracaspase family and possesses proteolytic activity. It is a functional cysteine protease activated by T-cell receptor stimulation that has an important role in the activation of the transcription factor NF-κB, in the production of interleukin-2 (IL-2), and in the proliferation of T and B lymphocytes. For example, the survival of several known ABC-DLBCL cell lines depends on a trio of signaling adapters: CARD11, MALT1, and BCL10. These proteins form the CBM complex that is involved in the antigen-dependent activation of NF-κB. In addition to acting as a scaffold protein within the CBM complex, MALT1 also contains a proteolytic activity that is constitutively activated in ABC-DLBCL. MALT1 inhibitors are known to inhibit NF-κB target gene expression and ABC-DLBCL viability, making MALT1 inhibition an attractive therapeutic target for the treatment of ABC-DLBCL. In addition, dysregulation of MALT1 activity plays a role in the development of other diseases, such as MALT1-dependent inflammatory and/or autoimmune diseases (e.g., rheumatoid arthritis, multiple sclerosis, psoriasis, systemic lupus, Sjögren's syndrome, and Hashimoto's thyroiditis). Accordingly, a need exists to discover and develop MALT1 inhibitors.

SUMMARY OF THE INVENTION

Inhibition of the protease activity of MALT1 has been shown to have anti-proliferative effects on cancer cells (e.g., ABC-DLBCL cells), and be a possible target in the treatment of inflammatory and autoimmune diseases (e.g., rheumatoid arthritis, multiple sclerosis, psoriasis, systemic lupus). Accordingly, the present disclosure stems from the recognition that, by targeting and inhibiting MALT1 proteolytic activity, new compounds, compositions, and methods are provided that are useful for the treatment of diseases associated with the dysregulation of MALT1 activity (e.g., hematological cancers such as DLBCL).

The present disclosure provides compounds that act to bind MALT1 and inhibit its constitutive proteolytic activity, which is common in some cancers, thereby conferring an anti-proliferative effect. The present disclosure also provides methods of treating cancer, inflammatory diseases, and autoimmune diseases with the compounds disclosed herein, and compositions thereof. Thus, the present disclosure represents an important advance in the treatment of cancer, particularly DLBCL, as well as in the treatment of inflammatory and autoimmune diseases.

In one aspect, provided are compounds of Formula I:

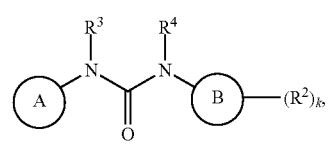

and pharmaceutically acceptable salts, co-crystals, tautomers, stereoisomers, solvates, hydrates, polymorphs, isotopically enriched derivatives, or prodrugs thereof, wherein:
A is

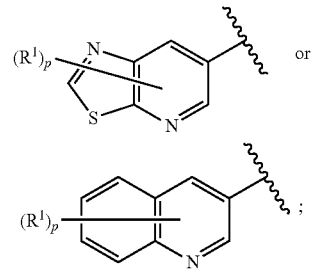

B is pyridinyl;
each occurrence of $R^1$ and $R^2$ is, independently, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted heteroalkyl, —$OR^A$, —$N(R^A)_2$, —$SR^A$, —CN, —SCN, —C(=$NR^A$)$R^A$, —C(=$NR^A$)$OR^A$, —C(=$NR^A$)N($R^A$)$_2$, —C(=O)$R^A$, —C(=O)$OR^A$, —C(=O)N($R^A$)$_2$, —S(=O)$R^A$, —S(=O)$_2R^A$, —$NO_2$, —$NR^A$C(=O)$R^A$, —$NR^A$C(=O)$OR^A$, —$NR^A$C(=O)N($R^A$)$_2$, —$NR^A$S(=O)$R^A$, —$NR^A$S(=O)$_2R^A$, —S(=O)N($R^A$)$_2$, —S(=O)$_2$N($R^A$)$_2$, —OC(=O)$R^A$, —OC(=O)$OR^A$, or —OC(=O)N($R^A$)$_2$;
each occurrence of $R^3$ and $R^4$ is, independently, hydrogen, substituted or unsubstituted alkyl, or a nitrogen protecting group;
each occurrence of $R^A$ is, independently, hydrogen, substituted or unsubstituted acyl, substituted or unsubstituted alkyl, substituted or unsubstituted alkenyl, substituted or unsubstituted alkynyl, substituted or unsubstituted heteroalkyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^A$ groups are joined to form a substituted or unsubstituted heterocyclic ring;

k is 1, 2, 3, or 4; and p is 1, 2, 3, 4, 5, or 6.

In certain embodiments, provided are compounds of Formula I:

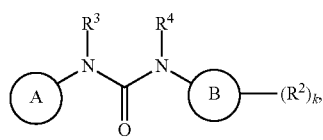

and pharmaceutically acceptable salts, co-crystals, tautomers, stereoisomers, solvates, hydrates, polymorphs, isotopically enriched derivatives, or prodrugs thereof, wherein:

A is

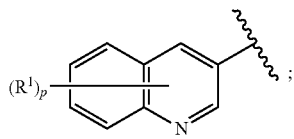

B is pyridinyl;

each occurrence of $R^1$ and $R^2$ is, independently, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted heteroalkyl, —$OR^A$, —$N(R^A)_2$, —$SR^A$, —CN, —SCN, —C(=$NR^A$)$R^A$, —C(=$NR^A$)$OR^A$, —C(=$NR^A$)N($R^A$)$_2$, —C(=O)$R^A$, —C(=O)$OR^A$, —C(=O)N($R^A$)$_2$, —S(=O)$R^A$, —S(=O)$_2R^A$, —$NO_2$, —$NR^A$C(=O)$R^A$, —$NR^A$C(=O)$OR^A$, —$NR^A$C(=O)N($R^A$)$_2$, —$NR^A$S(=O)$R^A$, —$NR^A$S(=O)$_2R^A$, —S(=O)N($R^A$)$_2$, —S(=O)$_2$N($R^A$)$_2$, —OC(=O)$R^A$, —OC(=O)$OR^A$, or —OC(=O)N($R^A$)$_2$;

each occurrence of $R^3$ and $R^4$ is, independently, hydrogen, substituted or unsubstituted alkyl, or a nitrogen protecting group;

each occurrence of $R^A$ is, independently, hydrogen, substituted or unsubstituted acyl, substituted or unsubstituted alkyl, substituted or unsubstituted alkenyl, substituted or unsubstituted alkynyl, substituted or unsubstituted heteroalkyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^A$ groups are joined to form a substituted or unsubstituted heterocyclic ring;

k is 1, 2, 3, or 4; and p is 1, 2, 3, 4, 5, or 6.

Exemplary compounds of Formula I include, but are not limited to:

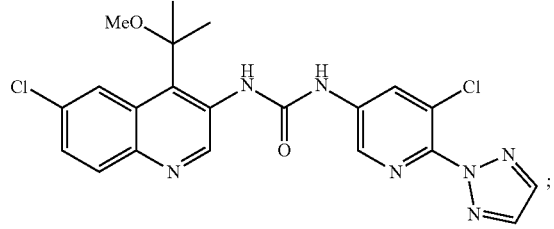

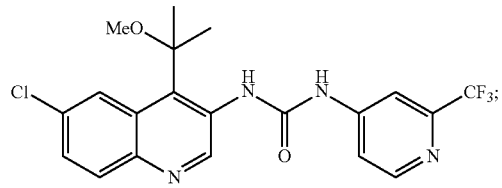

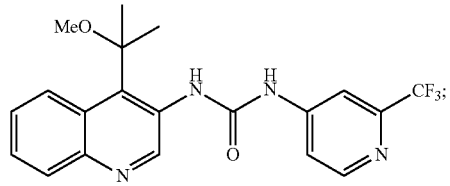

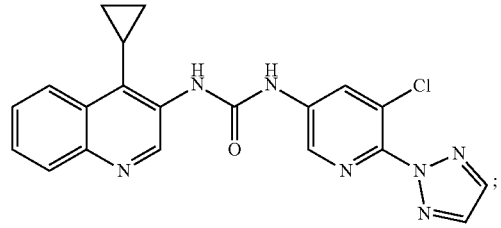

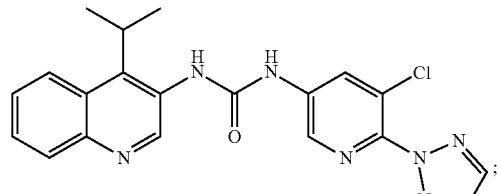

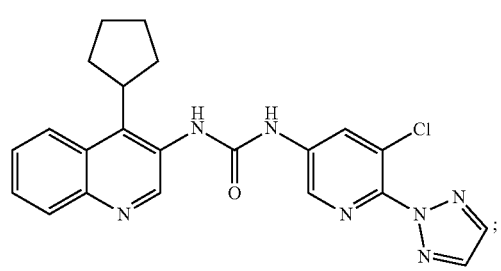

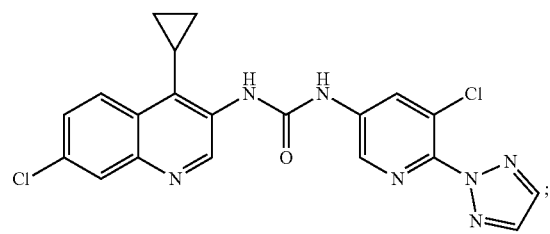

-continued
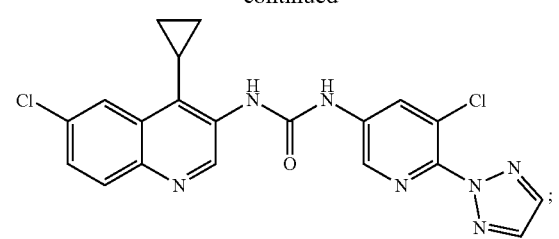
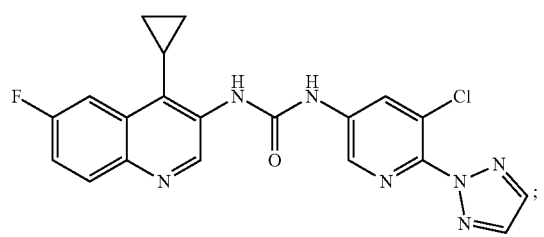
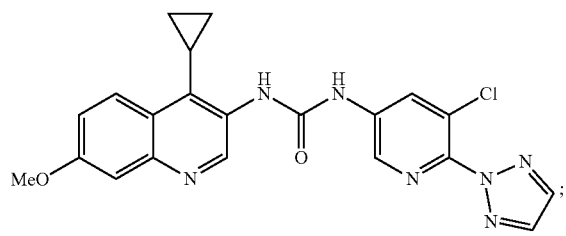
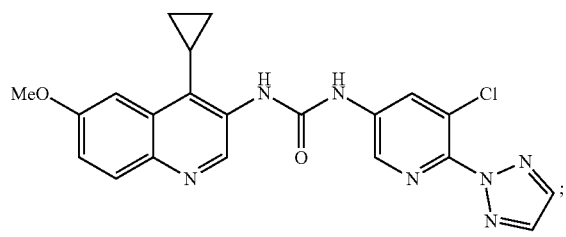
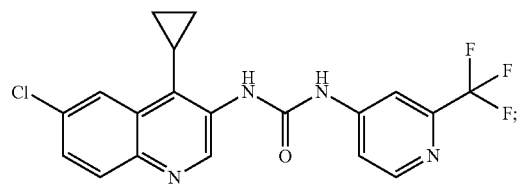
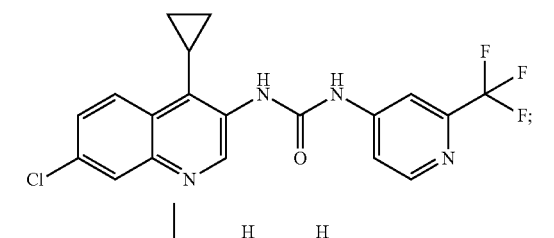
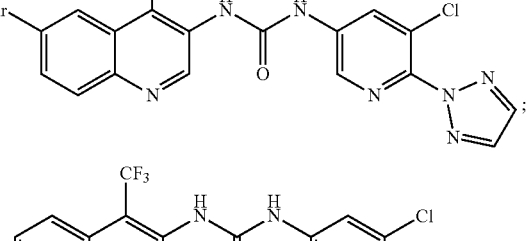
-continued
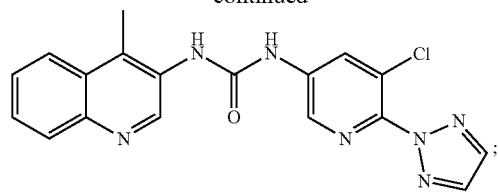
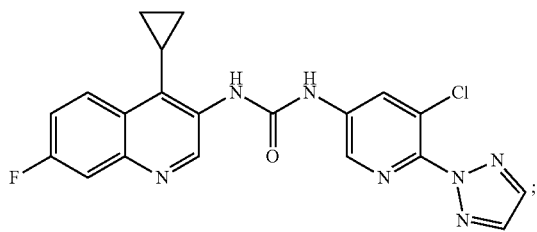
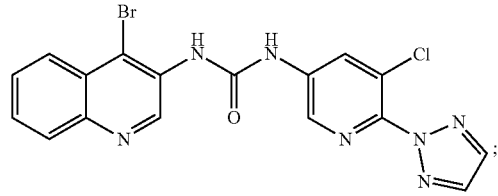
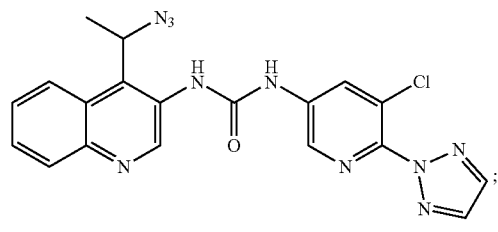
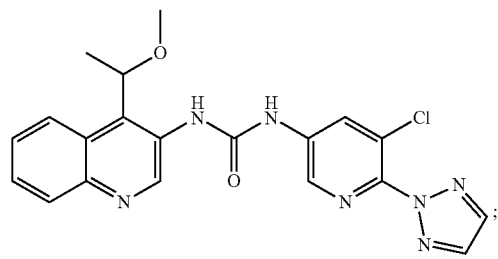
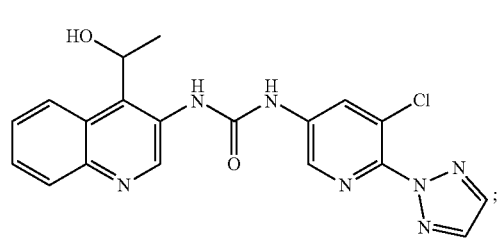
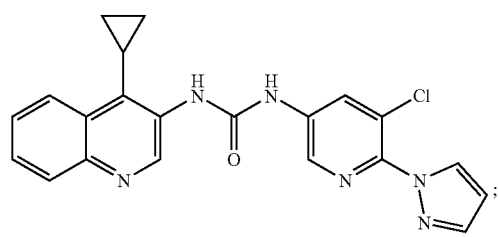

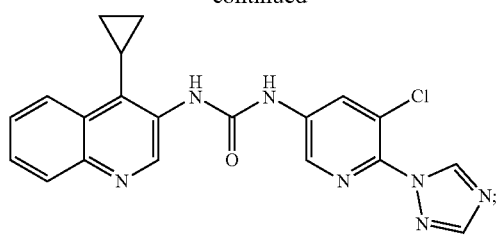
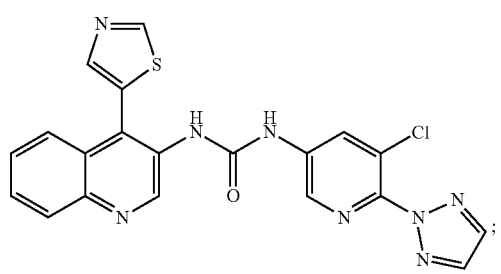
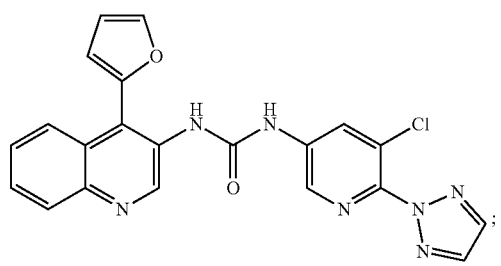
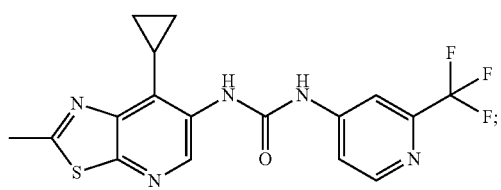
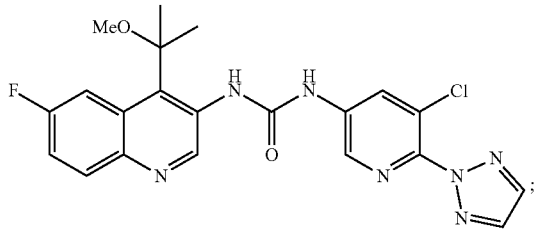
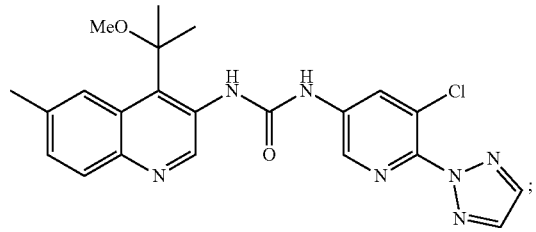
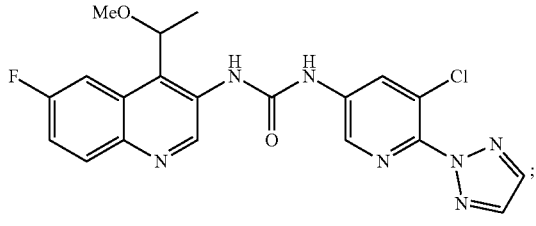
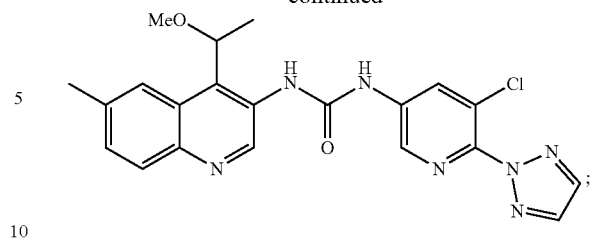
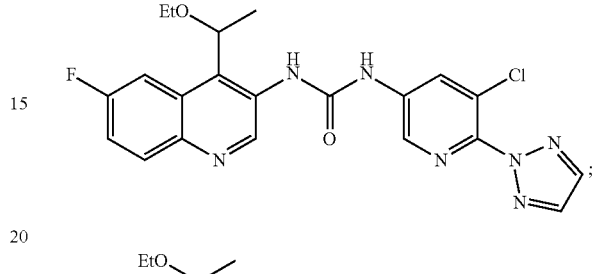
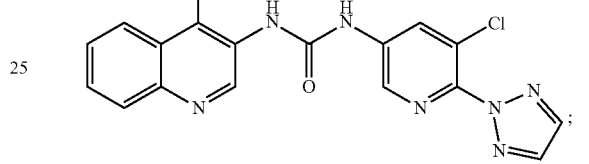
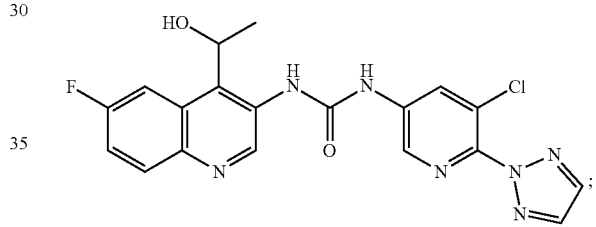
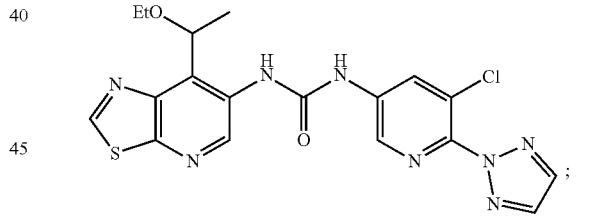
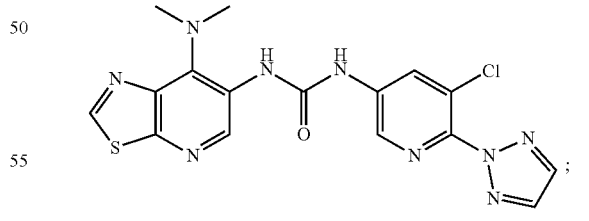
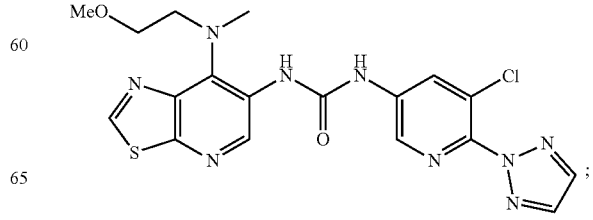

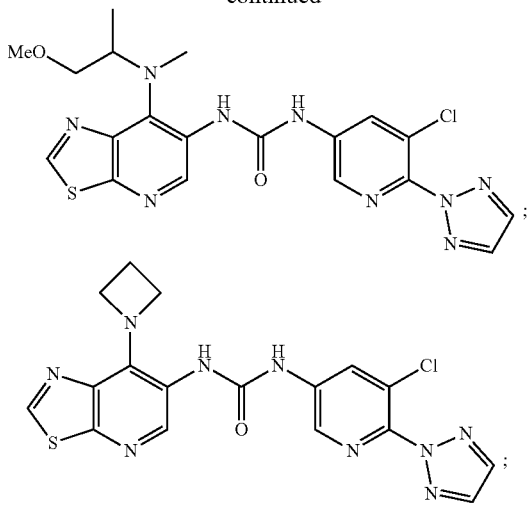

and pharmaceutically acceptable salts thereof.

In another aspect, provided are pharmaceutical compositions comprising a compound of Formula I, or a pharmaceutically acceptable salt thereof, and optionally a pharmaceutically acceptable excipient.

In another aspect, provided are methods of treating cancer in a subject in need thereof, the method comprising administering a compound of Formula I, or a pharmaceutically acceptable salt thereof, or a pharmaceutical composition comprising a compound of Formula I to the subject. In certain embodiments, the cancer is a hematological cancer. In certain embodiments, the cancer is a lymphoid malignancy. In certain embodiments, the hematological cancer is a leukemia, lymphoma, or multiple myeloma. In certain embodiments, the cancer is mantle cell lymphoma. In certain embodiments, the cancer is a diffuse large B-cell lymphoma (e.g., ABC-DLBCL).

In another aspect, provided are methods of inhibiting the activity of MALT1, the method comprising contacting a compound of Formula I, or a pharmaceutically acceptable salt thereof, with MALT1. In certain embodiments, the MALT1 is in a cell (e.g., a human cell)

In another aspect, provided are compounds of Formula I, or pharmaceutically acceptable salts thereof, or pharmaceutical compositions comprising a compound of Formula I, or pharmaceutically acceptable salts thereof, for use in treating cancer in a subject in need thereof (e.g., ABC-DLBCL).

In another aspect, provided are kits comprising a compound of Formula I, or a pharmaceutically acceptable salt thereof, or a pharmaceutical composition comprising a compound of Formula I, or pharmaceutically acceptable salts thereof. In certain embodiments, the kits further comprise instructions for administration (e.g., human administration).

The details of certain embodiments of the invention are set forth in the Detailed Description of Certain Embodiments, as described below. Other features, objects, and advantages of the invention will be apparent from the Definitions, Examples, and Claims.

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March, *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., Enantiomers, Racemates and Resolutions (Wiley Interscience, New York, 1981); Wilen et al., Tetrahedron 33:2725 (1977); Eliel, E. L. Stereochemistry of Carbon Compounds (McGraw-Hill, N Y, 1962); and Wilen, S. H., Tables of Resolving Agents and Optical Resolutions p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

In a formula, ∿∿ is a single bond where the stereochemistry of the moieties immediately attached thereto is not specified, --- is absent or a single bond, and = or ≡ is a single or double bond.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{18}F$, or the replacement of $^{12}C$ with $^{13}C$ or $^{14}C$ are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn).

The term "haloalkyl" is a substituted alkyl group, wherein one or more of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). Examples of haloalkyl groups include —$CHF_2$, —$CH_2F$, —$CF_3$, —$CH_2CF_3$, —$CF_2CF_3$, —$CF_2CF_2CF_3$, —$CCl_3$, —$CFCl_2$, —$CF_2Cl$, and the like.

The term "hydroxyalkyl" is a substituted alkyl group, wherein one or more of the hydrogen atoms are independently replaced by a hydroxyl. In some embodiments, the hydroxyalkyl moiety has 1 to 8 carbon atoms ("$C_{1-8}$ hydroxyalkyl"). In some embodiments, the hydroxyalkyl moiety has 1 to 6 carbon atoms ("$C_{1-6}$ hydroxyalkyl"). In some embodiments, the hydroxyalkyl moiety has 1 to 4 carbon atoms ("$C_{1-4}$ hydroxyalkyl"). In some embodiments, the hydroxyalkyl moiety has 1 to 3 carbon atoms ("$C_{1-3}$ hydroxyalkyl"). In some embodiments, the hydroxyalkyl moiety has 1 to 2 carbon atoms ("$C_{1-2}$ hydroxyalkyl").

The term "azidoalkyl" is a substituted alkyl group, wherein one or more of the hydrogen atoms are independently replaced by an azide (—$N_3$). In some embodiments, the azidoalkyl moiety has 1 to 8 carbon atoms ("$C_{1-8}$ azidoalkyl"). In some embodiments, the azidoalkyl moiety has 1 to 6 carbon atoms ("$C_{1-6}$ azidoalkyl"). In some embodiments, the azidoalkyl moiety has 1 to 4 carbon atoms ("$C_{1-4}$ azidoalkyl"). In some embodiments, the azidoalkyl moiety has 1 to 3 carbon atoms ("$C_{1-3}$ azidoalkyl"). In some embodiments, the azidoalkyl moiety has 1 to 2 carbon atoms ("$C_{1-2}$ azidoalkyl").

The term "alkoxy" refers to an alkyl group, as defined herein, appended to the parent molecular moiety through an oxygen atom. In some embodiments, the alkoxy moiety has 1 to 8 carbon atoms ("$C_{1-8}$ alkoxy"). In some embodiments, the alkoxy moiety has 1 to 6 carbon atoms ("$C_{1-6}$ alkoxy"). In some embodiments, the alkoxy moiety has 1 to 4 carbon atoms ("$C_{1-4}$ alkoxy"). In some embodiments, the alkoxy moiety has 1 to 3 carbon atoms ("$C_{1-3}$ alkoxy"). In some embodiments, the alkoxy moiety has 1 to 2 carbon atoms ("$C_{1-2}$ alkoxy"). Representative examples of alkoxy include, but are not limited to, methoxy, ethoxy, propoxy, 2-propoxy, butoxy and tert-butoxy.

The term "alkoxyalkyl" is a substituted alkyl group, wherein one or more of the hydrogen atoms are independently replaced by an alkoxy group, as defined herein. In some embodiments, the alkoxyalkyl moiety has 1 to 8 carbon atoms ("$C_{1-8}$ alkoxyalkyl"). In some embodiments, the alkoxyalkyl moiety has 1 to 6 carbon atoms ("$C_{1-6}$ alkoxyalkyl"). In some embodiments, the alkoxyalkyl moiety has 1 to 4 carbon atoms ("$C_{1-4}$ alkoxyalkyl"). In some embodiments, the alkoxyalkyl moiety has 1 to 3 carbon atoms ("$C_{1-3}$ alkoxyalkyl"). In some embodiments, the alkoxyalkyl moiety has 1 to 2 carbon atoms ("$C_{1-2}$ alkoxyalkyl").

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 20 carbon atoms and 1 or more heteroatoms within the parent chain ("hetero$C_{1-20}$ alkyl"). In some embodiments, a heteroalkyl group is a saturated group having 1 to 18 carbon atoms and 1 or more heteroatoms within the parent chain ("hetero$C_{1-18}$ alkyl"). In some embodiments, a heteroalkyl group is a saturated group having 1 to 16 carbon atoms and 1 or more heteroatoms within the parent chain ("hetero$C_{1-16}$ alkyl"). In some embodiments, a heteroalkyl group is a saturated group having 1 to 14 carbon atoms and 1 or more heteroatoms within the parent chain ("hetero$C_{1-14}$ alkyl"). In some embodiments, a heteroalkyl group is a saturated group having 1 to 12 carbon atoms and 1 or more heteroatoms within the parent chain ("hetero$C_{1-12}$ alkyl"). In some embodiments, a heteroalkyl group is a saturated group having 1 to 10 carbon atoms and 1 or more heteroatoms within the parent chain ("hetero$C_{1-10}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, the heteroalkyl group defined herein is a partially unsaturated group having 1 or more heteroatoms within the parent chain and at least one unsaturated carbon, such as a carbonyl group. For example, a heteroalkyl group may comprise an amide or ester functionality in its parent chain such that one or more carbon atoms are unsaturated carbonyl groups. Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-20}$ alkyl. In certain embodiments, the heteroalkyl group is an unsubstituted heteroC$_{1-10}$ alkyl. In certain embodiments, the heteroalkyl group is a substituted heteroC$_{1-20}$ alkyl. In certain embodiments, the heteroalkyl group is an unsubstituted heteroC$_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("C$_{2-9}$ alkenyl"). In some embodiments, an alkenyl group has 2 to 8 carbon atoms ("C$_{2-8}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_9$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted C$_{2-10}$ alkenyl. In certain embodiments, the alkenyl group is a substituted C$_{2-10}$ alkenyl. In an alkenyl group, a C=C double bond for which the stereochemistry is not specified (e.g., —CH=CHCH$_3$ or

)

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C), and the like. Additional examples of alkynyl include heptynyl (C$_7$), octynyl (C), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-s}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In some embodiments, a carbocyclyl group has 3 to 10 ring carbon atoms ("C$_{3-10}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted C$_{3-14}$ carbocyclyl. In certain embodiments, the carbocyclyl group is a substituted C$_{3-14}$ carbocyclyl.

In some embodiments, "carbocyclyl" is a monocyclic, saturated carbocyclyl group having from 3 to 14 ring carbon atoms ("C$_{3-14}$ cycloalkyl"). In some embodiments, a cycloalkyl group has 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 4 to 6 ring carbon atoms ("C$_{4-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted C$_{3-14}$ cycloalkyl. In certain embodiments, the cycloalkyl group is a substituted C$_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 T electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14 T electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl, and phenazinyl.

"Heteroaralkyl" is a subset of "alkyl" and refers to an alkyl group substituted by a heteroaryl group, wherein the point of attachment is on the alkyl moiety.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_3$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)

$OR^{aa}$, $-C(=NR^{cc})N(R^{cc})_2$, $-SO_2N(R^{cc})_2$, $-SO_2R^{cc}$, $-SO_2OR^{cc}$, $-SOR^{aa}$, $-C(=S)N(R^{cc})_2$, $-C(=O)SR^{cc}$, $-C(=S)SR^{cc}$, $-P(=O)(R^{aa})_2$, $-P(=O)(OR^{cc})_2$, $-P(=O)(N(R^{cc})_2)_2$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, $-CN$, $-NO_2$, $-N_3$, $-SO_2H$, $-SO_3H$, $-OH$, $-OR^{ee}$, $-ON(R^{ff})_2$, $-N(R^{ff})_2$, $-N(R^{ff})_3^+X^-$, $-N(OR^{ee})R^{ff}$, $-SH$, $-SR^{ee}$, $-SSR^{ee}$, $-C(=O)R^{ee}$, $-CO_2H$, $-CO_2R^{ee}$, $-OC(=O)R^{ee}$, $-OCO_2R^{ee}$, $-C(=O)N(R^{ff})_2$, $-OC(=O)N(R^{ff})_2$, $-NR^{ff}C(=O)R^{ee}$, $-NR^{ff}CO_2R^{ee}$, $-NR^{ff}C(=O)N(R^{ff})_2$, $-C(=NR^{ff})OR^{ee}$, $-OC(=NR^{ff})R^{ee}$, $-OC(=NR^{ff})OR^{ee}$, $-C(=NR^{ff})N(R^{ff})_2$, $-OC(=NR^{ff})N(R^{ff})_2$, $-NR^{ff}C(=NR^{ff})N(R^{ff})_2$, $-NR^{ff}SO_2R^{ee}$, $-SO_2N(R^{ff})_2$, $-SO_2R^{ee}$, $-SO_2OR^{ee}$, $-OSO_2R^{ee}$, $-S(=O)R^{ee}$, $-Si(R^{ee})_3$, $-OSi(R^{ee})_3$, $-C(=S)N(R^{ff})_2$, $-C(=O)SR^{ee}$, $-C(=S)SR^{ee}$, $-SC(=S)SR^{ee}$, $-P(=O)(OR^{ee})_2$, $-P(=O)(R^{ee})_2$, $-OP(=O)(R^{ee})_2$, $-OP(=O)(OR^{ee})_2$, $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form $=O$ or $=S$; wherein $X^-$ is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, 3-10 membered heterocyclyl, $C_{6-10}$ aryl and 5-10 membered heteroaryl, or two $R^f$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, $-CN$, $-NO_2$, $-N_3$, $-SO_2H$, $-SO_3H$, $-OH$, $-OC_{1-6}$ alkyl, $-ON(C_{1-6}$ alkyl$)_2$, $-N(C_{1-6}$ alkyl$)_2$, $-N(C_{1-6}$ alkyl$)_3^+X^-$, $-NH(C_{1-6}$ alkyl$)_2^+X^-$, $-NH_2(C_{1-6}$ alkyl$)^+X^-$, $-NH_3^+X^-$, $-N(OC_{1-6}$ alkyl$)(C_{1-6}$ alkyl$)$, $-N(OH)(C_{1-6}$ alkyl$)$, $-NH(OH)$, $-SH$, $-SC_{1-6}$ alkyl, $-SS(C_{1-6}$ alkyl$)$, $-C(=O)(C_{1-6}$ alkyl$)$, $-CO_2H$, $-CO_2(C_{1-6}$ alkyl$)$, $-OC(=O)(C_{1-6}$ alkyl$)$, $-OCO_2(C_{1-6}$ alkyl$)$, $-C(=O)NH_2$, $-C(=O)N(C_{1-6}$ alkyl$)_2$, $-OC(=O)NH(C_{1-6}$ alkyl$)$, $-NHC(=O)(C_{1-6}$ alkyl$)$, $-N(C_{1-6}$ alkyl$)C(=O)(C_{1-6}$ alkyl$)$, $-NHCO_2(C_{1-6}$ alkyl$)$, $-NHC(=O)N(C_{1-6}$ alkyl$)_2$, $-NHC(=O)NH(C_{1-6}$ alkyl$)$, $-NHC(=O)NH_2$, $-C(=NH)O(C_{1-6}$ alkyl$)$, $-OC(=NH)(C_{1-6}$ alkyl$)$, $-OC(=NH)OC_{1-6}$ alkyl, $-C(=NH)N(C_{1-6}$ alkyl$)_2$, $-C(=NH)NH(C_{1-6}$ alkyl$)$, $-C(=NH)NH_2$, $-OC(=NH)N(C_{1-6}$ alkyl$)_2$, $-OC(=NH)NH(C_{1-6}$ alkyl$)$, $-OC(=NH)NH_2$, $-NHC(=NH)N(C_{1-6}$ alkyl$)_2$, $-NHC(=NH)NH_2$, $-NHSO_2(C_{1-6}$ alkyl$)$, $-SO_2N(C_{1-6}$ alkyl$)_2$, $-SO_2NH(C_{1-6}$ alkyl$)$, $-SO_2NH_2$, $-SO_2(C_{1-6}$ alkyl$)$, $-SO_2O(C_{1-6}$ alkyl$)$, $-OSO_2(C_{1-6}$ alkyl$)$, $-SO(C_{1-6}$ alkyl$)$, $-Si(C_{1-6}$ alkyl$)_3$, $-OSi(C_{1-6}$ alkyl$)_3$-$C(=S)N(C_{1-6}$ alkyl$)_2$, $C(=S)NH(C_{1-6}$ alkyl$)$, $C(=S)NH_2$, $-C(=O)S(C_{1-6}$ alkyl$)$, $-C(=S)SC_{1-6}$ alkyl, $-SC(=S)SC_{1-6}$ alkyl, $-P(=O)(OC_{1-6}$ alkyl$)_2$, $-P(=O)(C_{1-6}$ alkyl$)_2$, $-OP(=O)(C_{1-6}$ alkyl$)_2$, $-OP(=O)(OC_{1-6}$ alkyl$)_2$, $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form $=O$ or $=S$; wherein $X^-$ is a counterion.

The term "halo" or "halogen" refers to fluorine (fluoro, $-F$), chlorine (chloro, $-C_1$), bromine (bromo, $-Br$), or iodine (iodo, $-I$).

The term "hydroxyl" or "hydroxy" refers to the group $-OH$. The term "substituted hydroxyl" or "substituted hydroxyl," by extension, refers to a hydroxyl group wherein the oxygen atom directly attached to the parent molecule is substituted with a group other than hydrogen, and includes groups selected from $-OR^{aa}$, $-ON(R^{bb})_2$, $-OC(=O)SR^{aa}$, $-OC(=O)R^{aa}$, $-OCO_2R^{aa}$, $-OC(=O)N(R^{bb})_2$, $-OC(=NR^{bb})R^{aa}$, $-OC(=NR^{bb})OR^{aa}$, $-OC(=NR^{bb})N(R^{bb})_2$, $-OS(=O)R^{aa}$, $-OSO_2R^{aa}$, $-OSi(R^{aa})_3$, $-OP(R^{cc})_2$, $-OP(R^{cc})_3^+X$, $-OP(OR^{cc})_2$, $-OP(OR^{cc})_3^+X$, $-OP(=O)(R^{aa})_2$, $-OP(=O)(OR^{cc})_2$, and $-OP(=O)(N(R^{bb})_2)_2$, wherein X, $R^{aa}$, $R^{bb}$, and $R^{cc}$ as defined herein.

The term "amino" refers to the group $-NH_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from $-NH(R^{bb})$, $-NHC(=O)R^{aa}$, $-NHCO_2R^{aa}$, $-NHC(=O)N(R^{bb})_2$, $-NHC(=NR^{bb})N(R^{bb})_2$, $-NHSO_2R^{aa}$, $-NHP(=O)(OR^{cc})_2$, and $-NHP(=O)(N(R^{bb})_2)_2$, wherein $R^{aa}$, $R^{bb}$ and $R^{cc}$ are as defined herein, and wherein $R^{bb}$ of the group $-NH(R^{bb})$ is not hydrogen.

The term "disubstituted amino" refers to an amino group wherein the nitrogen atom directly attached to the parent molecule is substituted with two groups other than hydrogen, and includes groups selected from $-N(R^{bb})_2$, $-NR^{bb}C(=O)R^{aa}$, $-NR^{bb}CO_2R^{aa}$, $-NR^{bb}C(=O)N(R^{bb})_2$, $-NR^{bb}C(=NR^{bb})N(R^{bb})_2$, $-NR^{bb}SO_2R^{aa}$, $-NR^{bb}P(=O)(OR^{cc})_2$, and $-NR^{bb}P(=O)(N(R^{bb})_2)_2$, wherein $R^{aa}$, $R^{bb}$ and $R^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N($R^{bb}$)$_3$ and —N($R^{bb}$)$_3$$^+$X$^-$, wherein $R^{bb}$ and X$^-$ are as defined herein.

The term "sulfonyl" refers to a group selected from —SO$_2$N($R^{bb}$)$_2$, —SO$_2$R$^{aa}$, and —SO$_2$OR$^{aa}$, wherein R$^{aa}$ and $R^{bb}$ are as defined herein.

The term "sulfinyl" refers to the group —S(=O)R$^{aa}$, wherein R$^{aa}$ is as defined herein.

The term "acyl" refers to a group having the general formula —C(=O)R$^{X1}$, —C(=O)OR$^{X1}$, —C(=O)—O—C(=O)R$^{X1}$, —C(=O)SR$^{X1}$, —C(=O)N(R$^{X1}$)$_2$, —C(=S)R$^{X1}$, —C(=S)N(R$^{X1}$)$_2$, —C(=S)O(R$^{X1}$), —C(=S)S(R$^{X1}$), —C(=NR$^{X1}$)R$^{X1}$, —C(=NR$^{X1}$)OR$^{X1}$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two R$^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "carbonyl" refers a group wherein the carbon directly attached to the parent molecule is sp$^2$ hybridized, and is substituted with an oxygen, nitrogen or sulfur atom, e.g., a group selected from ketones (e.g., —C(=O)R$^{aa}$), carboxylic acids (e.g., —CO$_2$H), aldehydes (—CHO), esters (e.g., —CO$_2$R$^{aa}$, —C(=O)SR$^{aa}$, —C(=S)SR$^{aa}$), amides (e.g., —C(=O)N($R^{bb}$)$_2$, —C(=O)NR$^{bb}$SO$_2$R$^{aa}$, —C(=S)N($R^{bb}$)$_2$), and imines (e.g., —C(=NR$^{bb}$)R$^{aa}$, —C(=NR$^{bb}$)OR$^{aa}$) C(=NR$^{bb}$)N($R^{bb}$)$_2$), wherein R$^{aa}$ and R$^{bb}$ are as defined herein.

The term "silyl" refers to the group —Si(R$^{aa}$)$_3$, wherein R$^{aa}$ is as defined herein.

The term "boronyl" refers to boranes, boronic acids, boronic esters, borinic acids, and borinic esters, e.g., boronyl groups of the formula —B(R$^{aa}$)$_2$, —B(OR$^{cc}$)$_2$, and —BR$^{aa}$(OR$^{cc}$) wherein R$^{aa}$ and R$^{cc}$ are as defined herein.

The term "phosphino" refers to the group —P(R$^{cc}$)$_3$, wherein R$^{cc}$ is as defined herein. An exemplary phosphino group is triphenylphosphine.

The term "phosphono" refers to the group —O(P=O)(OR$^{cc}$)R$^{aa}$, wherein R$^{aa}$ and R$^{cc}$ are as defined herein.

The term "phosphoramido" refers to the group —O(P=O)(N($R^{bb}$)$_2$)$_2$, wherein each $R^{bb}$ is as defined herein.

The term "stannyl" refers to the group —Sn(R$^{cc}$)$_3$, wherein R$^{cc}$ is as defined herein.

The term "germyl" refers to the group —Ge(R$^{cc}$)$_3$, wherein R$^{cc}$ is as defined herein.

The term "arsenyl" refers to the group —As(R$^{cc}$)$_3$, wherein R$^{cc}$ is as defined herein.

The term "oxo" refers to the group =O, and the term "thiooxo" refers to the group =S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$-alkenyl, heteroC$_{2-10}$-alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, $R^{bb}$, R$^{cc}$ and R$^{dd}$ are as defined herein.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, $R^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), 0-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys). In certain embodiments, a nitrogen protecting group is benzyl (Bn), tert-butyloxycarbonyl (BOC), carbobenzyloxy (Cbz), 9-flurenylmethyloxycarbonyl (Fmoc), trifluoroacetyl, triphenylmethyl, acetyl (Ac), benzoyl (Bz), p-methoxybenzyl (PMB), 3,4-dimethoxybenzyl (DMPM), p-methoxyphenyl (PMP), 2,2,2-trichloroethyloxycarbonyl (Troc), triphenylmethyl (Tr), tosyl (Ts), brosyl (Bs), nosyl (Ns), mesyl (Ms), triflyl (Tf), or dansyl (Ds).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)(R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$^{cc}$ are as defined herein. Oxygen protecting groups are well known in the art and include those described in detail in Protecting Groups in Organic Synthesis, T. W. Greene and P. G. M. Wuts, 3rd edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). In certain embodiments, an oxygen protecting group is silyl. In certain embodiments, an oxygen protecting group is t-butyldiphenylsilyl (TBDPS), t-butyldimethylsilyl (TBDMS), triisoproylsilyl (TIPS), triphenylsilyl (TPS), triethylsilyl (TES), trimethylsilyl (TMS), triisopropylsiloxymethyl (TOM), acetyl (Ac), benzoyl (Bz), allyl carbonate, 2,2,2-trichloroethyl carbonate (Troc), 2-trimethylsilylethyl carbonate, methoxymethyl (MOM), 1-ethoxyethyl (EE), 2-methyoxy-2-propyl (MOP), 2,2,2-trichloroethoxyethyl, 2-methoxyethoxymethyl (MEM), 2-trimethylsilylethoxymethyl (SEM), methylthiomethyl (MTM), tetrahydropyranyl (THP), tetrahydrofuranyl (THF), p-methoxyphenyl (PMP), triphenylmethyl (Tr), methoxytrityl (MMT), dimethoxytrityl (DMT), allyl, p-methoxybenzyl (PMB), t-butyl, benzyl (Bn), allyl, or pivaloyl (Piv).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3^+X^-$, —$P(OR^{cc})_2$, —$P(OR^{cc})_3^+X^-$, —$P(=O)(R^{aa})_2$, —$P(=O)(OR^{cc})_2$, and —$P(=O)(N(R^{bb})2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, 3rd edition, John Wiley & Sons, 1999, incorporated herein by reference. In certain embodiments, a sulfur protecting group is acetamidomethyl, t-Bu, 3-nitro-2-pyridine sulfenyl, 2-pyridine-sulfenyl, or triphenylmethyl.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3^-$, ClO$_4^-$, OH$^-$, H$_2$PO$_4^-$, HCO$_3^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4^-$, PF$_4^-$, PF$_6^-$, AsF$_6^-$, SbF$_6^-$, B[3,5-(CF$_3$)$_2$C$_6$H$_3$]$_4^-$, B(C$_6$F$_5$)$_4^-$, BPh$_4^-$, Al(OC(CF$_3$)$_3$)$_4^-$, and carborane anions (e.g., CB$_{11}$H$_{12}^-$ or (HCB$_{11}$Me$_5$Br$_6$)$^-$). Exemplary counterions which may be multivalent include CO$_3^{2-}$, HPO$_4^{2-}$, PO$_4^{3-}$, B$_4$O$_7^{2-}$, SO$_4^{2-}$, S$_2$O$_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

The term "leaving group" is given its ordinary meaning in the art of synthetic organic chemistry and refers to an atom or a group capable of being displaced by a nucleophile. See, for example, Smith, *March's Advanced Organic Chemistry* 6th ed. (501-502). Examples of suitable leaving groups include, but are not limited to, halogen (such as F, C$_l$, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, -OTs), methanesulfonate (mesylate, -OMs), p-bromobenzenesulfonyloxy (brosylate, —OBs), —OS(=O)$_2$(CF$_2$)$_3$CF$_3$ (nonaflate, —ONf), or trifluoromethanesulfonate (triflate, -OTf). In some cases, the leaving group is a brosylate, such as p-bromobenzenesulfonyloxy. In some cases, the leaving group is a nosylate, such as 2-nitrobenzenesulfonyloxy. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties. Further exemplary leaving groups include, but are not limited to, halo (e.g., chloro, bromo, iodo) and activated substituted hydroxyl groups (e.g., —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein).

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

A "non-hydrogen group" refers to any group that is defined for a particular variable that is not hydrogen.

These and other exemplary substituents are described in more detail in the Detailed Description, Examples, and claims. The invention is not intended to be limited in any manner by the above exemplary listing of substituents.

Other Definitions

The following definitions are more general terms used throughout the present application.

As used herein, the term "salt" refers to any and all salts, and encompasses pharmaceutically acceptable salts.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and N$^+$(C$_{1-4}$ alkyl)$_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R.x H$_2$O, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R-0.5H$_2$O)), and polyhydrates (x is a number greater than 1, e.g., dihydrates (R.2 H$_2$O) and hexahydrates (R.6H$_2$O)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorph" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_{1-8}$ alkyl, $C_{2-8}$ alkenyl, $C_{2-8}$ alkynyl, aryl, $C_{7-12}$ substituted aryl, and $C_{7-12}$ arylalkyl esters of the compounds described herein may be preferred.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. The term "patient" refers to a human subject in need of treatment of a disease. The subject may also be a plant. In certain embodiments, the plant is a land plant. In certain embodiments, the plant is a non-vascular land plant. In certain embodiments, the plant is a vascular land plant. In certain embodiments, the plant is a seed plant. In certain embodiments, the plant is a cultivated plant. In certain embodiments, the plant is a dicot. In certain embodiments, the plant is a monocot. In certain embodiments, the plant is a flowering plant. In some embodiments, the plant is a cereal plant, e.g., maize, corn, wheat, rice, oat, barley, rye, or millet. In some embodiments, the plant is a legume, e.g., a bean plant, e.g., soybean plant. In some embodiments, the plant is a tree or shrub.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The term "target tissue" refers to any biological tissue of a subject (including a group of cells, a body part, or an organ) or a part thereof, including blood and/or lymph vessels, which is the object to which a compound, particle, and/or composition of the invention is delivered. A target tissue may be an abnormal or unhealthy tissue, which may need to be treated. A target tissue may also be a normal or healthy tissue that is under a higher than normal risk of becoming abnormal or unhealthy, which may need to be prevented. In certain embodiments, the target tissue is the liver. In certain embodiments, the target tissue is the lung. A "non-target tissue" is any biological tissue of a subject (including a group of cells, a body part, or an organ) or a part thereof, including blood and/or lymph vessels, which is not a target tissue.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms). Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose.

In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent. In certain embodiments, a therapeutically effective amount is an amount sufficient for MALT1 inhibition. In certain embodiments, a therapeutically effective amount is an amount sufficient for treating cancer (e.g., DLBCL). In certain embodiments, a therapeutically effective amount is an amount sufficient for MALT1 inhibition and treating cancer (e.g., DLBCL).

A "prophylactically effective amount" of a compound described herein is an amount sufficient to prevent a condition, or one or more signs or symptoms associated with the condition, or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent. In certain embodiments, a prophylactically effective amount is an amount sufficient for MALT1 inhibition. In certain embodiments, a prophylactically effective amount is an amount sufficient for treating cancer (e.g., lymphoma, mantle cell lymphoma, DLBCL). In certain embodiments, a prophylactically effective amount is an amount sufficient for MALT1 inhibition and treating cancer (e.g., lymphoma, mantle cell lymphoma, DLBCL).

As used herein, the term "inhibit" or "inhibition" in the context of enzymes, for example, in the context of MALT1, refers to a reduction in the activity of the enzyme. In some embodiments, the term refers to a reduction of the level of enzyme activity, e.g., MALT1 activity, to a level that is statistically significantly lower than an initial level, which may, for example, be a baseline level of enzyme activity. In some embodiments, the term refers to a reduction of the level of enzyme activity, e.g., MALT1 activity, to a level that is less than 75%, less than 50%, less than 40%, less than 30%, less than 25%, less than 20%, less than 10%, less than 9%, less than 8%, less than 7%, less than 6%, less than 5%, less than 4%, less than 3%, less than 2%, less than 1%, less than 0.5%, less than 0.1%, less than 0.01%, less than 0.001%, or less than 0.0001% of an initial level, which may, for example, be a baseline level of enzyme activity.

The term "cancer" refers to a malignant neoplasm (*Stedman's Medical Dictionary*, 25th ed.; Hensyl ed.; Williams & Wilkins: Philadelphia, 1990). Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematological cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenstram's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "immunotherapy" refers to a therapeutic agent that promotes the treatment of disease by inducing, enhancing, or suppressing an immune response. Immunotherapies designed to elicit or amplify an immune response are classified as activation immunotherapies, while immunotherapies that reduce or suppress are classified as suppression immunotherapies. Immunotherapies are typically, but not always, biotherapeutic agents. Numerous immunotherapies are used to treat cancer. These include, but are not limited to, monoclonal antibodies, adoptive cell transfer, cytokines, chemokines, vaccines, and small molecule inhibitors.

The terms "biologic," "biologic drug," and "biological product" refer to a wide range of products such as vaccines, blood and blood components, allergenics, somatic cells, gene therapy, tissues, nucleic acids, and proteins. Biologics may include sugars, proteins, or nucleic acids, or complex combinations of these substances, or may be living entities, such as cells and tissues. Biologics may be isolated from a variety of natural sources (e.g., human, animal, microorganism) and may be produced by biotechnological methods and other technologies.

The term "small molecule" or "small molecule therapeutic" refers to molecules, whether naturally occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than about 1,000 g/mol, not more than about 900 g/mol, not more than about 800 g/mol, not more than about 700 g/mol, not more than about 600 g/mol, not more than about 500 g/mol, not more than about 400 g/mol, not more than about 300 g/mol, not more than about 200 g/mol, or not more than about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and not more than about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention.

The term "therapeutic agent" refers to any substance having therapeutic properties that produce a desired, usually beneficial, effect. For example, therapeutic agents may treat, ameliorate, and/or prevent disease. Therapeutic agents, as disclosed herein, may be biologics or small molecule therapeutics.

The term "chemotherapeutic agent" refers to a therapeutic agent known to be of use in chemotherapy for cancer.

A "hematological cancer" includes a cancer which affects a hematopoietic cell or tissue. Hematological cancers include cancers associated with aberrant hematological content and/or function. Examples of hematological cancers include, but are nor limited to, leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), chronic lymphocytic leukemia (CLL) (e.g., B-cell CLL, T-cell CLL)), lymphoma such as Hodgkin's lymphoma (HL) (e.g., B-cell HL, T-cell HL), non-Hodgkin's lymphoma (NHL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenstram's macroglobulinemia), hairy cell leukemia (HCL), immunoblastic large cell lymphoma, precursor B-lymphoblastic lymphoma, primary central nervous system (CNS) lymphoma, T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma), a mixture of one or more leukemia/lymphoma as described above, multiple myeloma, heavy chain disease (e.g., alpha chain disease, gamma chain disease, mu chain disease) acute nonlymphocytic leukemia (ANLL), acute promyelocytic leukemia (APL), acute myelomonocytic leukemia (AMMoL), polycythemia vera, Wilm's tumor, and Ewing's sarcoma.

DETAILED DESCRIPTION OF CERTAIN EMBODIMENTS

Provided herein are inhibitors of MALT1. In one aspect, the disclosure provides compounds of Formula I, and pharmaceutically acceptable salts, solvates, hydrates, polymorphs, co-crystals, tautomers, stereoisomers, isotopically labeled derivatives, prodrugs, and pharmaceutical compositions thereof. The compounds are useful for the treatment and/or prevention of diseases associated with MALT1 activity (e.g., autoimmune diseases, inflammatory diseases, proliferatives diseases, cancer (e.g., DLBCL)) in a subject in need thereof.

Compounds

The compounds described herein interact with MALT1. As described herein, the therapeutic effect may be a result of inhibition, degradation, modulation, binding, and/or modification of MALT1 by the compounds described herein. In certain embodiments, the compounds inhibit, degrade, modulate, and/or modify MALT1 by binding to an allosteric site of MALT1. The compounds may be provided for use in any composition, kit, or method described herein as a pharmaceutically acceptable salt, co-crystal, tautomer, stereoisomer, solvate, hydrate, polymorph, isotopically enriched derivative, or prodrug thereof.

In one aspect, disclosed is a compound of Formula I:

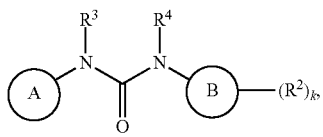

or a pharmaceutically acceptable salt, co-crystal, tautomer, stereoisomer, solvate, hydrate, polymorph, isotopically enriched derivative, or prodrug thereof, wherein:

A is

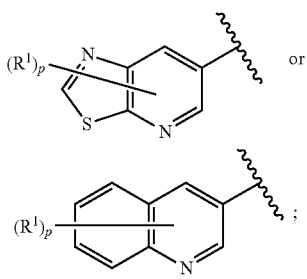

B is pyridinyl;

each occurrence of $R^1$ and $R^2$ is, independently, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted heteroalkyl, —$OR^A$, —$N(R^A)_2$, —$SR^A$, —CN, —SCN, —C(=$NR^A$)$R^A$, —C(=$NR^A$)$OR^A$, —C(=$NR^A$)N($R^A$)$_2$, —C(=O)$R^A$, —C(=O)$OR^A$, —C(=O)N($R^A$)$_2$, —S(=O)$R^A$, —S(=O)$_2R^A$, —$NO_2$, —$NR^A$C(=O)$R^A$, —$NR^A$C(=O)$OR^A$, —$NR^A$C(=O)N($R^A$)$_2$, —$NR^A$S(=O)$R^A$, —$NR^A$S(=O)$_2R^A$, —S(=O)N($R^A$)$_2$, —S(=O)$_2$N($R^A$)$_2$, —OC(=O)$R^A$, —OC(=O)$OR^A$, or —OC(=O)N($R^A$)$_2$;

each occurrence of $R^3$ and $R^4$ is, independently, hydrogen, substituted or unsubstituted alkyl, or a nitrogen protecting group;

each occurrence of $R^A$ is, independently, hydrogen, substituted or unsubstituted acyl, substituted or unsubstituted alkyl, substituted or unsubstituted alkenyl, substituted or unsubstituted alkynyl, substituted or unsubstituted heteroalkyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^A$ groups are joined to form a substituted or unsubstituted heterocyclic ring;

k is 1, 2, 3, 4, 5, or 6; and p is 1, 2, 3, or 4.

In certain embodiments, disclosed is a compound of Formula I:

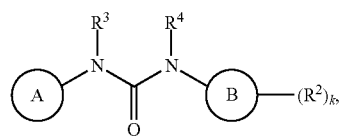

or a pharmaceutically acceptable salt, co-crystal, tautomer, stereoisomer, solvate, hydrate, polymorph, isotopically enriched derivative, or prodrug thereof, wherein:

A is

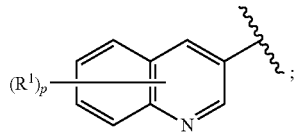

B is pyridinyl;

each occurrence of $R^1$ and $R^2$ is, independently, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted heteroalkyl, —$OR^A$, —$N(R^A)_2$, —$SR^A$, —CN, —SCN, —C(=$NR^A$)$R^A$, —C(=$NR^A$)$OR^A$, —C(=$NR^A$)N($R^A$)$_2$, —C(=O)$R^A$, —C(=O)$OR^A$, —C(=O)N($R^A$)$_2$, —S(=O)$R^A$, —S(=O)$_2R^A$, —$NO_2$, —$NR^A$C(=O)$R^A$, —$NR^A$C(=O)$OR^A$, —$NR^A$C(=O)N($R^A$)$_2$, —$NR^A$S(=O)$R^A$, —$NR^A$S(=O)$_2R^A$, —S(=O)N($R^A$)$_2$, —S(=O)$_2$N($R^A$)$_2$, —OC(=O)$R^A$, —OC(=O)$OR^A$, or —OC(=O)N($R^A$)$_2$;

each occurrence of $R^3$ and $R^4$ is, independently, hydrogen, substituted or unsubstituted alkyl, or a nitrogen protecting group;

each occurrence of $R^A$ is, independently, hydrogen, substituted or unsubstituted acyl, substituted or unsubstituted alkyl, substituted or unsubstituted alkenyl, substituted or unsubstituted alkynyl, substituted or unsubstituted heteroalkyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^A$ groups are joined to form a substituted or unsubstituted heterocyclic ring;

k is 1, 2, 3, 4, 5, or 6; and p is 1, 2, 3, or 4.

In certain embodiments, A is of the formula:

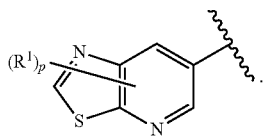

In certain embodiments, A is of the formula:

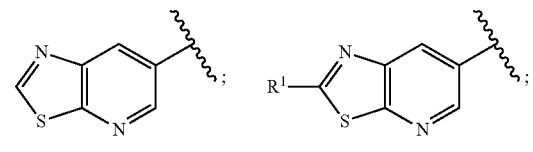

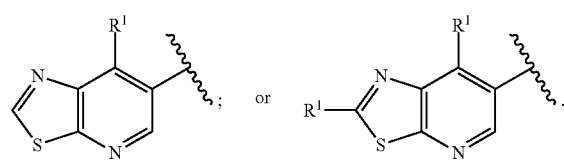

In certain embodiments, A is of the formula:

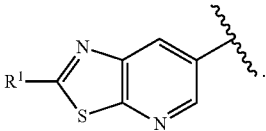

In certain embodiments, A is of the formula:

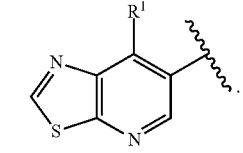

In certain embodiments, A is of the formula:

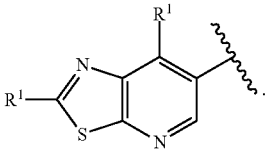

In certain embodiments, A is of the formula:

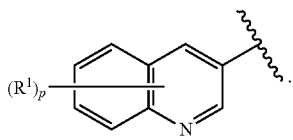

In certain embodiments, A is of the formula:

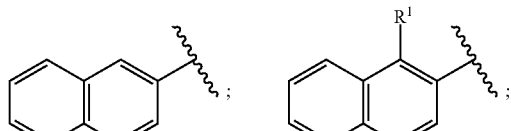

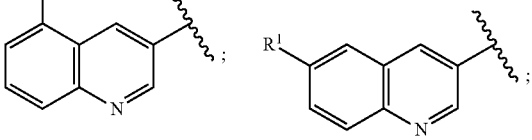

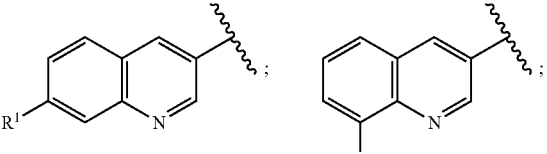

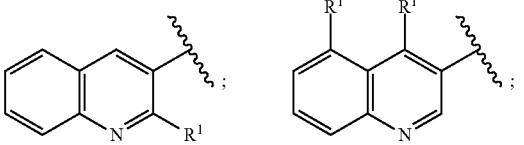

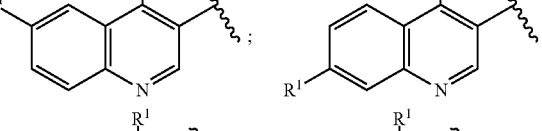

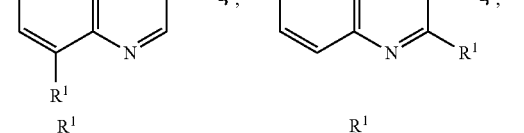

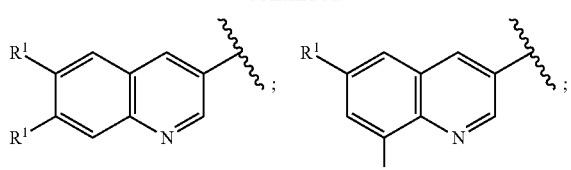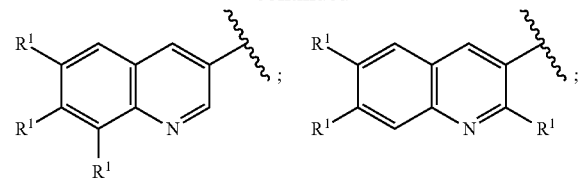

-continued

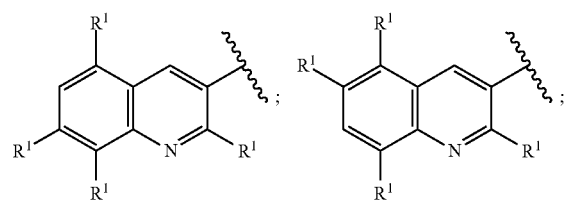

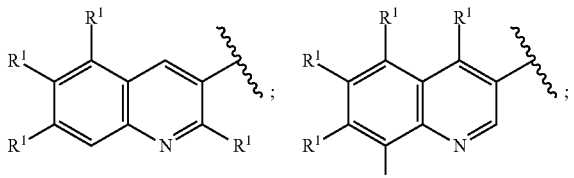

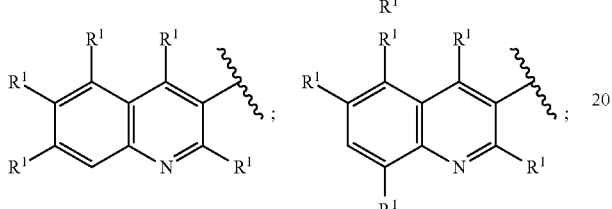

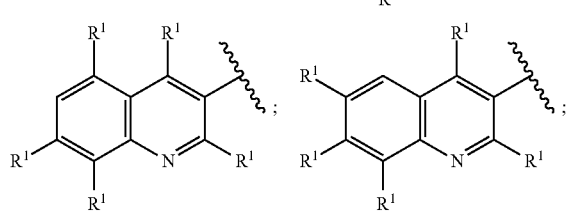

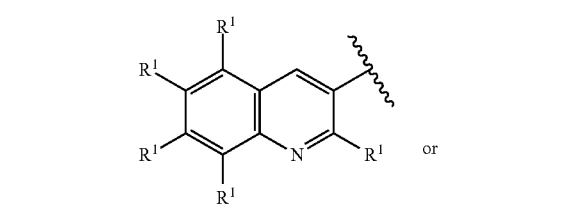

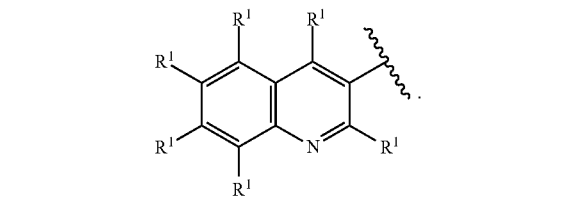

In certain embodiments, A is of the formula:

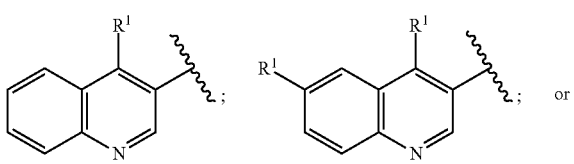

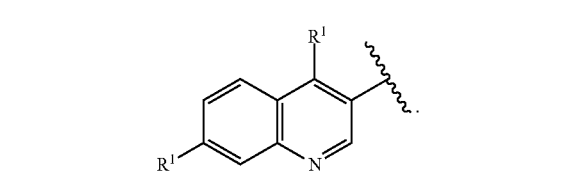

In certain embodiments, A is of the formula:

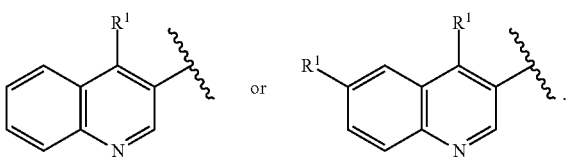

In certain embodiments, A is of the formula:

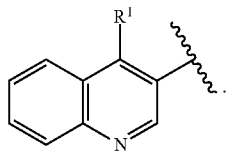

In certain embodiments, A is of the formula:

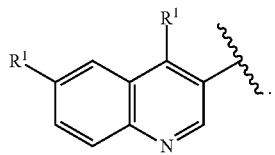

In certain embodiments, A is of the formula:

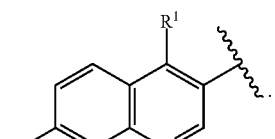

In certain embodiments, A is of the formula:

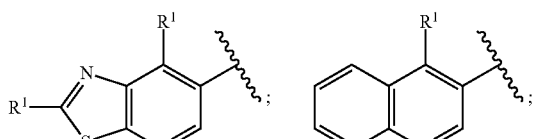

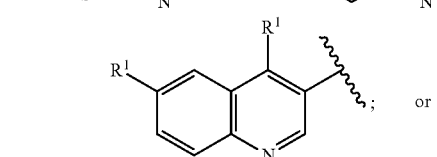

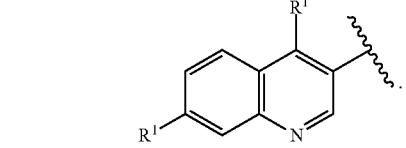

In certain embodiments, each occurrence of $R^1$ is, independently, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted heteroalkyl, —OR$^A$, —N(R$^A$)$_2$, —SR$^A$, —CN, —SCN, —C(=NR$^A$)R$^A$, —C(=NR$^A$)OR$^A$, —C(=NR$^A$)N(R$^A$)$_2$, —C(=O)R$^A$, —C(=O)OR$^A$, —C(=O)N(R$^A$)$_2$, —S(=O) R$^A$, —S(=O)$_2$R$^A$, —NO$_2$, —NR$^A$C(=O)R$^A$, —NR$^A$C (=O)OR$^A$, —NR$^A$C(=O)N(R$^A$)$_2$, —NR$^A$S(=O)R$^A$, —NR$^A$S(=O)$_2$R$^A$, —S(=O)N(R$^A$)$_2$, —S(=O)$_2$N(R$^A$)$_2$, —OC(=O)R$^A$, —OC(=O)OR$^A$, or —OC(=O)N(R$^A$)$_2$.

In certain embodiments, each occurrence of R$^1$ is, independently, halogen, substituted or unsubstituted alkyl, substituted or unsubstituted alkenyl, substituted or unsubstituted alkynyl, substituted or unsubstituted heterocyclyl, substituted or unsubstituted carbocyclyl, substituted or unsubstituted aryl, substituted or unsubstituted heteroaryl, substituted or unsubstituted heteroalkyl, or —OR$^A$.

In certain embodiments, each occurrence of R$^1$ is, independently, halogen, substituted or unsubstituted alkyl, substituted or unsubstituted carbocyclyl, substituted or unsubstituted heteroaryl, substituted or unsubstituted heteroalkyl, or —OR$^A$.

In certain embodiments, each occurrence of R$^1$ is, independently, halogen, unsubstituted C$_{1-6}$ alkyl, C$_{1-6}$ alkoxyalkyl, C$_{1-6}$ hydroxyalkyl, C$_{1-6}$ azidoalkyl, C$_{1-6}$ haloalkyl, unsubstituted 5 or 6-membered monocyclic heteroaryl, unsubstituted C$_{3-6}$ cycloalkyl, or —OC$_{1-6}$ alkyl. In certain embodiments, each occurrence of R$^1$ is halogen, unsubstituted C$_{1-6}$ alkyl, C$_{1-6}$ alkoxyalkyl, C$_{1-6}$ hydroxyalkyl, C$_{1-6}$ azidoalkyl, C$_{1-6}$ haloalkyl, or unsubstituted C$_{3-4}$ cycloalkyl. In certain embodiments, each occurrence of R$^1$ is, independently, halogen, unsubstituted C$_{3-4}$ cycloalkyl, or —OC$_{1-6}$ alkyl.

In certain embodiments, each occurrence of R$^1$ is, independently, —Cl, —Br, —F, —CH$_3$, —CH(CH$_3$)$_2$, —C(CH$_3$)$_2$OCH$_3$, —CH(OCH$_3$)CH$_3$, —CH(OH)CH$_3$, —CH(N$_3$)CH$_3$, —CF$_3$, or unsubstituted cyclopropyl. In certain embodiments, each occurrence of R$^1$ is, independently, —Cl, —Br, —F, —CH$_3$, —CH(CH$_3$)$_2$, —C(CH$_3$)$_2$ OCH$_3$, —C(CH$_3$)$_2$OCH$_2$CH$_3$, —CH(OCH$_3$)CH$_3$, —CH (OCH$_2$CH$_3$)CH$_3$, —CH(OH)CH$_3$, —CH(N$_3$)CH$_3$, —CF$_3$, —N(CH$_3$)$_2$, —N(CH$_3$)(CH$_2$CH$_2$OCH$_3$), —N(CH$_3$)(CH (CH$_3$)CH$_2$OCH$_3$), unsubstituted azetidine, or unsubstituted cyclopropyl.

In certain embodiments, each occurrence of R$^1$ is, independently, —Cl, —Br, —F, unsubstituted cyclopropyl, or —OCH$_3$. In certain embodiments, each occurrence of R$^1$ is, independently, —Cl or —C(CH$_3$)$_2$OCH$_3$.

In certain embodiments, each occurrence of R$^1$ is, independently, halogen, substituted or unsubstituted alkyl, substituted or unsubstituted carbocyclyl, substituted or unsubstituted alkoxyalkyl, or substituted or unsubstituted hydroxyalkyl. In certain embodiments, each occurrence of R$^1$ is, independently, —F, unsubstituted cyclopropyl, methyl, —CH(CH$_3$)OCH$_3$, —CH(CH$_3$)OH, —CH(CH$_3$) OCH$_2$CH$_3$, or —C(CH$_3$)$_2$OCH$_3$.

In certain embodiments, R$^1$ is —CH$_2$CH$_3$, —CH(CH$_3$) OCH$_3$, —C(CH$_3$)$_2$OCH$_3$, or —C(CH$_3$)$_2$OCH$_2$CH$_3$. In certain embodiments, R$^1$ is —CH$_2$OCH$_3$, —CH(CH$_3$)OCH$_3$, —CH(CH$_3$)OCH$_2$CH$_3$, —C(CH$_3$)$_2$OCH$_3$, or —C(CH$_3$)$_2$ OCH$_2$CH$_3$. In certain embodiments, R$^1$ is —C(CH$_3$)$_2$OCH$_3$. In certain embodiments, R$^1$ is —CH(CH$_3$)OCH$_3$. In certain embodiments, R$^1$ is —CH$_2$OH, —CH(CH$_3$)OH, or —C(CH$_3$)$_2$OH. In certain embodiments, R$^1$ is —C(CH$_3$)$_2$OH. In certain embodiments, R$^1$ is —CH(CH$_3$)OH.

In certain embodiments, R$^1$ is optionally substituted cyclopropyl. In certain embodiments, R$^1$ is unsubstituted cyclopropyl. In certain embodiments, R$^1$ is optionally substituted cyclobutyl. In certain embodiments, R$^1$ is unsubstituted cyclobutyl. In certain embodiments, R$^1$ is optionally substituted cyclopentyl. In certain embodiments, R$^1$ is unsubstituted cyclopentyl. In certain embodiments, R$^1$ is optionally substituted cyclohexyl. In certain embodiments, R$^1$ is unsubstituted cyclohexyl.

In certain embodiments, each occurrence of R$^1$ is, independently, substituted or unsubstituted C$_{1-6}$ alkyl. In certain embodiments, R$^1$ is C$_{1-6}$ haloalkyl. In certain embodiments, R$^1$ is C$_{1-4}$ haloalkyl. In certain embodiments, R$^1$ is trifluoromethyl, difluoromethyl, or fluoromethyl. In certain embodiments, R$^1$ is trifluoromethyl or difluoromethyl. In certain embodiments, R$^1$ is trifluoromethyl. In certain embodiments, R$^1$ is C$_{1-6}$ azidoalkyl. In certain embodiments, R$^1$ is —CH(CH$_3$)N$_3$, —C(CH$_3$)$_2$N$_3$, or —CH$_2$N$_3$. In certain embodiments, R$^1$ is —CH(CH$_3$)N$_3$. In certain embodiments, R$^1$ is unsubstituted C$_{1-6}$ alkyl. In certain embodiments, R$^1$ is unsubstituted C$_{1-4}$ alkyl. In certain embodiments, R$^1$ is methyl, ethyl, propyl, butyl, isopropyl, isobutyl, sec-butyl, or tert-butyl. In certain embodiments, R$^1$ is isopropyl.

In certain embodiments, each occurrence of R$^1$ is, independently, —Cl or optionally substituted cyclopropyl. In certain embodiments, each occurrence of R$^1$ is, independently, methyl or optionally substituted cyclopropyl. In certain embodiments, each occurrence of R$^1$ is, independently, —Cl or unsubstituted cyclopropyl. In certain embodiments, each occurrence of R$^1$ is, independently, methyl or unsubstituted cyclopropyl.

In certain embodiments, each occurrence of R$^1$ is, independently, —F or optionally substituted cyclopropyl. In certain embodiments, each occurrence of R$^1$ is, independently, —F or unsubstituted cyclopropyl.

In certain embodiments, each occurrence of R$^1$ is, independently, —OCH$_3$ or optionally substituted cyclopropyl. In certain embodiments, each occurrence of R$^1$ is, independently, —OCH$_3$ or unsubstituted cyclopropyl.

In certain embodiments, each occurrence of R$^1$ is, independently, —Br or optionally substituted C$_{1-6}$ alkyl. In certain embodiments, each occurrence of R$^1$ is, independently, —Br or methyl.

In certain embodiments, each occurrence of R$^1$ is, independently, —Cl, —Br, —F, or —I. In certain embodiments, each occurrence of R$^1$ is, independently, —Cl, —Br, or —F. In certain embodiments, each occurrence of R$^1$ is, independently, —Cl. In certain embodiments, each occurrence of R$^1$ is, independently, —Br. In certain embodiments, each occurrence of R$^1$ is, independently, —F.

In certain embodiments, R$^1$ is —N(R$^A$)$_2$, wherein R$^A$ is, independently, hydrogen, substituted or unsubstituted alkyl, substituted or unsubstituted heteroalkyl, or two R$^A$ groups are joined to form a substituted or unsubstituted heterocyclic ring. In certain embodiments, R$^1$ is —N(R$^{aa}$)$_2$, wherein R$^A$ is, independently, substituted or unsubstituted alkyl, substituted or unsubstituted alkoxyalkyl, or two R$^A$ groups are joined to form a substituted or unsubstituted heterocyclic ring. In certain embodiments, R$^1$ is —N(R$^A$)$_2$, wherein R$^A$ is, independently, unsubstituted alkyl, substituted or unsubstituted alkoxyalkyl, or two R$^A$ groups are joined to form an unsubstituted heterocyclic ring. In certain embodiments, R$^1$ is —N(CH$_3$)$_2$, —N(CH$_3$)(CH$_2$CH$_2$OCH$_3$), —N(CH$_3$)(CH (CH$_3$)CH$_2$OCH$_3$), unsubstituted azetidine In certain embodiments, R$^1$ is substituted or unsubstituted 5-membered heteroaryl. In certain embodiments, R$^1$ is substituted or unsubstituted 5-membered heteroaryl with 1, 2, 3, or 4 heteroatoms selected from the group consisting of N, O, and S. In certain embodiments, R$^1$ is substituted or unsubstituted thiazole. In certain embodiments, R$^1$ is substituted or unsubstituted thiophene. In certain embodiments, $R^1$ is substituted or unsubstituted pyrazole. In certain embodiments, $R^1$ is substituted or unsubstituted imidazole. In certain embodiments, $R^1$ is substituted or unsubstituted pyrrole. In certain embodiments, $R^1$ is substituted or unsubstituted tetrazole. In certain embodiments, $R^1$ is substituted or unsubstituted triazole. In certain embodiments, $R^1$ is substituted or unsubstituted oxadiazole. In certain embodiments, $R^1$ is substituted or unsubstituted thiadiazole. In certain embodiments, $R^1$ is substituted or unsubstituted dithiazole. In certain embodiments, $R^1$ is substituted or unsubstituted oxazole. In certain embodiments, $R^1$ is substituted or unsubstituted isoxazole. In certain embodiments, $R^1$ is substituted or unsubstituted isothiazole. In certain embodiments, $R^1$ is substituted or unsubstituted pyrrole. In certain embodiments, $R^1$ is substituted or unsubstituted furan.

In certain embodiments, A is of the formula:

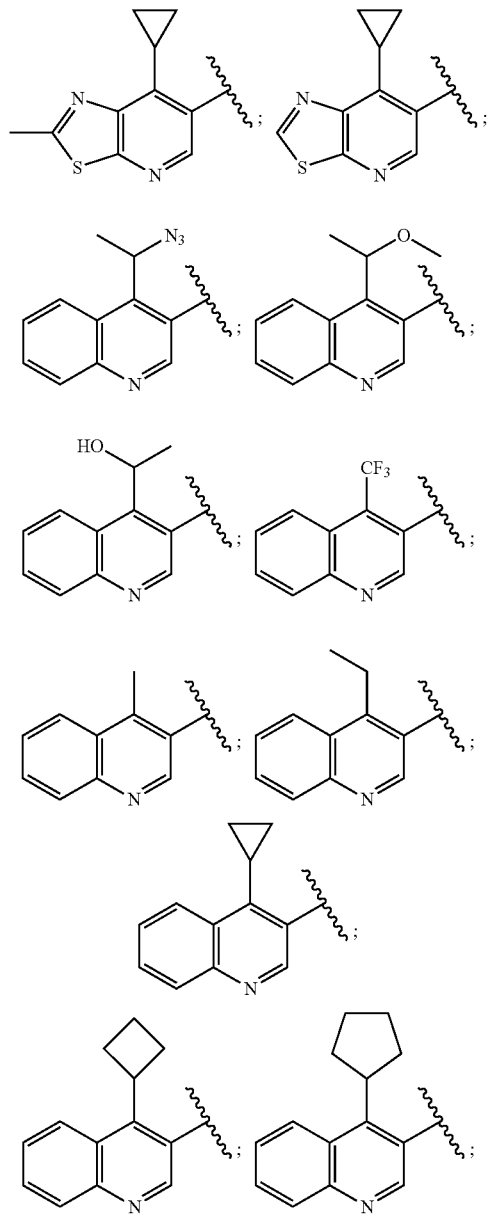

-continued

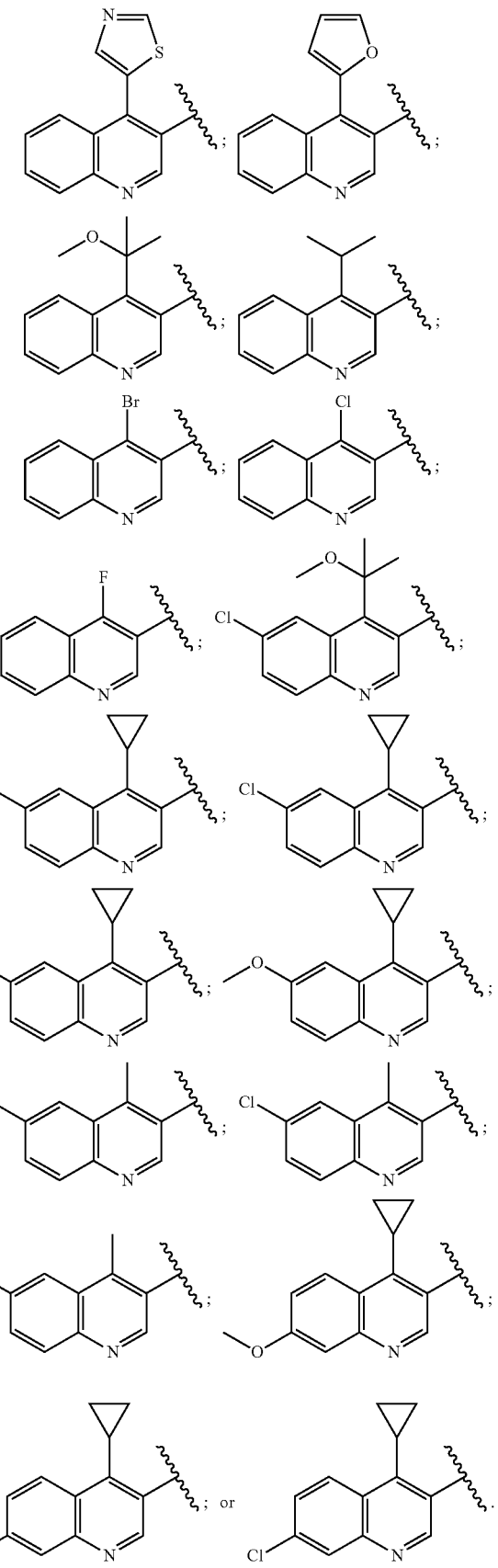

In certain embodiments, A is of the formula:
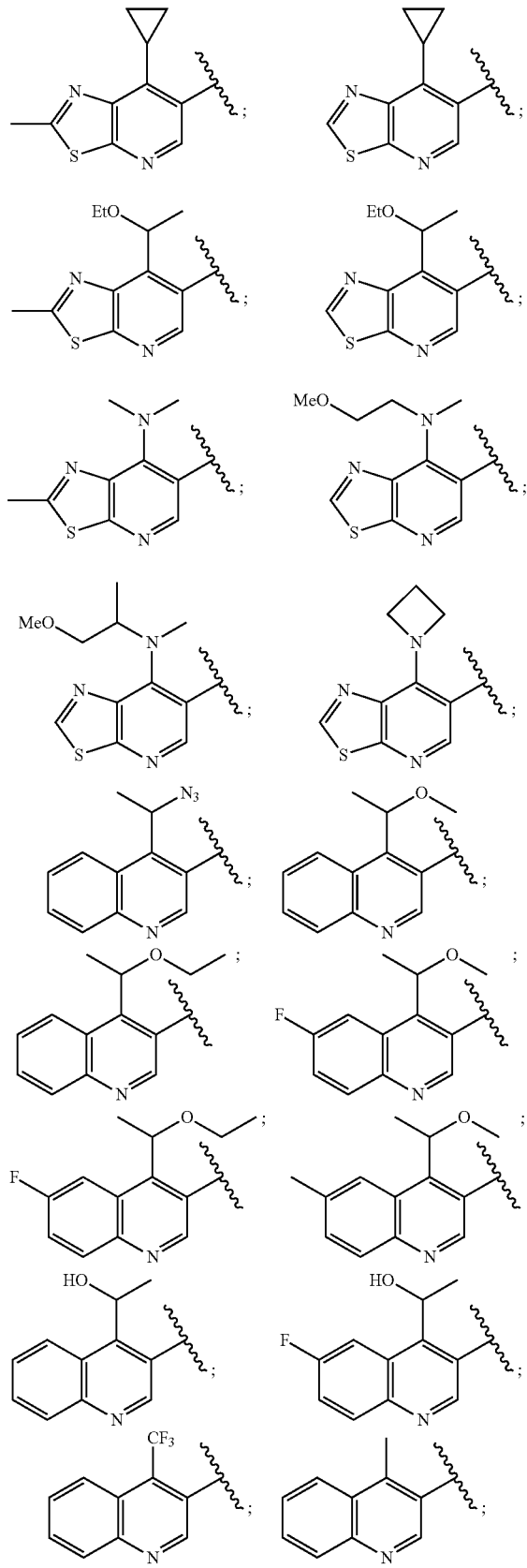
-continued
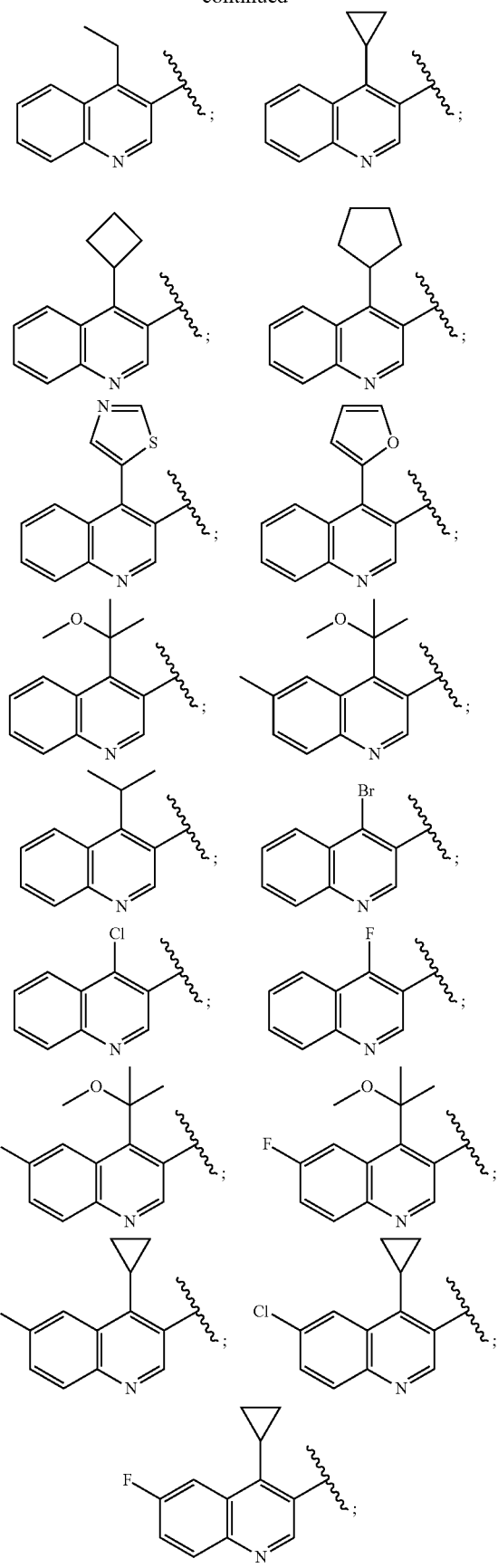

-continued

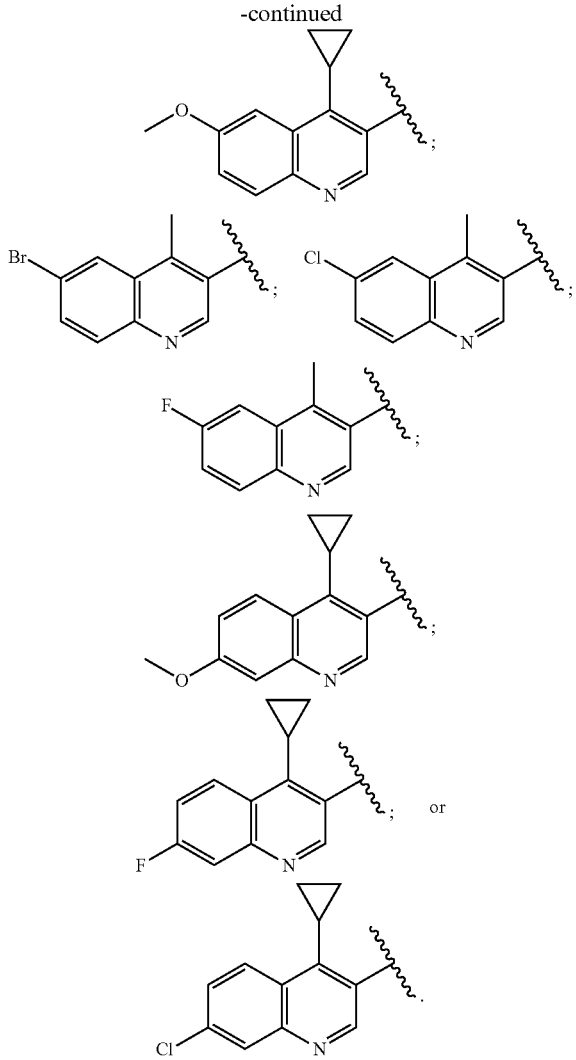

In certain embodiments, B is 2-pyridinyl, 3-pyridinyl, or 4-pyridinyl. In certain embodiments, B is 3-pyridinyl or 4-pyridinyl. In certain embodiments, B is 2-pyridinyl. In certain embodiments, B is 3-pyridinyl. In certain embodiments, B is 4-pyridinyl.

In certain embodiments, B is of the formula:

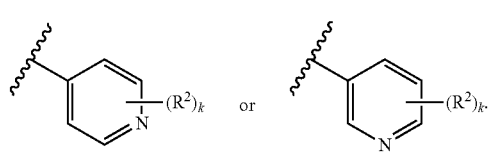

In certain embodiments, B is of the formula:

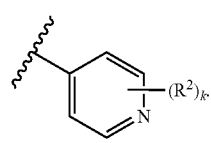

In certain embodiments, B is of the formula:

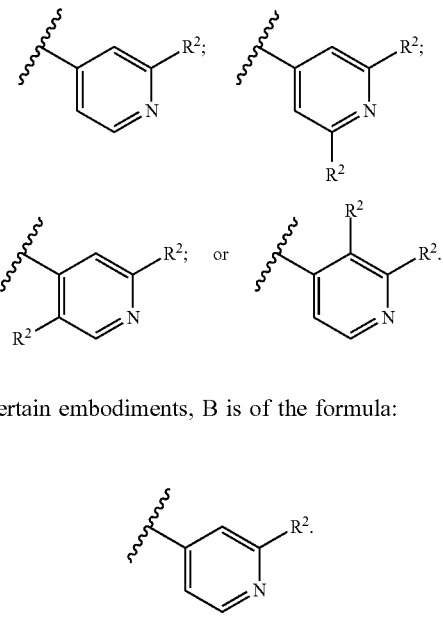

In certain embodiments, B is of the formula:

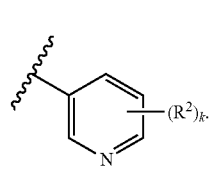

In certain embodiments, B is of the formula:

In certain embodiments, B is of the formula:

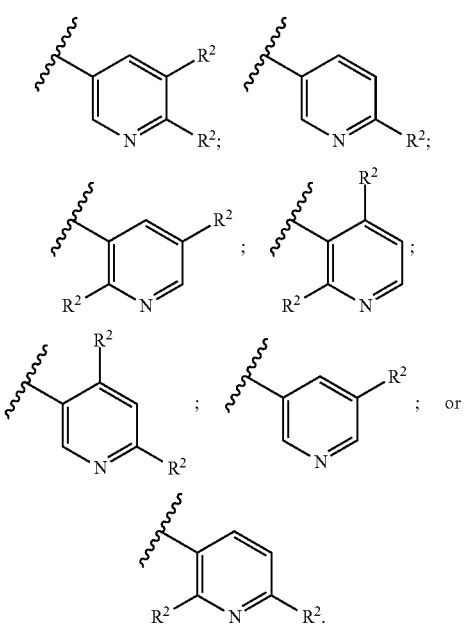

In certain embodiments, B is of the formula:

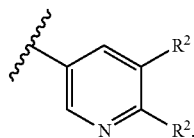

In certain embodiments, B is of the formula:

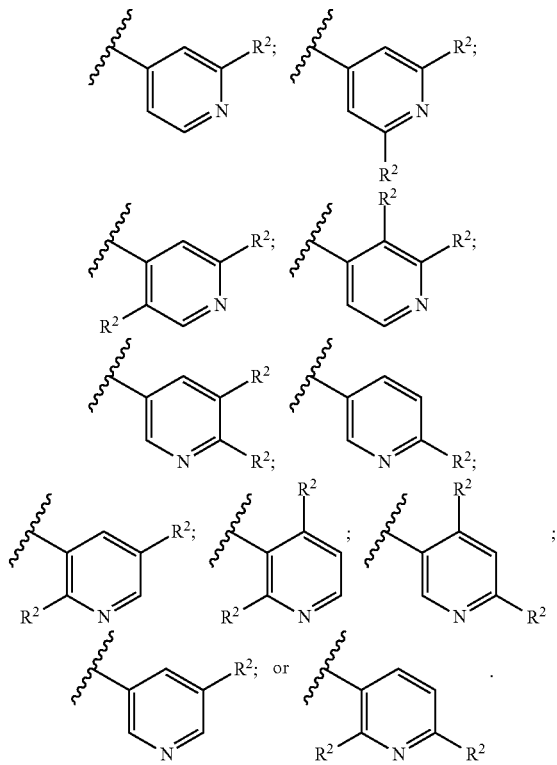

In certain embodiments, B is of the formula:

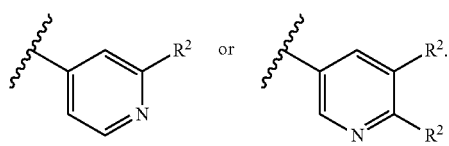

In certain embodiments, each occurrence of $R^2$ is, independently, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted heteroalkyl, —$OR^4$, —$N(R^4)_2$, —$SR^4$, —CN, —SCN, —$C(=NR^4)R^4$, —$C(=NR^4)OR^4$, —$C(=NR^4)N(R^4)_2$, —$C(=O)R^4$, —$C(=O)OR^4$, —$C(=O)N(R^4)_2$, —$S(=O)R^4$, —$S(=O)_2R^4$, —$NO_2$, —$NR^4C(=O)R^4$, —$NR^4C(=O)OR^4$, —$NR^4C(=O)N(R^4)_2$, —$NR^4S(=O)R^4$, —$NR^4S(=O)_2R^4$, —$S(=O)N(R^4)_2$, —$S(=O)_2N(R^4)_2$, —$OC(=O)R^4$, —$OC(=O)OR^4$, or —$OC(=O)N(R^4)_2$.

In certain embodiments, each occurrence of $R^2$ is, independently, halogen, substituted or unsubstituted alkyl, substituted or unsubstituted alkenyl, substituted or unsubstituted alkynyl, substituted or unsubstituted heterocyclyl, substituted or unsubstituted carbocyclyl, substituted or unsubstituted aryl, substituted or unsubstituted heteroaryl, substituted or unsubstituted heteroalkyl, or —$OR^4$.

In certain embodiments, each occurrence of $R^2$ is, independently, halogen, substituted or unsubstituted alkyl, or substituted or unsubstituted heteroaryl. In certain embodiments, each occurrence of $R^2$ is, independently, halogen, $C_{1-6}$ haloalkyl, or unsubstituted 5-membered monocyclic heteroaryl. In certain embodiments, each occurrence of $R^2$ is, independently, halogen or an unsubstituted 5-membered monocyclic heteroaryl ring having 2 or 3 nitrogen atoms in the ring.

In certain embodiments, each occurrence of $R^2$ is, independently, $C_{1-6}$ haloalkyl. In certain embodiments, each occurrence of $R^2$ is, independently, $C_{1-4}$ haloalkyl. In certain embodiments, $R^2$ is trifluoromethyl, difluoromethyl, or fluoromethyl. In certain embodiments, $R^2$ is trifluoromethyl or difluoromethyl. In certain embodiments, $R^2$ is trifluoromethyl.

In certain embodiments, each occurrence of $R^2$ is, independently, —Cl, —Br, —F, —I, or an unsubstituted 5-membered monocyclic heteroaryl ring having 2 or 3 nitrogen atoms in the ring. In certain embodiments, each occurrence of $R^2$ is, independently, —Cl, —Br, —F, or an unsubstituted 5-membered monocyclic heteroaryl ring having 2 or 3 nitrogen atoms in the ring. In certain embodiments, each occurrence of $R^2$ is, independently, —Cl or an unsubstituted 5-membered monocyclic heteroaryl ring having 2 or 3 nitrogen atoms in the ring. In certain embodiments, each occurrence of $R^2$ is, independently, —Br or an unsubstituted 5-membered monocyclic heteroaryl ring having 2 or 3 nitrogen atoms in the ring. In certain embodiments, each occurrence of $R^2$ is, independently, —F or an unsubstituted 5-membered monocyclic heteroaryl ring having 2 or 3 nitrogen atoms in the ring.

In certain embodiments, each occurrence of $R^2$ is, independently, F, Cl, Br,

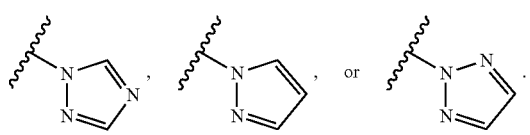 [SMILES: *n1cncn1 ; *n1cccn1 ; *n1nccn1]

In certain embodiments, each occurrence of $R^2$ is, independently, Cl, Br, or

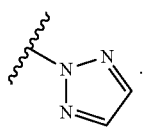

In certain embodiments, each occurrence of $R^3$ is, independently, Cl or

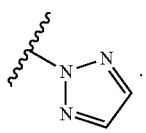

In certain embodiments, each occurrence of $R^1$ is, independently, halogen, unsubstituted $C_{1-6}$ alkyl, $C_{1-6}$ alkoxyalkyl, $C_{1-6}$ hydroxyalkyl, $C_{1-6}$ azidoalkyl, $C_{1-6}$ haloalkyl, unsubstituted 5 or 6-membered monocyclic heteroaryl, unsubstituted $C_{3-6}$ cycloalkyl, or —$OC_{1-6}$ alkyl; and each occurrence of $R^2$ is, independently, Cl or

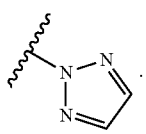

In certain embodiments, B is of the formula:

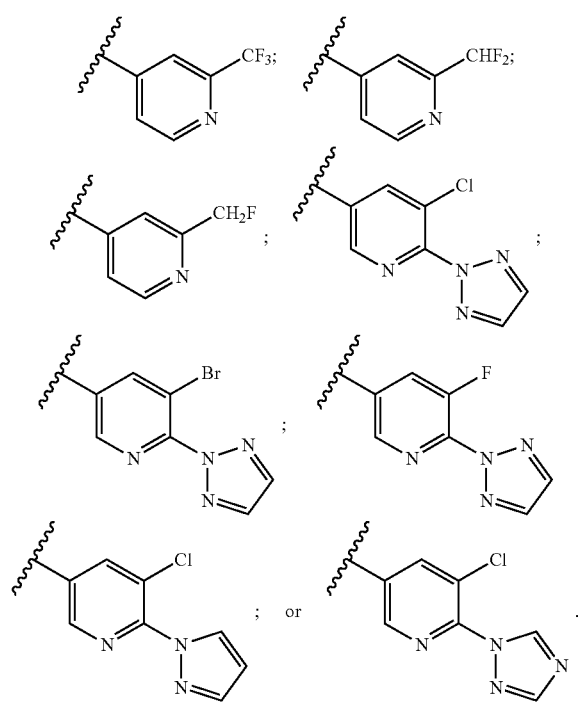

In certain embodiments, $R^3$ is hydrogen, substituted or unsubstituted alkyl, or a nitrogen protecting group. In certain embodiments, $R^3$ is hydrogen, substituted or unsubstituted $C_{1-6}$ alkyl, or a nitrogen protecting group. In certain embodiments, $R^3$ is hydrogen, substituted or unsubstituted $C_{1-4}$ alkyl, or a nitrogen protecting group. In certain embodiments, $R^3$ is hydrogen, unsubstituted $C_{1-4}$ alkyl, or a nitrogen protecting group. In certain embodiments, $R^3$ is hydrogen.

In certain embodiments, $R^4$ is hydrogen, substituted or unsubstituted alkyl, or a nitrogen protecting group. In certain embodiments, $R^4$ is hydrogen, substituted or unsubstituted $C_{1-6}$ alkyl, or a nitrogen protecting group. In certain embodiments, $R^4$ is hydrogen, substituted or unsubstituted $C_{1-4}$ alkyl, or a nitrogen protecting group. In certain embodiments, $R^4$ is hydrogen, unsubstituted $C_{1-4}$ alkyl, or a nitrogen protecting group. In certain embodiments, $R^4$ is hydrogen.

In certain embodiments, $R^3$ and $R^4$ are both hydrogen.

In certain embodiments, $R^A$ is, independently, hydrogen, substituted or unsubstituted acyl, substituted or unsubstituted alkyl, substituted or unsubstituted alkenyl, substituted or unsubstituted alkynyl, substituted or unsubstituted heteroalkyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^A$ groups are joined to form a substituted or unsubstituted heterocyclic ring. In certain embodiments, $R^A$ is, independently, hydrogen, substituted or unsubstituted alkyl, substituted or unsubstituted heteroalkyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or two $R^A$ groups are joined to form a substituted or unsubstituted heterocyclic ring. In certain embodiments, $R^A$ is, independently, hydrogen, substituted or unsubstituted alkyl, substituted or unsubstituted heteroalkyl, substituted or unsubstituted heterocyclyl, substituted or unsubstituted aryl, substituted or unsubstituted heteroaryl, or two $R^A$ groups are joined to form a substituted or unsubstituted heterocyclic ring. In certain embodiments, $R^A$ is, independently, hydrogen, substituted or unsubstituted $C_{1-6}$ alkyl, substituted or unsubstituted heteroalkyl, substituted or unsubstituted 5-6 membered heterocyclyl, substituted or unsubstituted phenyl, substituted or unsubstituted 5-6 membered heteroaryl, or two $R^A$ groups are joined to form a substituted or unsubstituted heterocyclic ring. In certain embodiments, $R^A$ is, independently, hydrogen, substituted or unsubstituted $C_{1-6}$ alkyl, substituted or unsubstituted $C_{1-10}$ heteroalkyl, substituted or unsubstituted 5-6 membered heterocyclyl, substituted or unsubstituted phenyl, substituted or unsubstituted 5-6 membered heteroaryl, or two $R^A$ groups are joined to form a substituted or unsubstituted heterocyclic ring. In certain embodiments, $R^A$ is, independently, hydrogen or substituted or unsubstituted $C_{1-6}$ alkyl. In certain embodiments, $R^A$ is, independently, hydrogen or unsubstituted $C_{1-6}$ alkyl.

In certain embodiments, k is 0, 1, 2, 3, or 4. In certain embodiments, k is 0, 1, 2, or 3. In certain embodiments, k is 0, 1, or 2. In certain embodiments, k is 0 or 1. In certain embodiments, k is 1 or 2.

In certain embodiments, p is 0, 1, 2, 3, or 4. In certain embodiments, p is 0, 1, 2, or 3. In certain embodiments, p is 0, 1, or 2. In certain embodiments, p is 0 or 1. In certain embodiments, p is 1 or 2.

In certain embodiments, k is 0, 1, or 2; and p is 0, 1, or 2. In certain embodiments, k is 1 or 2; and p is 0 or 1. In certain embodiments, k is 0 or 1; and p is 1 or 2. In certain embodiments, k is 1 or 2; and p is 1 or 2. In certain embodiments, k is 1; and p is 2. In certain embodiments, k is 2; and p is 1. In certain embodiments, k is 2; and p is 2. In certain embodiments, k is 1; and p is 1.

In certain embodiments, the compound of Formula I is a compound of Formula I-a:

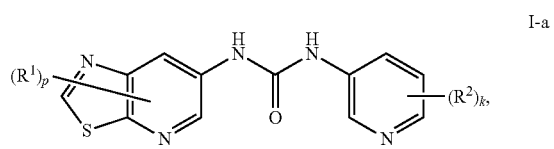

I-a or a pharmaceutically acceptable salt, co-crystal, tautomer, stereoisomer, solvate, hydrate, polymorph, isotopically enriched derivative, or prodrug thereof.

In certain embodiments of Formula I-a, each occurrence of $R^1$ is, independently, unsubstituted $C_{1-6}$ alkyl or unsubstituted $C_{3-6}$ cycloalkyl.

In certain embodiments of Formula I-a, each occurrence of $R^1$ is, independently, unsubstituted $C_{1-6}$ alkyl or substituted or unsubstituted $C_{2-6}$ alkoxyalkyl.

In certain embodiments of Formula I-a, each occurrence of $R^2$ is, independently, halogen or an unsubstituted 5-membered monocyclic heteroaryl ring having 2 or 3 nitrogen atoms in the ring.

In certain embodiments of Formula I-a, each occurrence of $R^1$ is, independently, unsubstituted $C_{1-6}$ alkyl or unsubstituted $C_{3-6}$ cycloalkyl; and each occurrence of $R^2$ is, independently, halogen or an unsubstituted 5-membered monocyclic heteroaryl ring having 2 or 3 nitrogen atoms in the ring.

In certain embodiments of Formula I-a, each occurrence of $R^1$ is, independently, unsubstituted $C_{1-6}$ alkyl or substituted or unsubstituted $C_{2-6}$ alkoxyalkyl; and each occurrence of $R^2$ is, independently, halogen or an unsubstituted 5-membered monocyclic heteroaryl ring having 2 or 3 nitrogen atoms in the ring.

In certain embodiments, the compound of Formula I is a compound of Formula I-b:

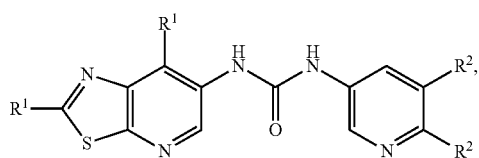

or a pharmaceutically acceptable salt, co-crystal, tautomer, stereoisomer, solvate, hydrate, polymorph, isotopically enriched derivative, or prodrug thereof.

In certain embodiments of Formula I-b, each occurrence of $R^1$ is, independently, unsubstituted $C_{1-6}$ alkyl or unsubstituted $C_{3-6}$ cycloalkyl.

In certain embodiments of Formula I-b, each occurrence of $R^1$ is, independently, unsubstituted $C_{1-6}$ alkyl or unsubstituted cyclopropyl.

In certain embodiments of Formula I-b, each occurrence of $R^1$ is, independently, unsubstituted $C_{1-6}$ alkyl or substituted or unsubstituted $C_{2-6}$ alkoxyalkyl.

In certain embodiments of Formula I-b, each occurrence of $R^2$ is, independently, halogen or an unsubstituted 5-membered monocyclic heteroaryl ring having 2 or 3 nitrogen atoms in the ring.

In certain embodiments of Formula I-b, each occurrence of $R^1$ is, independently, unsubstituted $C_{1-6}$ alkyl or unsubstituted $C_{3-6}$ cycloalkyl; and each occurrence of $R^2$ is, independently, halogen or an unsubstituted 5-membered monocyclic heteroaryl ring having 2 or 3 nitrogen atoms in the ring.

In certain embodiments of Formula I-b, each occurrence of $R^1$ is, independently, unsubstituted $C_{1-6}$ alkyl or substituted or unsubstituted $C_{2-6}$ alkoxyalkyl; and each occurrence of $R^2$ is, independently, halogen or an unsubstituted 5-membered monocyclic heteroaryl ring having 2 or 3 nitrogen atoms in the ring.

In certain embodiments, the compound of Formula I is a compound of Formula I-c:

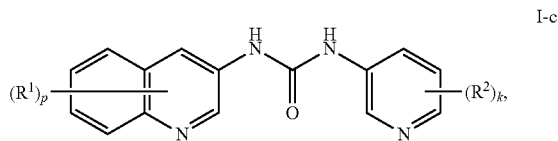

or a pharmaceutically acceptable salt, co-crystal, tautomer, stereoisomer, solvate, hydrate, polymorph, isotopically enriched derivative, or prodrug thereof.

In certain embodiments of Formula I-c, each occurrence of $R^1$ is halogen, unsubstituted $C_{1-6}$ alkyl, $C_{1-6}$ alkoxyalkyl, $C_{1-6}$ hydroxyalkyl, $C_{1-6}$ azidoalkyl, $C_{1-6}$ haloalkyl, or unsubstituted $C_{3-4}$ cycloalkyl.

In certain embodiments of Formula I-c, each occurrence of $R^2$ is, independently, halogen or an unsubstituted 5-membered monocyclic heteroaryl ring having 2 or 3 nitrogen atoms in the ring.

In certain embodiments of Formula I-c, each occurrence of $R^1$ is halogen, unsubstituted $C_{1-6}$ alkyl, $C_{1-6}$ alkoxyalkyl, $C_{1-6}$ hydroxyalkyl, $C_{1-6}$ azidoalkyl, $C_{1-6}$ haloalkyl, or unsubstituted $C_{3-4}$ cycloalkyl; and each occurrence of $R^2$ is, independently, halogen or an unsubstituted 5-membered monocyclic heteroaryl ring having 2 or 3 nitrogen atoms in the ring.

In certain embodiments of Formula I-c, each occurrence of $R^1$ is halogen, unsubstituted $C_{1-6}$ alkyl, $C_{2-6}$ alkoxyalkyl, $C_{1-6}$ hydroxyalkyl, or unsubstituted $C_{3-4}$ cycloalkyl; and each occurrence of $R^2$ is, independently, halogen or an unsubstituted 5-membered monocyclic heteroaryl ring having 2 or 3 nitrogen atoms in the ring.

In certain embodiments, the compound of Formula I is a compound of Formula I-d:

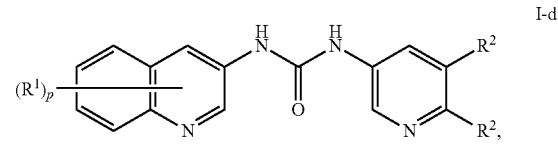

or a pharmaceutically acceptable salt, co-crystal, tautomer, stereoisomer, solvate, hydrate, polymorph, isotopically enriched derivative, or prodrug thereof.

In certain embodiments of Formula I-d, each occurrence of $R^1$ is halogen, unsubstituted $C_{1-6}$ alkyl, $C_{1-6}$ alkoxyalkyl, $C_{1-6}$ hydroxyalkyl, $C_{1-6}$ azidoalkyl, $C_{1-6}$ haloalkyl, or unsubstituted $C_{3-4}$ cycloalkyl.

In certain embodiments of Formula I-c, each occurrence of $R^1$ is halogen, unsubstituted $C_{1-6}$ alkyl, $C_{2-6}$ alkoxyalkyl, $C_{1-6}$ hydroxyalkyl, or unsubstituted $C_{3-4}$ cycloalkyl.

In certain embodiments of Formula I-d, each occurrence of $R^2$ is, independently, halogen or an unsubstituted 5-membered monocyclic heteroaryl ring having 2 or 3 nitrogen atoms in the ring.

In certain embodiments of Formula I-d, each occurrence of $R^1$ is halogen, unsubstituted $C_{1-6}$ alkyl, $C_{1-6}$ alkoxyalkyl, $C_{1-6}$ hydroxyalkyl, $C_{1-6}$ azidoalkyl, $C_{1-6}$ haloalkyl, or unsubstituted $C_{3-4}$ cycloalkyl; and each occurrence of $R^2$ is, independently, halogen or an unsubstituted 5-membered monocyclic heteroaryl ring having 2 or 3 nitrogen atoms in the ring.

In certain embodiments of Formula I-d, each occurrence of $R^1$ is halogen, unsubstituted $C_{1-6}$ alkyl, $C_{2-6}$ alkoxyalkyl, $C_{1-6}$ hydroxyalkyl, or unsubstituted $C_{3-4}$ cycloalkyl; and each occurrence of $R^2$ is, independently, halogen or an unsubstituted 5-membered monocyclic heteroaryl ring having 2 or 3 nitrogen atoms in the ring.

In certain embodiments, the compound of Formula I is a compound of Formula I-e:

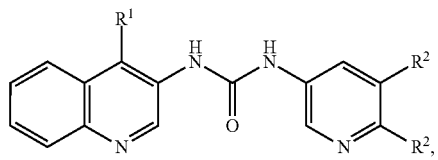

I-e or a pharmaceutically acceptable salt, co-crystal, tautomer, stereoisomer, solvate, hydrate, polymorph, isotopically enriched derivative, or prodrug thereof.

In certain embodiments of Formula I-e, each occurrence of $R^1$ is halogen, unsubstituted $C_{1-6}$ alkyl, $C_{1-6}$ alkoxyalkyl, $C_{1-6}$ hydroxyalkyl, $C_{1-6}$ azidoalkyl, $C_{1-6}$ haloalkyl, or unsubstituted $C_{3-4}$ cycloalkyl.

In certain embodiments of Formula I-e, $R^1$ is $C_{2-6}$ alkoxyalkyl, $C_{1-6}$ hydroxyalkyl, or unsubstituted $C_{3-4}$ cycloalkyl.

In certain embodiments of Formula I-e, each occurrence of $R^2$ is, independently, halogen or an unsubstituted 5-membered monocyclic heteroaryl ring having 2 or 3 nitrogen atoms in the ring.

In certain embodiments of Formula I-e, each occurrence of $R^1$ is halogen, unsubstituted $C_{1-6}$ alkyl, $C_{1-6}$ alkoxyalkyl, $C_{1-6}$ hydroxyalkyl, $C_{1-6}$ azidoalkyl, $C_{1-6}$ haloalkyl, or unsubstituted $C_{3-4}$ cycloalkyl; and each occurrence of $R^2$ is, independently, halogen or an unsubstituted 5-membered monocyclic heteroaryl ring having 2 or 3 nitrogen atoms in the ring.

In certain embodiments of Formula I-e, $R^1$ is $C_{2-6}$ alkoxyalkyl, $C_{1-6}$ hydroxyalkyl, or unsubstituted $C_{3-4}$ cycloalkyl; and each occurrence of $R^2$ is, independently, halogen or an unsubstituted 5-membered monocyclic heteroaryl ring having 2 or 3 nitrogen atoms in the ring.

In certain embodiments, the compound of Formula I is a compound of Formula I-f:

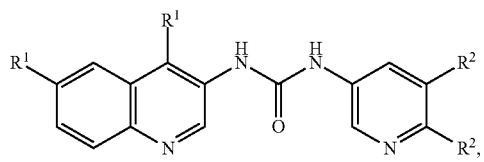

I-f or a pharmaceutically acceptable salt, co-crystal, tautomer, stereoisomer, solvate, hydrate, polymorph, isotopically enriched derivative, or prodrug thereof.

In certain embodiments of Formula I-f, each occurrence of $R^1$ is, independently, halogen, unsubstituted $C_{3-4}$ cycloalkyl, or —$OC_{1-6}$ alkyl.

In certain embodiments of Formula I-f, each occurrence of $R^1$ is halogen, unsubstituted $C_{1-6}$ alkyl, $C_{2-6}$ alkoxyalkyl, $C_{1-6}$ hydroxyalkyl, or unsubstituted $C_{3-4}$ cycloalkyl.

In certain embodiments of Formula I-f, each occurrence of $R^2$ is, independently, halogen or an unsubstituted 5-membered monocyclic heteroaryl ring having 2 or 3 nitrogen atoms in the ring.

In certain embodiments of Formula I-f, each occurrence of $R^1$ is, independently, halogen, unsubstituted $C_{3-4}$ cycloalkyl, or —$OC_{1-6}$ alkyl; and each occurrence of $R^2$ is, independently, halogen or an unsubstituted 5-membered monocyclic heteroaryl ring having 2 or 3 nitrogen atoms in the ring.

In certain embodiments of Formula I-f, each occurrence of $R^1$ is halogen, unsubstituted $C_{1-6}$ alkyl, $C_{2-6}$ alkoxyalkyl, $C_{1-6}$ hydroxyalkyl, or unsubstituted $C_{3-4}$ cycloalkyl; and each occurrence of $R^2$ is, independently, halogen or an unsubstituted 5-membered monocyclic heteroaryl ring having 2 or 3 nitrogen atoms in the ring.

In certain embodiments, the compound of Formula I is a compound of Formula I-g:

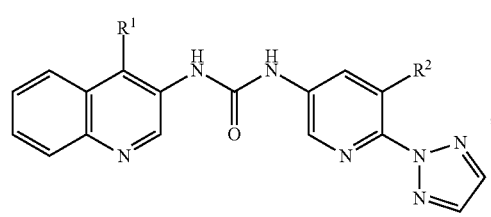

I-g or a pharmaceutically acceptable salt, co-crystal, tautomer, stereoisomer, solvate, hydrate, polymorph, isotopically enriched derivative, or prodrug thereof.

In certain embodiments of Formula I-g, $R^1$ is halogen, unsubstituted $C_{1-6}$ alkyl, $C_{1-6}$ alkoxyalkyl, $C_{1-6}$ hydroxyalkyl, $C_{1-6}$ azidoalkyl, $C_{1-6}$ haloalkyl, or unsubstituted $C_{3-4}$ cycloalkyl.

In certain embodiments, $R^1$ is —$C_1$, —F, —Br, —$CH_3$, —$CH(CH_3)_2$, —$C(CH_3)_2OCH_3$, —$CH(OCH_3)CH_3$, —$CH(OH)CH_3$, —$CH(N_3)CH_3$, $CF_3$, or unsubstituted cyclopropyl.

In certain embodiments of Formula I-g, $R^1$ is $C_{2-6}$ alkoxyalkyl, $C_{1-6}$ hydroxyalkyl, or unsubstituted $C_{3-4}$ cycloalkyl. In certain embodiments of Formula I-g, $R^1$ is —$C(CH_3)_2OCH_3$, —$CH(OCH_3)CH_3$, —$CH(OH)CH_3$, —$CH(OCH_2CH_3)CH_3$, or unsubstituted cyclopropyl.

In certain embodiments of Formula I-g, $R^2$ is halogen. In certain embodiments, $R^2$ is —Cl, —Br, or —F. In certain embodiments, $R^2$ is —Cl.

In certain embodiments of Formula I-g, $R^1$ is halogen, unsubstituted $C_{1-6}$ alkyl, $C_{1-6}$ alkoxyalkyl, $C_{1-6}$ hydroxyalkyl, $C_{1-6}$ azidoalkyl, $C_{1-6}$ haloalkyl, or unsubstituted $C_{3-4}$ cycloalkyl; and $R^2$ is halogen. In certain embodiments of Formula I-g, $R^1$ is —$C_1$, —F, —Br, —$CH_3$, —$CH(CH_3)_2$, —$C(CH_3)_2OCH_3$, —$CH(OCH_3)CH_3$, —$CH(OH)CH_3$, —$CH(N_3)CH_3$, $CF_3$, or unsubstituted cyclopropyl; and $R^2$ is —Cl. In certain embodiments of Formula I-g, $R^1$ is —Br, —$CH_3$, —$CH(CH_3)_2$, —$C(CH_3)_2OCH_3$, —$CH(OCH_3)CH_3$, —$CH(OH)CH_3$, —$CH(N_3)CH_3$, $CF_3$, or unsubstituted cyclopropyl; and $R^2$ is —Cl.

In certain embodiments of Formula I-g, $R^1$ is $R^1$ is $C_{2-6}$ alkoxyalkyl, $C_{1-6}$ hydroxyalkyl, or unsubstituted $C_{3-4}$ cycloalkyl; and $R^2$ is halogen. In certain embodiments of Formula I-g, $R^1$ is —$C(CH_3)_2OCH_3$, —$CH(OCH_3)CH_3$, —$CH(OH)CH_3$, —$CH(OCH_2CH_3)CH_3$, or unsubstituted cyclopropyl; and $R^2$ is —Cl.

In certain embodiments, the compound of Formula I is a compound of Formula I-h:

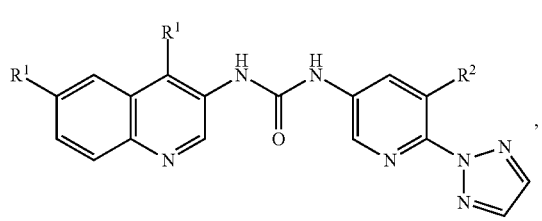

I-h or a pharmaceutically acceptable salt, co-crystal, tautomer, stereoisomer, solvate, hydrate, polymorph, isotopically enriched derivative, or prodrug thereof.

In certain embodiments of Formula I-h, each occurrence of $R^1$ is, independently, halogen, unsubstituted $C_{3-4}$ cycloalkyl, or —$OC_{1-6}$ alkyl. In certain embodiments of Formula I-h, each occurrence of $R^1$ is, independently, —Cl, —Br, —F, unsubstituted cyclopropyl, or —$OCH_3$.

In certain embodiments of Formula I-h, each occurrence of $R^1$ is halogen, unsubstituted $C_{1-6}$ alkyl, $C_{2-6}$ alkoxyalkyl, $C_{1-6}$ hydroxyalkyl, or unsubstituted $C_{3-4}$ cycloalkyl. In certain embodiments of Formula I-h, $R^1$ is —F, methyl, —$C(CH_3)_2OCH_3$, —$CH(OCH_3)CH_3$, —$CH(OH)CH_3$, —$CH(OCH_2CH_3)CH_3$, or unsubstituted cyclopropyl.

In certain embodiments of Formula I-h, $R^2$ is halogen. In certain embodiments of Formula I-h, $R^2$ is —Cl, —Br, or —F. In certain embodiments, $R^2$ is —Cl.

In certain embodiments of Formula I-h, each occurrence of $R^1$ is, independently, halogen, unsubstituted $C_{3-4}$ cycloalkyl, or —$OC_{1-6}$ alkyl; and $R^2$ is halogen. In certain embodiments of Formula I-h, each occurrence of $R^1$ is, independently, —Cl, —Br, —F, unsubstituted cyclopropyl, or —$OCH_3$; and $R^2$ is halogen. In certain embodiments of Formula I-h, each occurrence of $R^1$ is, independently, —Cl, —Br, —F, unsubstituted cyclopropyl, or —$OCH_3$; and $R^2$ is —Cl.

In certain embodiments of Formula I-h, each occurrence of $R^1$ is halogen, unsubstituted $C_{1-6}$ alkyl, $C_{2-6}$ alkoxyalkyl, $C_{1-6}$ hydroxyalkyl, or unsubstituted $C_{3-4}$ cycloalkyl; and $R^2$ is halogen. In certain embodiments of Formula I-h, $R^1$ is —F, methyl, —$C(CH_3)_2OCH_3$, —$CH(OCH_3)CH_3$, —$CH(OH)CH_3$, —$CH(OCH_2CH_3)CH_3$, or unsubstituted cyclopropyl; and $R^2$ is —Cl.

In certain embodiments, the compound of Formula I is a compound of Formula I-i:

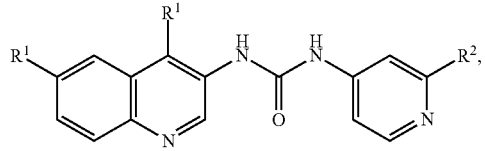

I-i or a pharmaceutically acceptable salt, co-crystal, tautomer, stereoisomer, solvate, hydrate, polymorph, isotopically enriched derivative, or prodrug thereof.

In certain embodiments of Formula I-i, $R^1$ is halogen, unsubstituted $C_{1-6}$ alkyl, $C_{1-6}$ alkoxyalkyl, $C_{1-6}$ hydroxyalkyl, $C_{1-6}$ azidoalkyl, $C_{1-6}$ haloalkyl, —$OC_{1-6}$ alkyl, or unsubstituted $C_{3-4}$ cycloalkyl. In certain embodiments of Formula I-i, each occurrence of $R^1$ is, independently, halogen, unsubstituted $C_{3-4}$ cycloalkyl, $C_{1-6}$ alkoxyalkyl, or —$OC_{1-6}$ alkyl. In certain embodiments of Formula I-i, each occurrence of $R^1$ is, independently, —Cl, —Br, —F, unsubstituted cyclopropyl, —$CH(OCH_3)CH_3$, or —$OCH_3$.

In certain embodiments of Formula I-i, $R^2$ is halogen or $C_{1-6}$ haloalkyl. In certain embodiments of Formula I-i, $R^2$ is —Cl, —Br, or —F. In certain embodiments of Formula I-i, $R^2$ is trifluoromethyl, difluoromethyl, or fluoromethyl. In certain embodiments of Formula I-i, $R^2$ is trifluoromethyl or difluoromethyl. In certain embodiments of Formula I-i, $R^2$ is trifluoromethyl.

In certain embodiments of Formula I-i, $R^1$ is halogen, unsubstituted $C_{1-6}$ alkyl, $C_{1-6}$ alkoxyalkyl, $C_{1-6}$ hydroxyalkyl, $C_{1-6}$ azidoalkyl, $C_{1-6}$ haloalkyl, —$OC_{1-6}$ alkyl, or unsubstituted $C_{3-4}$ cycloalkyl; and $R^2$ is halogen or $C_{1-6}$ haloalkyl. In certain embodiments of Formula I-i, each occurrence of $R^1$ is, independently, halogen, unsubstituted $C_{3-4}$ cycloalkyl, $C_{1-6}$ alkoxyalkyl, or —$OC_{1-6}$ alkyl; and $R^2$ is —Cl, —Br, or —F. In certain embodiments of Formula I-i, each occurrence of $R^1$ is, independently, —Cl, —Br, —F, unsubstituted cyclopropyl, —$CH(OCH_3)CH_3$, or —$OCH_3$; and $R^2$ is trifluoromethyl, difluoromethyl, or fluoromethyl. In certain embodiments of Formula I-i, each occurrence of $R^1$ is, independently, —Cl, —Br, —F, unsubstituted cyclopropyl, —$CH(OCH_3)CH_3$, or —$OCH_3$; and $R^2$ is trifluoromethyl.

In certain embodiments, the compound of Formula I is a compound of Formula I-j:

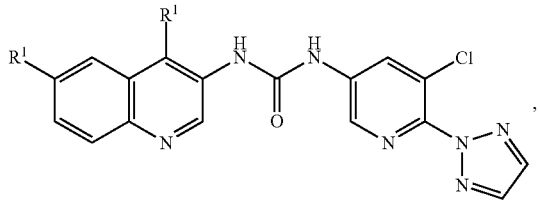

I-j or a pharmaceutically acceptable salt, co-crystal, tautomer, stereoisomer, solvate, hydrate, polymorph, isotopically enriched derivative, or prodrug thereof.

In certain embodiments of Formula I-j, each occurrence of $R^1$ is, independently, halogen, unsubstituted $C_{3-4}$ cycloalkyl, or —$OC_{1-6}$ alkyl. In certain embodiments of Formula I-j, each occurrence of $R^1$ is, independently, —Cl, —Br, —F, unsubstituted cyclopropyl, or —$OCH_3$.

In certain embodiments of Formula I-j, each occurrence of $R^1$ is halogen, unsubstituted $C_{1-6}$ alkyl, $C_{2-6}$ alkoxyalkyl, $C_{1-6}$ hydroxyalkyl, or unsubstituted $C_{3-4}$ cycloalkyl.

In certain embodiments of Formula I-j, $R^1$ is —F, methyl, —$C(CH_3)_2OCH_3$, —$CH(OCH_3)CH_3$, —$CH(OH)CH_3$, —$CH(OCH_2CH_3)CH_3$, or unsubstituted cyclopropyl.

In certain embodiments, the compound of Formula I is a compound of Formula I-k:

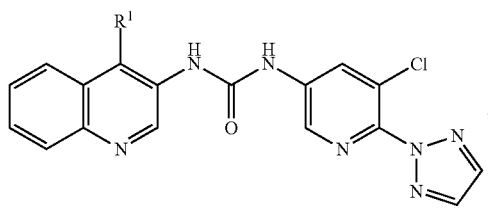

I-k or a pharmaceutically acceptable salt, co-crystal, tautomer, stereoisomer, solvate, hydrate, polymorph, isotopically enriched derivative, or prodrug thereof.

In certain embodiments of Formula I-k, $R^1$ is halogen, unsubstituted $C_{1-6}$ alkyl, $C_{1-6}$ alkoxyalkyl, $C_{1-6}$ hydroxyalkyl, $C_{1-6}$ azidoalkyl, $C_{1-6}$ haloalkyl, or unsubstituted $C_{3-4}$ cycloalkyl.

In certain embodiments of Formula I-k, $R^1$ is —Br, —CH$_3$, —CH(CH$_3$)$_2$, —C(CH$_3$)$_2$OCH$_3$, —CH(OCH$_3$)CH$_3$, —CH(OH)CH$_3$, —CH(N$_3$)CH$_3$, CF$_3$, or unsubstituted cyclopropyl.

In certain embodiments of Formula I-k, $R^1$ is $C_{2-6}$ alkoxyalkyl, $C_{1-6}$ hydroxyalkyl, or unsubstituted $C_{3-4}$ cycloalkyl. In certain embodiments of Formula I-k, $R^1$ is —C(CH$_3$)$_2$OCH$_3$, —CH(OCH$_3$)CH$_3$, —CH(OH)CH$_3$, —CH(OCH$_2$CH$_3$)CH$_3$, or unsubstituted cyclopropyl.

In certain embodiments, the compound of Formula I is a compound of Formula I-1:

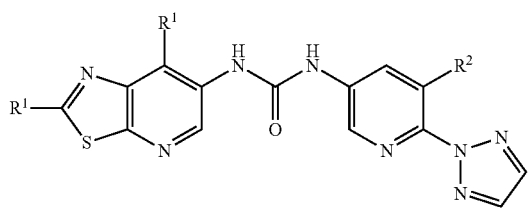

I-1 or a pharmaceutically acceptable salt, co-crystal, tautomer, stereoisomer, solvate, hydrate, polymorph, isotopically enriched derivative, or prodrug thereof.

In certain embodiments of Formula I-1, each occurrence of $R^1$ is, independently, unsubstituted $C_{1-6}$ alkyl or unsubstituted $C_{3-6}$ cycloalkyl. In certain embodiments of Formula I-1, each occurrence of $R^1$ is, independently, unsubstituted $C_{1-6}$ alkyl or unsubstituted cyclopropyl.

In certain embodiments of Formula I-1, each occurrence of $R^1$ is, independently, unsubstituted $C_{1-6}$ alkyl or substituted or unsubstituted $C_{2-6}$ alkoxyalkyl. In certain embodiments of Formula I-1, each occurrence of $R^1$ is, independently, methyl or substituted or —CH(OCH$_2$CH$_3$)CH$_3$.

In certain embodiments of Formula I-1, $R^2$ is halogen. In certain embodiments of Formula I-1, $R^2$ is —Cl, —Br, or —F. In certain embodiments of Formula I-1, $R^2$ is —Cl.

In certain embodiments of Formula I-1, each occurrence of $R^1$ is, independently, unsubstituted $C_{1-6}$ alkyl or unsubstituted $C_{3-6}$ cycloalkyl; and $R^2$ is halogen. In certain embodiments of Formula I-1, each occurrence of $R^1$ is, independently, unsubstituted $C_{1-6}$ alkyl or unsubstituted cyclopropyl; and $R^2$ is —C$_1$.

In certain embodiments of Formula I-1, each occurrence of $R^1$ is, independently, unsubstituted $C_{1-6}$ alkyl or substituted or unsubstituted $C_{2-6}$ alkoxyalkyl; and $R^2$ is halogen. In certain embodiments of Formula I-1, each occurrence of $R^1$ is, independently, methyl or substituted or —CH(OCH$_2$CH$_3$)CH$_3$; and $R^2$ is —Cl.

In certain embodiments, the compound of Formula I is a compound of Formula I-m:

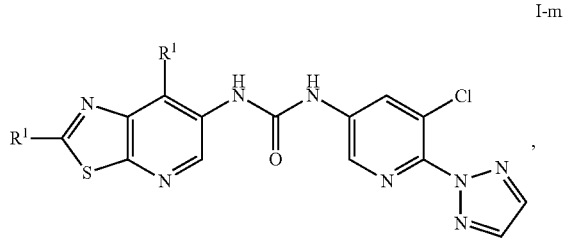

I-m or a pharmaceutically acceptable salt, co-crystal, tautomer, stereoisomer, solvate, hydrate, polymorph, isotopically enriched derivative, or prodrug thereof.

In certain embodiments of Formula I-m, each occurrence of $R^1$ is, independently, unsubstituted $C_{1-6}$ alkyl or unsubstituted $C_{3-6}$ cycloalkyl. In certain embodiments of Formula I-m, each occurrence of $R^1$ is, independently, unsubstituted $C_{1-6}$ alkyl or unsubstituted cyclopropyl.

In certain embodiments of Formula I-m, each occurrence of $R^1$ is, independently, unsubstituted $C_{1-6}$ alkyl or substituted or unsubstituted $C_{2-6}$ alkoxyalkyl. In certain embodiments of Formula I-m, each occurrence of $R^1$ is, independently, methyl or substituted or —CH(OCH$_2$CH$_3$)CH$_3$.

In certain embodiments, the compound of Formula I is a compound of Formula I-n:

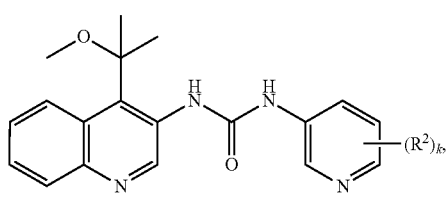

I-n or a pharmaceutically acceptable salt, co-crystal, tautomer, stereoisomer, solvate, hydrate, polymorph, isotopically enriched derivative, or prodrug thereof, wherein $R^2$ and k are as defined for Formula I.

In certain embodiments, the compound of Formula I is a compound of Formula I-o:

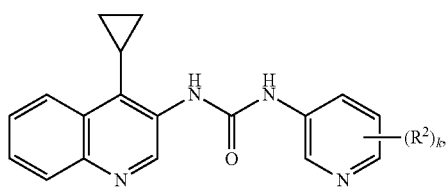

I-o or a pharmaceutically acceptable salt, co-crystal, tautomer, stereoisomer, solvate, hydrate, polymorph, isotopically enriched derivative, or prodrug thereof, wherein $R^2$ and k are as defined for Formula I.

In certain embodiments, the compound of Formula I is a compound of Formula I-p:

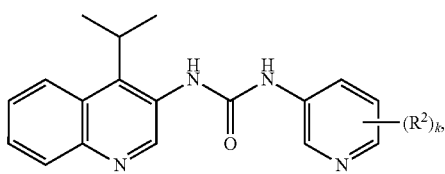

I-p or a pharmaceutically acceptable salt, co-crystal, tautomer, stereoisomer, solvate, hydrate, polymorph, isotopically enriched derivative, or prodrug thereof, wherein $R^2$ and k are as defined for Formula I.

In certain embodiments, the compound of Formula I is a compound of Formula I-q:

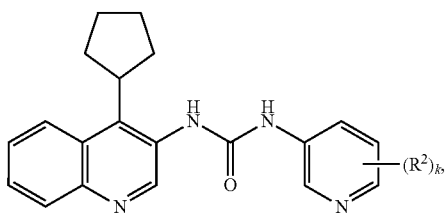

I-q or a pharmaceutically acceptable salt, co-crystal, tautomer, stereoisomer, solvate, hydrate, polymorph, isotopically enriched derivative, or prodrug thereof, wherein $R^2$ and k are as defined for Formula I.

In certain embodiments, the compound of Formula I is a compound of Formula I-r:

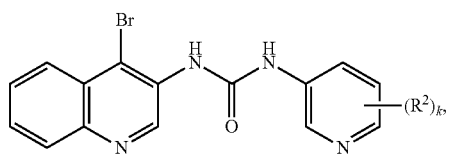

I-r or a pharmaceutically acceptable salt, co-crystal, tautomer, stereoisomer, solvate, hydrate, polymorph, isotopically enriched derivative, or prodrug thereof, wherein $R^2$ and k are as defined for Formula I.

In certain embodiments, the compound of Formula I is a compound of Formula I-s:

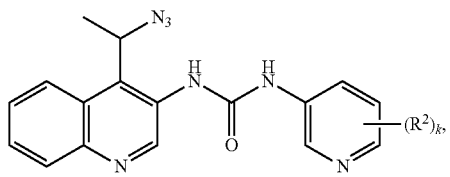

I-s or a pharmaceutically acceptable salt, co-crystal, tautomer, stereoisomer, solvate, hydrate, polymorph, isotopically enriched derivative, or prodrug thereof, wherein $R^2$ and k are as defined for Formula I.

In certain embodiments, the compound of Formula I is a compound of Formula I-t:

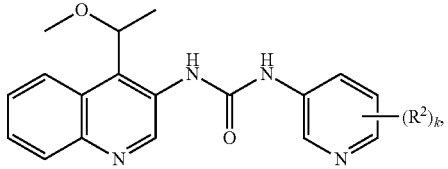

I-t or a pharmaceutically acceptable salt, co-crystal, tautomer, stereoisomer, solvate, hydrate, polymorph, isotopically enriched derivative, or prodrug thereof, wherein $R^2$ and k are as defined for Formula I.

In certain embodiments, the compound of Formula I is a compound of Formula I-u:

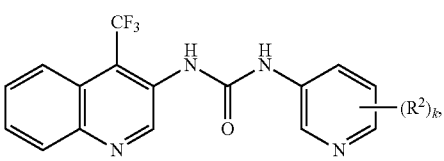

I-u or a pharmaceutically acceptable salt, co-crystal, tautomer, stereoisomer, solvate, hydrate, polymorph, isotopically enriched derivative, or prodrug thereof, wherein $R^2$ and k are as defined for Formula I.

In certain embodiments, the compound of Formula I is a compound of Formula I-v:

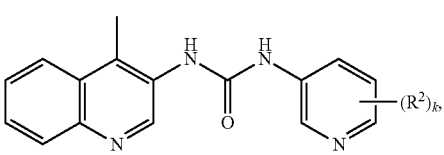

I-v or a pharmaceutically acceptable salt, co-crystal, tautomer, stereoisomer, solvate, hydrate, polymorph, isotopically enriched derivative, or prodrug thereof, wherein $R^2$ and k are as defined for Formula I.

In certain embodiments, the compound of Formula I is a compound of Formula I-w:

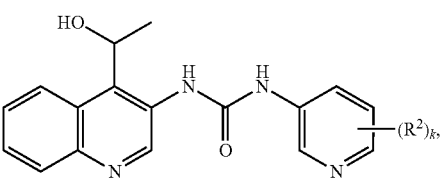

I-w or a pharmaceutically acceptable salt, co-crystal, tautomer, stereoisomer, solvate, hydrate, polymorph, isotopically enriched derivative, or prodrug thereof, wherein $R^2$ and k are as defined for Formula I.

In certain embodiments, the compound of Formula I is a compound of Formula I-x:

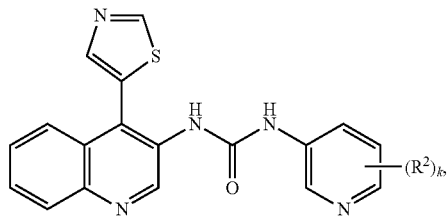

I-x or a pharmaceutically acceptable salt, co-crystal, tautomer, stereoisomer, solvate, hydrate, polymorph, isotopically enriched derivative, or prodrug thereof, wherein $R^2$ and k are as defined for Formula I.

In certain embodiments, the compound of Formula I is a compound of Formula I-y:

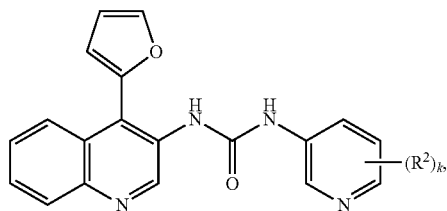

I-y or a pharmaceutically acceptable salt, co-crystal, tautomer, stereoisomer, solvate, hydrate, polymorph, isotopically enriched derivative, or prodrug thereof, wherein $R^2$ and k are as defined for Formula I.

In certain embodiments, the compound of Formula I is a compound of Formula I-z:

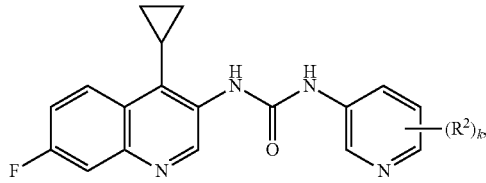

I-z or a pharmaceutically acceptable salt, co-crystal, tautomer, stereoisomer, solvate, hydrate, polymorph, isotopically enriched derivative, or prodrug thereof, wherein $R^2$ and k are as defined for Formula I.

In certain embodiments, the compound of Formula I is a compound of Formula I-aa:

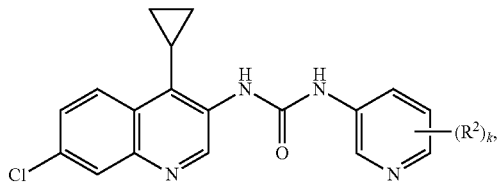

I-aa or a pharmaceutically acceptable salt, co-crystal, tautomer, stereoisomer, solvate, hydrate, polymorph, isotopically enriched derivative, or prodrug thereof, wherein $R^2$ and k are as defined for Formula I.

In certain embodiments, the compound of Formula I is a compound of Formula I-bb:

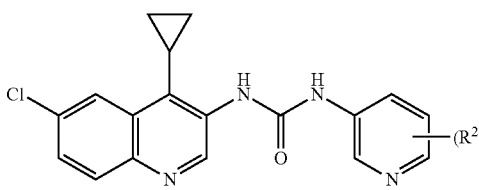

I-bb or a pharmaceutically acceptable salt, co-crystal, tautomer, stereoisomer, solvate, hydrate, polymorph, isotopically enriched derivative, or prodrug thereof, wherein $R^2$ and k are as defined for Formula I.

In certain embodiments, the compound of Formula I is a compound of Formula I-cc:

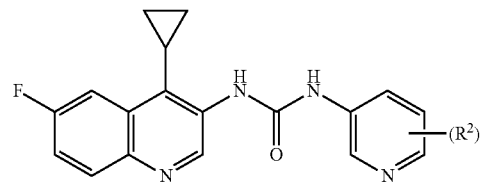

I-cc or a pharmaceutically acceptable salt, co-crystal, tautomer, stereoisomer, solvate, hydrate, polymorph, isotopically enriched derivative, or prodrug thereof, wherein $R^2$ and k are as defined for Formula I.

In certain embodiments, the compound of Formula I is a compound of Formula I-dd:

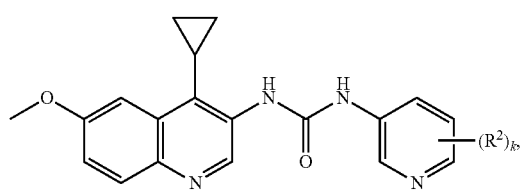

I-dd or a pharmaceutically acceptable salt, co-crystal, tautomer, stereoisomer, solvate, hydrate, polymorph, isotopically enriched derivative, or prodrug thereof, wherein $R^2$ and k are as defined for Formula I.

In certain embodiments, the compound of Formula I is a compound of Formula I-ee:

I-ee

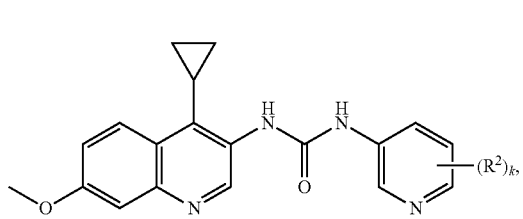

or a pharmaceutically acceptable salt, co-crystal, tautomer, stereoisomer, solvate, hydrate, polymorph, isotopically enriched derivative, or prodrug thereof, wherein $R^2$ and k are as defined for Formula I.

In certain embodiments, the compound of Formula I is a compound of Formula I-ff:

I-ff

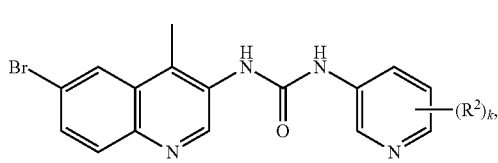

or a pharmaceutically acceptable salt, co-crystal, tautomer, stereoisomer, solvate, hydrate, polymorph, isotopically enriched derivative, or prodrug thereof, wherein $R^2$ and k are as defined for Formula I.

In certain embodiments, the compound of Formula I is a compound of Formula I-gg:

I-gg

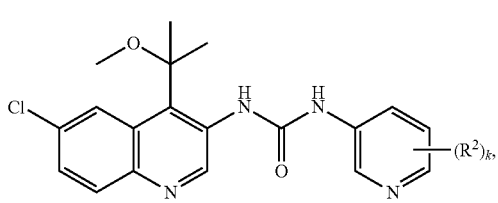

or a pharmaceutically acceptable salt, co-crystal, tautomer, stereoisomer, solvate, hydrate, polymorph, isotopically enriched derivative, or prodrug thereof, wherein $R^2$ and k are as defined for Formula I.

In certain embodiments, the compound of Formula I is a compound of Formula I-hh:

I-hh

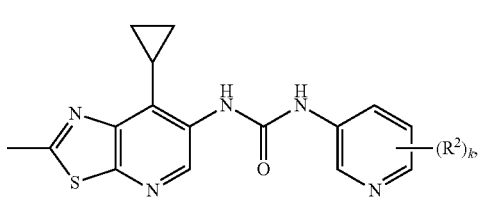

or a pharmaceutically acceptable salt, co-crystal, tautomer, stereoisomer, solvate, hydrate, polymorph, isotopically enriched derivative, or prodrug thereof, wherein $R^2$ and k are as defined for Formula I.

In certain embodiments, the compound of Formula I is a compound of Formula I-ii:

I-ii

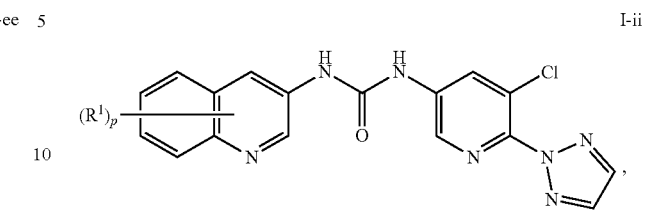

or a pharmaceutically acceptable salt, co-crystal, tautomer, stereoisomer, solvate, hydrate, polymorph, isotopically enriched derivative, or prodrug thereof, wherein $R^1$ and p are as defined for Formula I.

In certain embodiments, the compound of Formula I is a compound of Formula I-jj:

I-jj

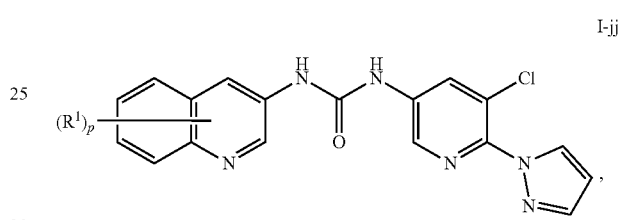

or a pharmaceutically acceptable salt, co-crystal, tautomer, stereoisomer, solvate, hydrate, polymorph, isotopically enriched derivative, or prodrug thereof, wherein $R^1$ and p are as defined for Formula I.

In certain embodiments, the compound of Formula I is a compound of Formula I-kk:

I-kk

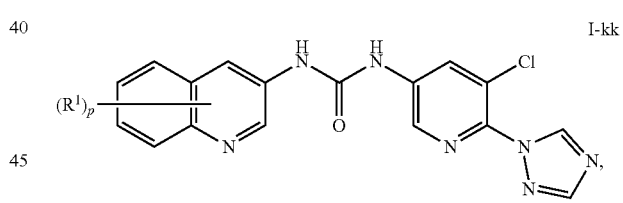

or a pharmaceutically acceptable salt, co-crystal, tautomer, stereoisomer, solvate, hydrate, polymorph, isotopically enriched derivative, or prodrug thereof, wherein $R^1$ and p are as defined for Formula I.

In certain embodiments, the compound of Formula I is a compound of Formula I-ll:

I-ll

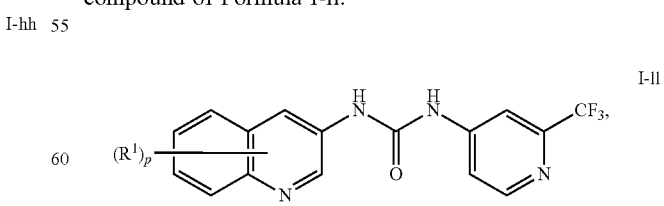

or a pharmaceutically acceptable salt, co-crystal, tautomer, stereoisomer, solvate, hydrate, polymorph, isotopically enriched derivative, or prodrug thereof, wherein $R^1$ and p are as defined for Formula I.

In certain embodiments, the compound of Formula I is a compound of Formula I-mm:

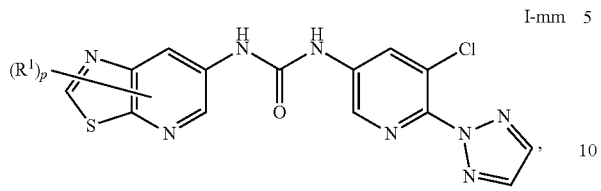

I-mm or a pharmaceutically acceptable salt, co-crystal, tautomer, stereoisomer, solvate, hydrate, polymorph, isotopically enriched derivative, or prodrug thereof, wherein $R^1$ and p are as defined for Formula I.

In certain embodiments, the compound of Formula I is a compound of Formula I-nn:

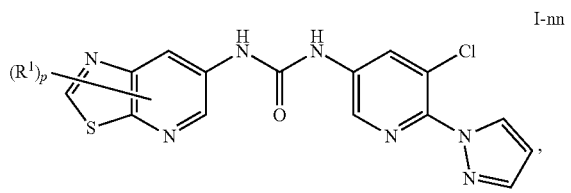

I-nn or a pharmaceutically acceptable salt, co-crystal, tautomer, stereoisomer, solvate, hydrate, polymorph, isotopically enriched derivative, or prodrug thereof, wherein $R^1$ and p are as defined for Formula I.

In certain embodiments, the compound of Formula I is a compound of Formula I-oo:

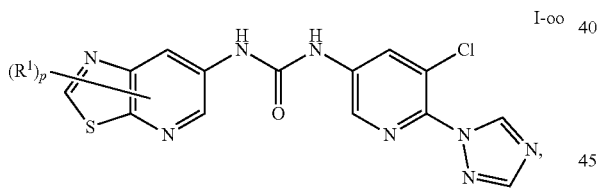

I-oo or a pharmaceutically acceptable salt, co-crystal, tautomer, stereoisomer, solvate, hydrate, polymorph, isotopically enriched derivative, or prodrug thereof, wherein $R^1$ and p are as defined for Formula I.

In certain embodiments, the compound of Formula I is a compound of Formula I-pp:

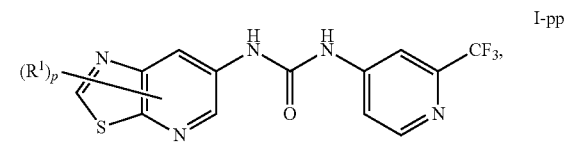

I-pp or a pharmaceutically acceptable salt, co-crystal, tautomer, stereoisomer, solvate, hydrate, polymorph, isotopically enriched derivative, or prodrug thereof, wherein $R^1$ and p are as defined for Formula I.

In certain embodiments, the compound of Formula I is a compound of Formula I-qq:

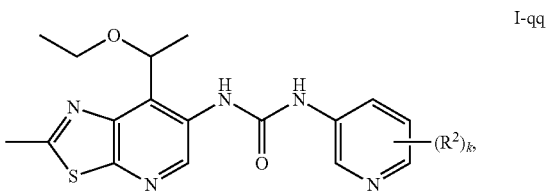

I-qq or a pharmaceutically acceptable salt, co-crystal, tautomer, stereoisomer, solvate, hydrate, polymorph, isotopically enriched derivative, or prodrug thereof, wherein $R^2$ and k are as defined for Formula I.

In certain embodiments, the compound of Formula I is a compound of Formula I-rr:

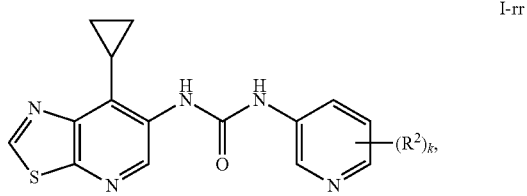

I-rr or a pharmaceutically acceptable salt, co-crystal, tautomer, stereoisomer, solvate, hydrate, polymorph, isotopically enriched derivative, or prodrug thereof, wherein $R^2$ and k are as defined for Formula I.

In certain embodiments, the compound of Formula I is a compound of Formula I-ss:

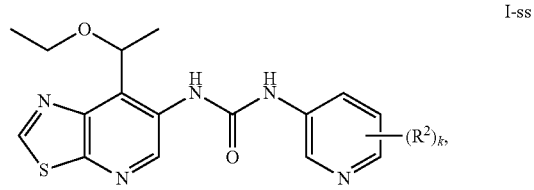

I-ss or a pharmaceutically acceptable salt, co-crystal, tautomer, stereoisomer, solvate, hydrate, polymorph, isotopically enriched derivative, or prodrug thereof, wherein $R^2$ and k are as defined for Formula I.

In certain embodiments, the compound of Formula I is a compound of Formula I-tt:

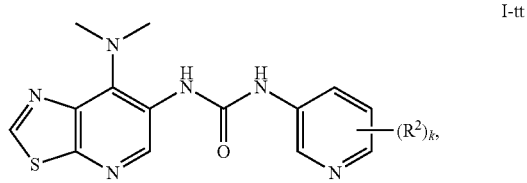

I-tt or a pharmaceutically acceptable salt, co-crystal, tautomer, stereoisomer, solvate, hydrate, polymorph, isotopically enriched derivative, or prodrug thereof, wherein $R^2$ and k are as defined for Formula I.

In certain embodiments, the compound of Formula I is a compound of Formula I-uu:

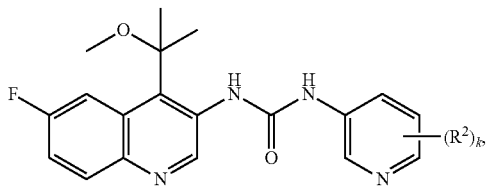

I-uu or a pharmaceutically acceptable salt, co-crystal, tautomer, stereoisomer, solvate, hydrate, polymorph, isotopically enriched derivative, or prodrug thereof, wherein $R^2$ and k are as defined for Formula I.

In certain embodiments, the compound of Formula I is a compound of Formula I-vv:

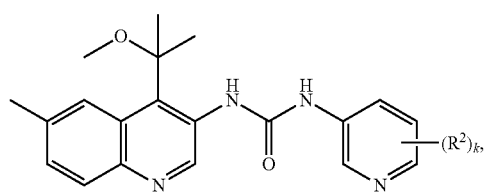

I-vv or a pharmaceutically acceptable salt, co-crystal, tautomer, stereoisomer, solvate, hydrate, polymorph, isotopically enriched derivative, or prodrug thereof, wherein $R^2$ and k are as defined for Formula I.

In certain embodiments, the compound of Formula I is a compound of Formula I-ww:

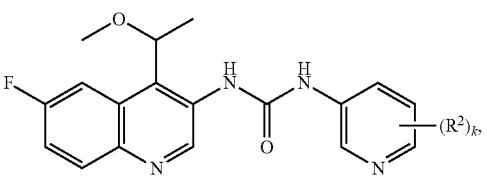

I-ww or a pharmaceutically acceptable salt, co-crystal, tautomer, stereoisomer, solvate, hydrate, polymorph, isotopically enriched derivative, or prodrug thereof, wherein $R^2$ and k are as defined for Formula I.

In certain embodiments, the compound of Formula I is a compound of Formula I-xx:

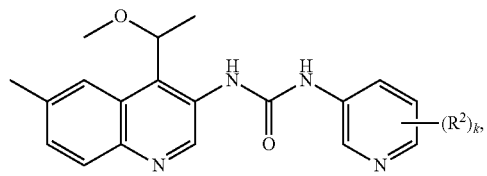

I-xx or a pharmaceutically acceptable salt, co-crystal, tautomer, stereoisomer, solvate, hydrate, polymorph, isotopically enriched derivative, or prodrug thereof, wherein $R^2$ and k are as defined for Formula I.

In certain embodiments, the compound of Formula I is a compound of Formula I-yy:

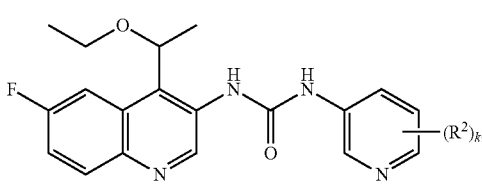

I-yy or a pharmaceutically acceptable salt, co-crystal, tautomer, stereoisomer, solvate, hydrate, polymorph, isotopically enriched derivative, or prodrug thereof, wherein $R^2$ and k are as defined for Formula I.

In certain embodiments, the compound of Formula I is a compound of Formula I-zz:

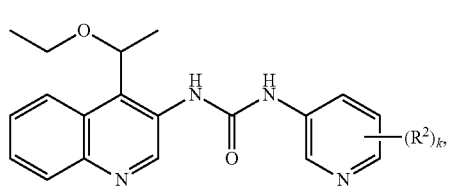

I-zz or a pharmaceutically acceptable salt, co-crystal, tautomer, stereoisomer, solvate, hydrate, polymorph, isotopically enriched derivative, or prodrug thereof, wherein $R^2$ and k are as defined for Formula I.

In certain embodiments, the compound of Formula I is a compound of Formula I-aaa:

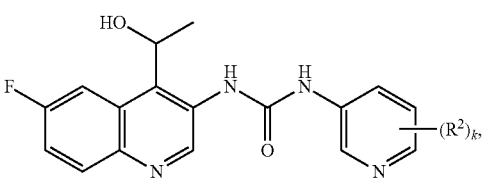

I-aaa or a pharmaceutically acceptable salt, co-crystal, tautomer, stereoisomer, solvate, hydrate, polymorph, isotopically enriched derivative, or prodrug thereof, wherein $R^2$ and k are as defined for Formula I.

In certain embodiments, the compound of Formula I is one of the following compounds, or a pharmaceutically acceptable salt, co-crystal, tautomer, stereoisomer, solvate, hydrate, polymorph, isotopically enriched derivative, or prodrug thereof:

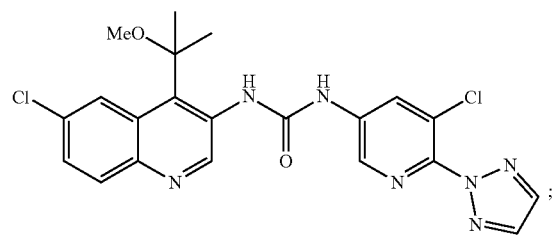
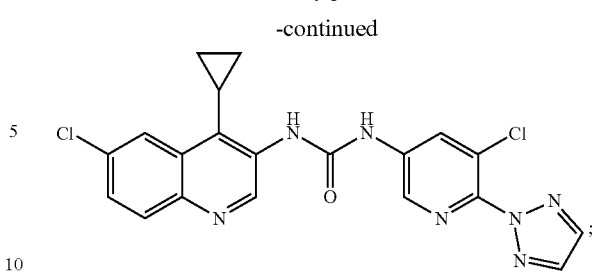
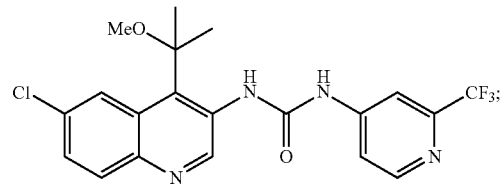
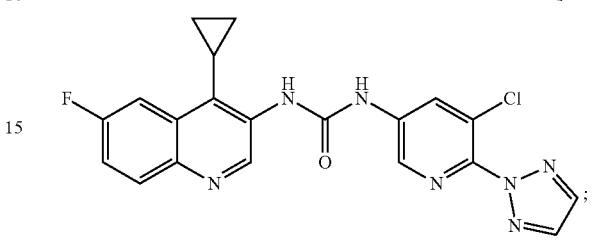
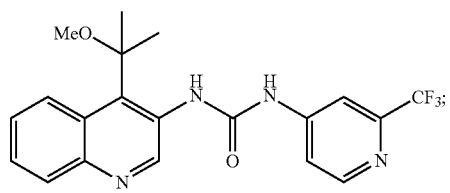
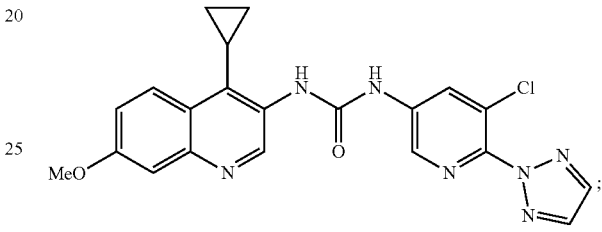
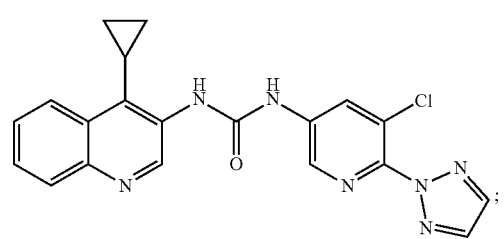
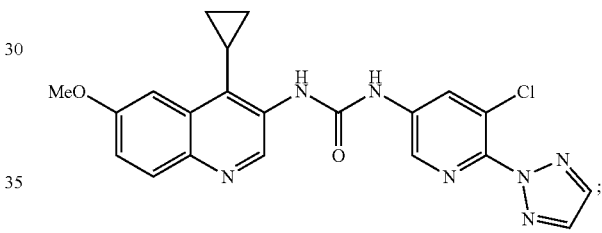
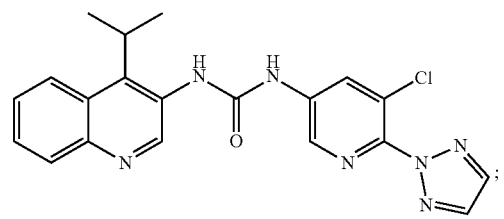
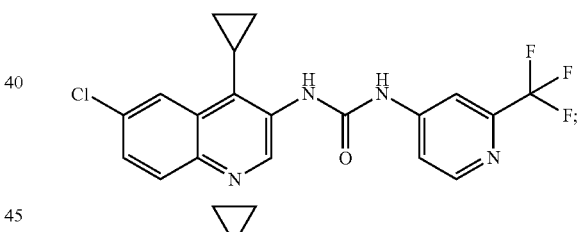
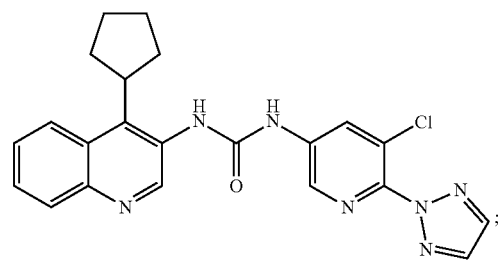
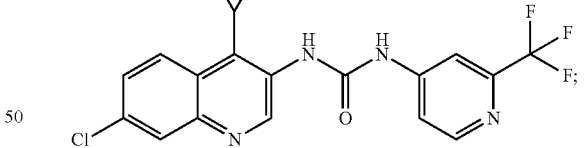
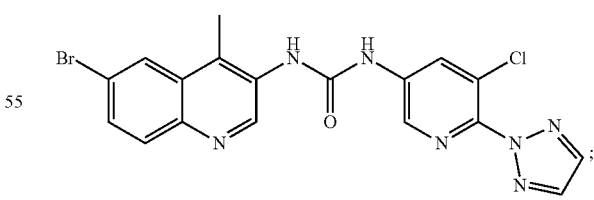
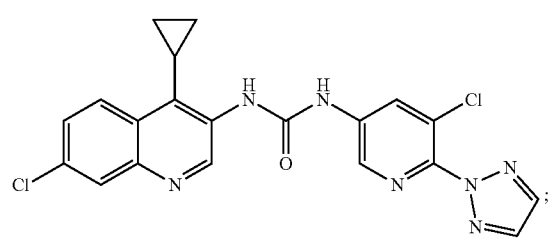
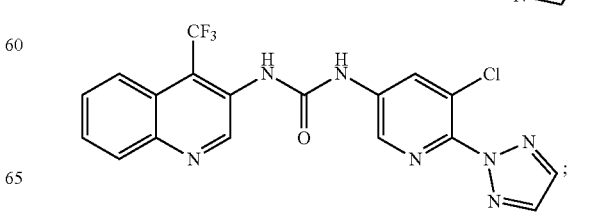

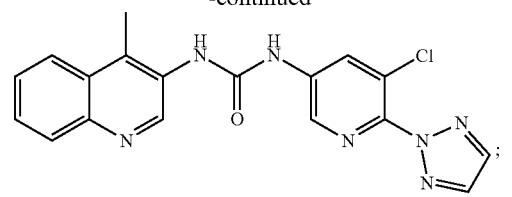
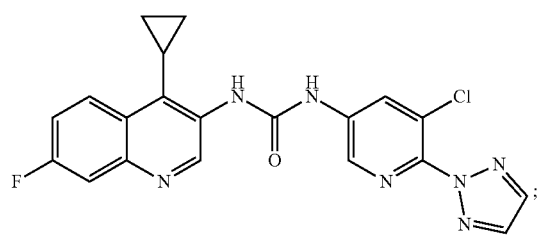
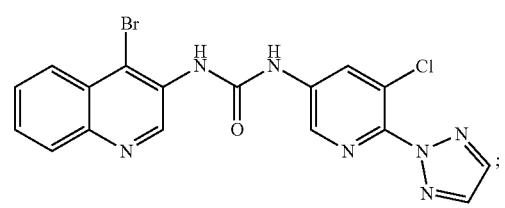
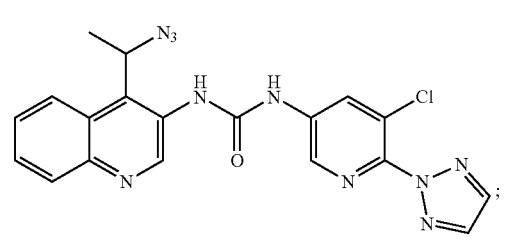
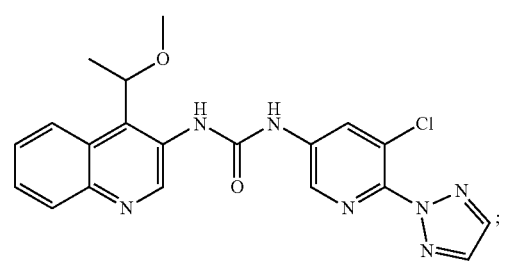
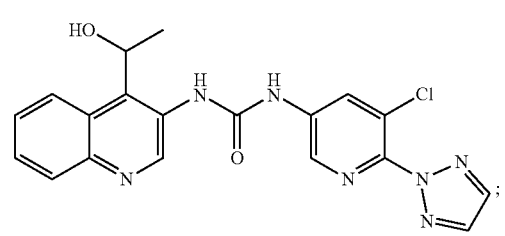
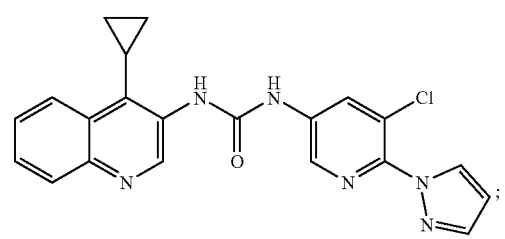
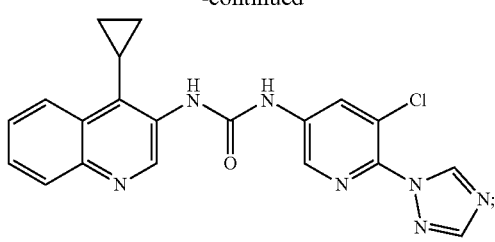
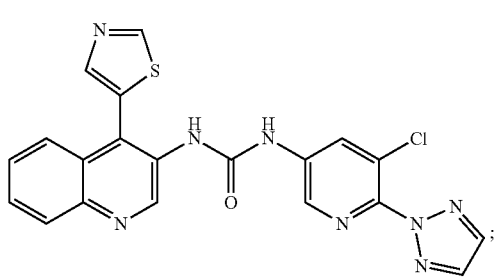
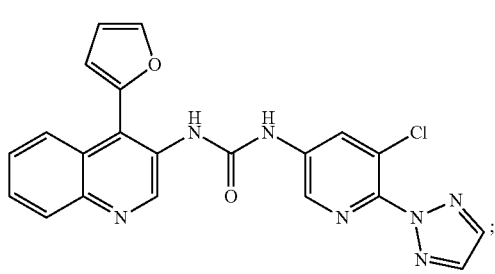
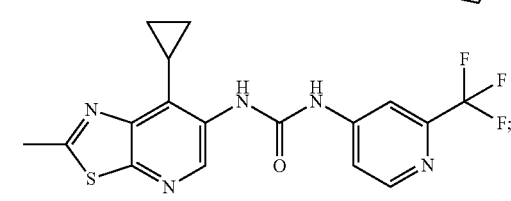
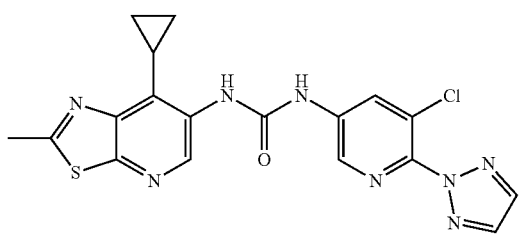
In certain embodiments, the compound of Formula I is one of the following compounds, or a pharmaceutically acceptable salt, co-crystal, tautomer, stereoisomer, solvate, hydrate, polymorph, isotopically enriched derivative, or prodrug thereof:
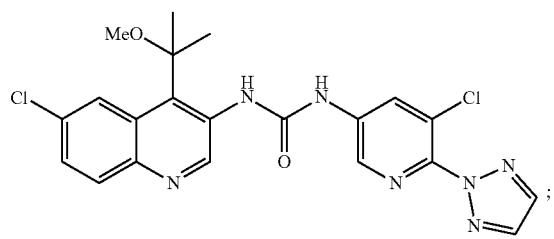

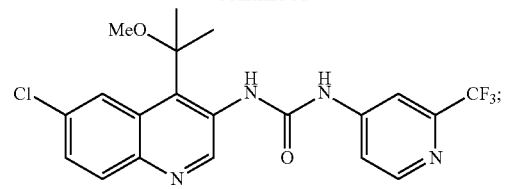
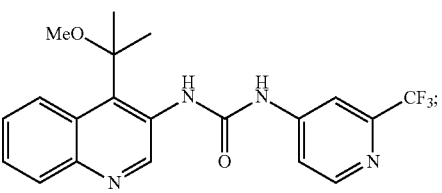
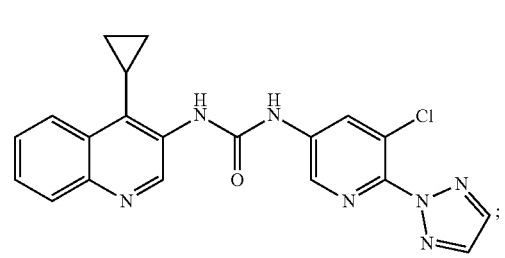
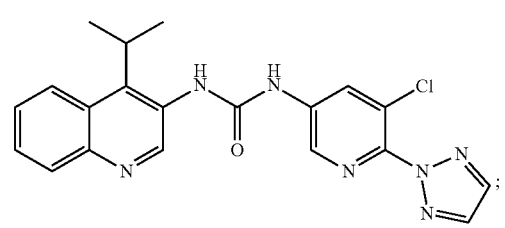
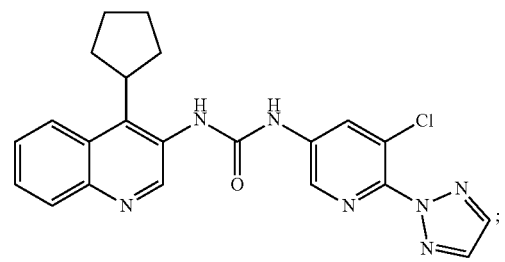
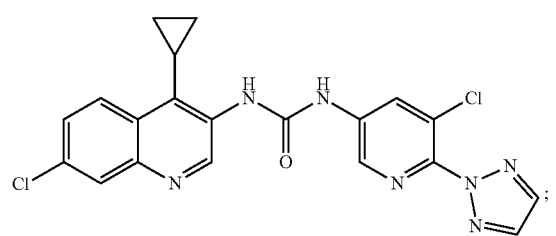
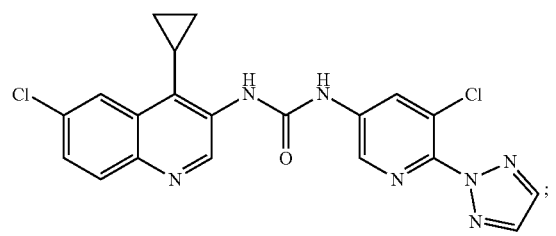
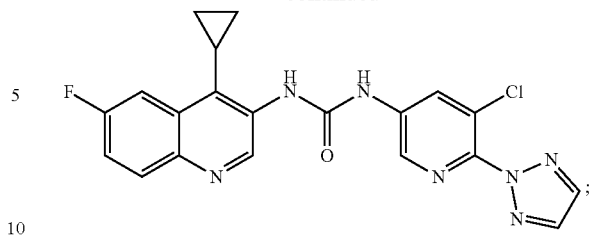
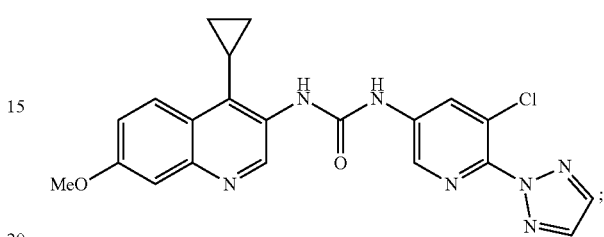
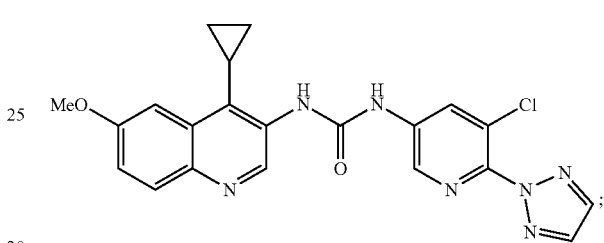
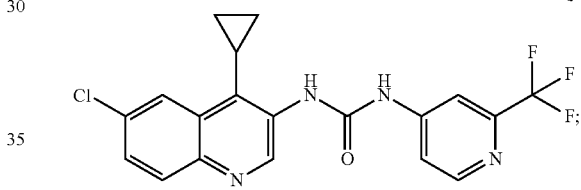
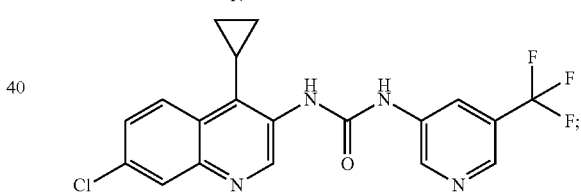
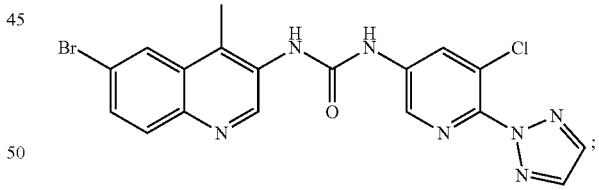
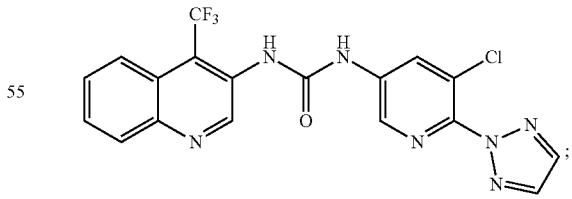
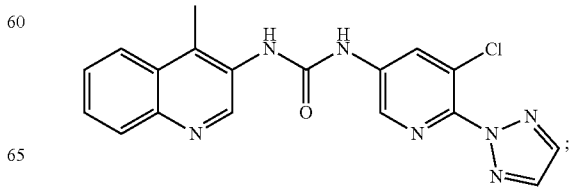

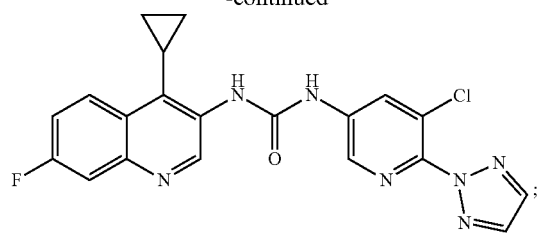
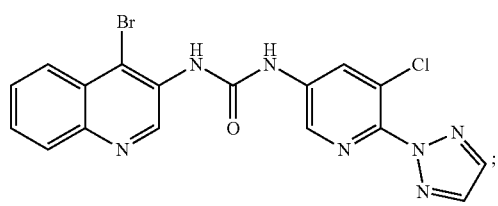
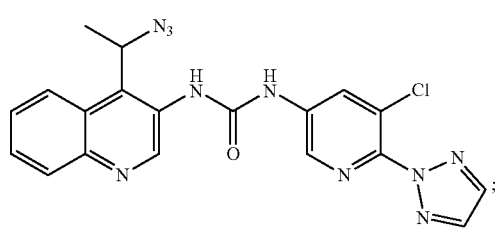
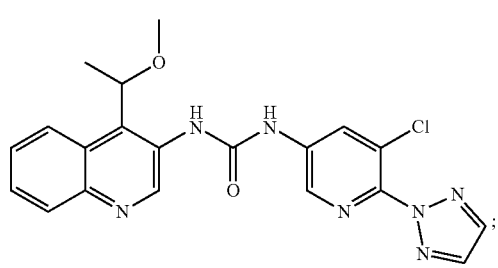
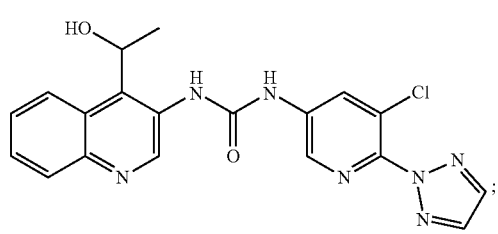
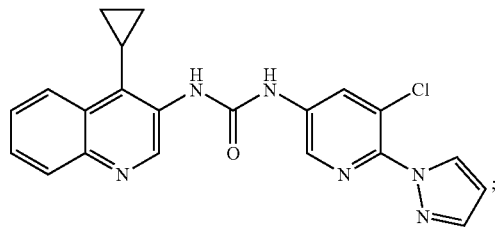
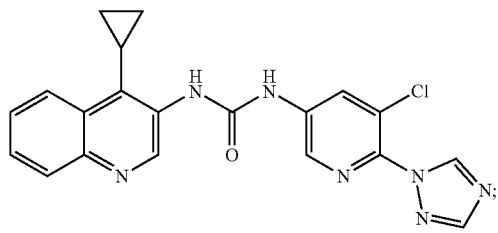
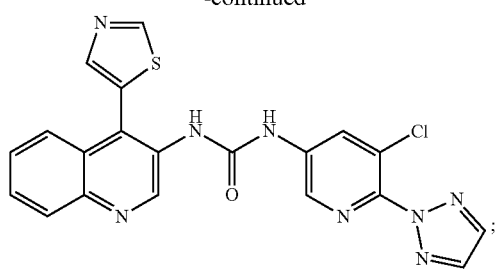
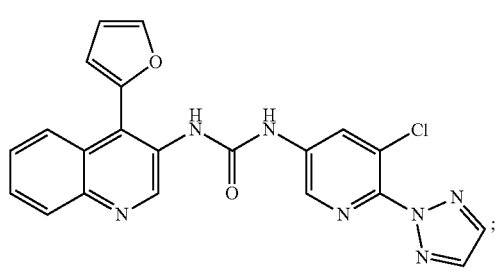
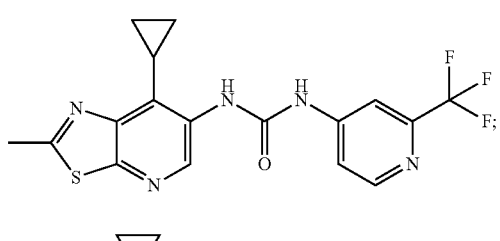
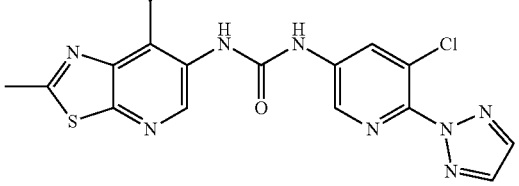
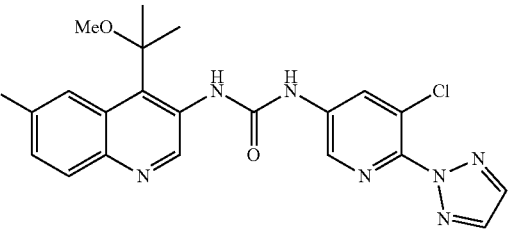
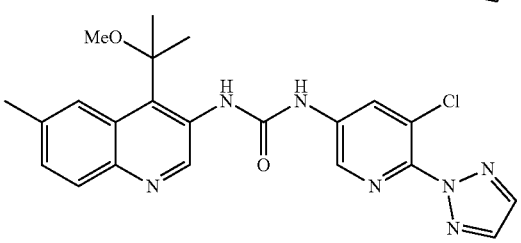
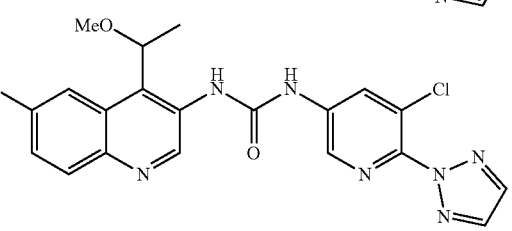

-continued

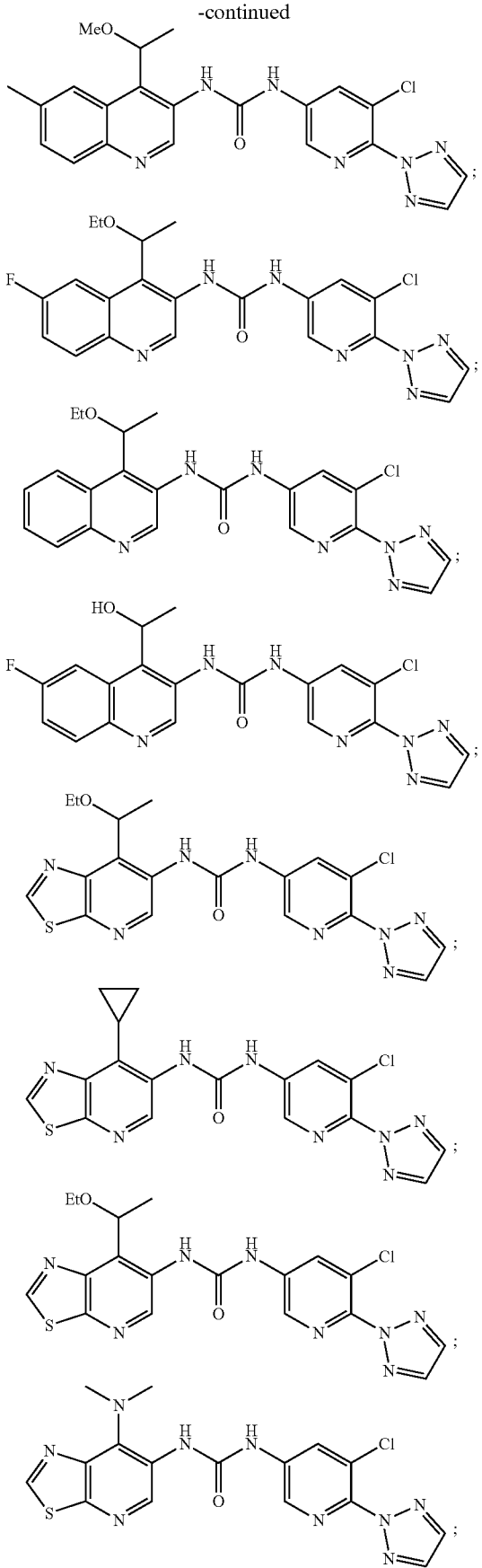

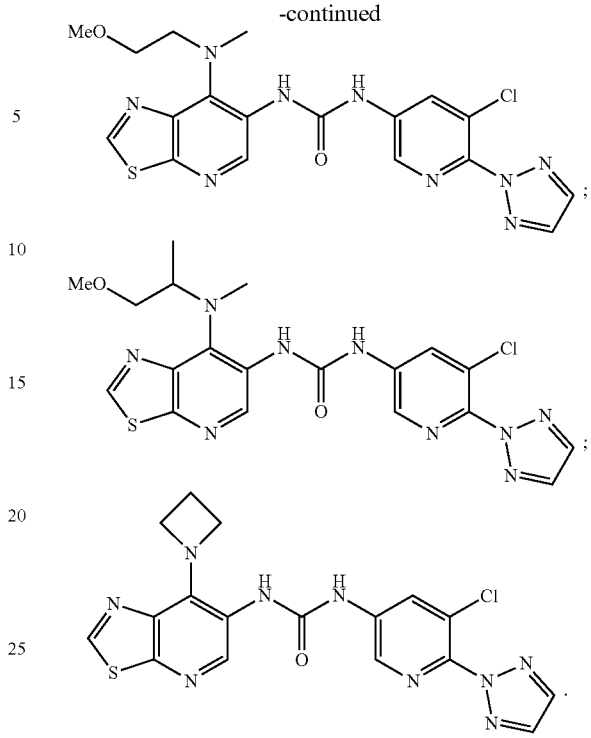

In certain embodiments, the compound of Formula I inhibits MALT1 with a $K_i$ of less than 100,000 nM, less than 50,000 nM, less than 20,000 nM, less than 10,000 nM, less than 5,000 nM, less than 2,500 nM, less than 1,000 nM, less than 900 nM, less than 800 nM, less than 700 nM, less than 600 nM, less than 500 nM, less than 400 nM, less than 300 nM, less than 200 nM, less than 100 nM, less than 90 nM, less than 80 nM, less than 70 nM, less than 60 nM, less than 50 nM, less than 40 nM, less than 30 nM, less than 20 nM, less than 10 nM, less than 5 nM, less than 4 nM, less than 3 nM, less than 2 nM, or less than 1 nM.

In certain embodiments, the compound of Formula I inhibits MALT1 with an $IC_{50}$ of less than 100,000 nM, less than 50,000 nM, less than 20,000 nM, less than 10,000 nM, less than 5,000 nM, less than 2,500 nM, less than 1,000 nM, less than 900 nM, less than 800 nM, less than 700 nM, less than 600 nM, less than 500 nM, less than 400 nM, less than 300 nM, less than 200 nM, less than 100 nM, less than 90 nM, less than 80 nM, less than 70 nM, less than 60 nM, less than 50 nM, less than 40 nM, less than 30 nM, less than 20 nM, less than 10 nM, less than 5 nM, less than 4 nM, less than 3 nM, less than 2 nM, or less than 1 nM.

Pharmaceutical Compositions, Kits, and Administration

The present disclosure provides pharmaceutical compositions comprising a compound of Formula I, or a pharmaceutically acceptable salt, co-crystal, tautomer, stereoisomer, solvate, hydrate, polymorph, isotopically enriched derivative, or prodrug thereof, and optionally a pharmaceutically acceptable excipient. In certain embodiments, the pharmaceutical composition described herein comprises a compound of Formula I, or a pharmaceutically acceptable salt thereof, and a pharmaceutically acceptable excipient.

In certain embodiments, the compound of Formula I is provided in an effective amount in the pharmaceutical composition. In certain embodiments, the effective amount is a therapeutically effective amount. In certain embodiments, the effective amount is a prophylactically effective amount. In certain embodiments, the effective amount is an amount effective for treating a proliferative disease in a subject in need thereof. In certain embodiments, the effective amount is an amount effective for preventing a proliferative disease in a subject in need thereof. In certain embodiments, the effective amount is an amount effective for treating a hematological cancer in a subject in need thereof. In certain embodiments, the effective amount is an amount effective for treating an autoimmune disease in a subject in need thereof. In certain embodiments, the effective amount is an amount effective for preventing an autoimmune disease in a subject in need thereof. In certain embodiments, the effective amount is an amount effective for treating inflammatory disease in a subject in need thereof. In certain embodiments, the effective amount is an amount effective for preventing inflammatory disease in a subject in need thereof. In certain embodiments, the effective amount is an amount effective for reducing the risk of developing a disease (e.g., proliferative disease, hematological cancer, inflammatory disease, or autoimmune disease) in a subject in need thereof. In certain embodiments, the effective amount is an amount effective for inhibiting the activity (e.g., aberrant activity, such as increased activity) of MALT1 in a subject or cell.

In certain embodiments, the subject is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs). In certain embodiments, the subject is a fish or reptile.

In certain embodiments, the effective amount is an amount effective for inhibiting the activity of MALT1 by at least about 10%, at least about 20%, at least about 30%, at least about 40%, at least about 50%, at least about 60%, at least about 70%, at least about 80%, at least about 90%, at least about 95%, at least about 98%, or at least about 99%. In certain embodiments, the effective amount is an amount effective for inhibiting the activity of MALT1 by a range between a percentage described in this paragraph and another percentage described in this paragraph, inclusive.

The present disclosure provides pharmaceutical compositions comprising a compound that interacts with MALT1 for use in treating a MALT1-related disease or disorder in a subject in need thereof. In certain embodiments, the composition is for use in treating autoimmune disease and/or inflammatory disease (e.g., rheumatoid arthritis, multiple sclerosis, psoriasis, systemic lupus). In certain embodiments, the composition is for use in treating a proliferative disease in a subject in need thereof. In certain embodiments, the composition is for use in treating cancer in a subject in need thereof. In certain embodiments, the composition is for use in treating a hematological cancer. In certain embodiments, the composition is for use in treating a lymphoid malignancy. In certain embodiments, the composition is for use in treating a leukemia, a lymphoma, or multiple myeloma. In certain embodiments, the composition is for use in treating a non-Hodgkin's lymphoma. In certain embodiments, the composition is for use in treating mantle cell lymphoma. In certain embodiments, the composition is for use in treating DLBCL. In certain embodiments, the composition is for use in treating ABC-DLBCL. In certain embodiments, the composition is for use in treating ABC-DLBCL having one or more CARD11 (Caspase recruitment domain-containing protein 11) activating mutations.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, and/or in reducing the risk to develop a disease in a subject in need thereof), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a pharmaceutical composition described herein including a compound described herein and an additional pharmaceutical agent exhibit a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease, hematological cancer, autoimmune disease, and/or inflammatory disease). Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, anti-proliferative agents, anti-cancer agents, anti-angiogenesis agents, anti-inflammatory agents, and immunosuppressants. In certain embodiments, the additional pharmaceutical agent is an immunotherapy. In certain embodiments, the additional pharmaceutical agent is an anti-proliferative agent. In certain embodiments, the additional pharmaceutical agent is an anti-cancer agent. In certain embodiments, the anti-cancer agents include, but are not limited to, epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), cell signaling pathway inhibitors (e.g., tyrosine protein kinase inhibitors), modulators of protein stability (e.g., proteasome inhibitors), Hsp90 inhibitors, glucocorticoids, all-trans retinoic acids, anti-estrogens (e.g., tamoxifen, raloxifene, and megestrol), LHRH agonists (e.g., goscrclin and leuprolide), anti-androgens (e.g. flutamide and bicalutamide), photodynamic therapies (e.g., vertoporfin (BPD-MA), phthalocyanine, photosensitizer Pc4, and demethoxy-hypocrellin A (2BA-2-DMHA)), nitrogen mustards (e.g., cyclophosphamide, ifosfamide, trofosfamide, chlorambucil, estramustine, and melphalan), nitrosoureas (e.g., carmustine (BCNU) and lomustine (CCNU)), alkylsulphonates (e.g., busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent such as nanoparticle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), antimetabolites, DHFR inhibitors (e.g., methotrexate, dichloromethotrexate, trimetrexate, edatrexate), IMP dehydrogenase inhibitors (e.g., mycophenolic acid, tiazofurin, ribavirin, and EICAR), ribonucleotide reductase inhibitors (e.g., hydroxyurea and deferoxamine), uracil analogs (e.g., 5-fluorouracil (5-FU), floxuridine, doxifluridine, ratitrexed, tegafur-uracil, capecitabine), cytosine analogs (e.g., cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g., bleomycin A2, bleomycin B2, peplomycin), anthracycline (e.g., daunorubicin, doxorubicin, pegylated liposomal doxorubicin, idarubicin, epirubicin, pirarubicin, zorubicin, mitoxantrone), MDR inhibitors (e.g. verapamil), Ca ATPase inhibitors (e.g., thapsigargin), thalidomide, lenalidomide, pomalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA), semaxanib (semaxinib, SU5416), sunitinib (SUTENT®, SU11248), toceranib (PALLADIA@), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TK1258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

In certain embodiments, the additional pharmaceutical agent is an immunotherapy. In certain embodiments, the immunotherapy is useful in the treatment of a cancer. Exemplary immunotherapies include, but are not limited to, T-cell therapies, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies. In certain embodiments, the immunotherapy is a T-cell therapy. In certain embodiments, the T-cell therapy is chimeric antigen receptor T cells (CAR-T). In certain embodiments, the immunotherapy is an antibody. In certain embodiments, the antibody is an anti-PD-1 antibody, an anti-PD-L1 antibody, an anti-CTLA-4 antibody, an anti-TIM3 antibody, an anti-OX40 antibody, an anti-GITR antibody, an anti-LAG-3 antibody, an anti-CD137 antibody, an anti-CD27 antibody, an anti-CD28 antibody, an anti-CD28H antibody, an anti-CD30 antibody, an anti-CD39 antibody, an anti-CD40 antibody, an anti-CD47 antibody, an anti-CD48 antibody, an anti-CD70 antibody, an anti-CD73 antibody, an anti-CD96 antibody, an anti-CD160 antibody, an anti-CD200 antibody, an anti-CD244 antibody, an anti-ICOS antibody, an anti-TNFRSF25 antibody, an anti-TMIGD2 antibody, an anti-DNAM1 antibody, an anti-BTLA antibody, an anti-LIGHT antibody, an anti-TIGIT antibody, an anti-VISTA antibody, an anti-HVEM antibody, an anti-Siglec antibody, an anti-GAL1 antibody, an anti-GAL3 antibody, an anti-GAL9 antibody, an anti-BTNL2 (butrophylins) antibody, an anti-B7-H3 antibody, an anti-B7-H4 antibody, an anti-B7-H5 antibody, an anti-B7-H6 antibody, an anti-KIR antibody, an anti-LIR antibody, an anti-ILT antibody, an anti-MICA antibody, an anti-MICB antibody, an anti-NKG2D antibody, an anti-NKG2A antibody, an anti-TGFβ antibody, an anti-TGFβR antibody, an anti-CXCR4 antibody, an anti-CXCL12 antibody, an anti-CCL2 antibody, an anti-IL-10 antibody, an anti-IL-13 antibody, an anti-IL-23 antibody, an anti-phosphatidylserine antibody, an anti-neuropilin antibody, an anti-GalCer antibody, an anti-HER2 antibody, an anti-VEGFA antibody, an anti-VEGFR antibody, an anti-EGFR antibody, or an anti-Tie2 antibody. In certain embodiments, the antibody is pembrolizumab, nivolumab, pidilizumab, ipilimumab, tremelimumab, durvalumab, atezolizumab, avelumab, PF-06801591, utomilumab, PDR001, PBF-509, MGB453, LAG525, AMP-224, INCSHR1210, INCAGN1876, INCAGN1949, samalizumab, PF-05082566, urelumab, lirilumab, lulizumab, BMS-936559, BMS-936561, BMS-986004, BMS-986012, BMS-986016, BMS-986178, IMP321, IPH2101, IPH2201, varilumab, ulocuplumab, monalizumab, MEDI0562, MEDI0680, MEDI1873, MEDI6383, MEDI6469, MEDI9447, AMG228, AMG820, CC-90002, CDX-1127, CGEN15001T, CGEN15022, CGEN15029, CGEN15049, CGEN15027, CGEN15052, CGEN15092, CX-072, CX-2009, CP-870893, lucatumumab, dacetuzumab, Chi Lob 7/4, RG6058, RG7686, RG7876, RG7888, TRX518, MK-4166, MGA271, IMC-CS4, emactuzumab, trastuzumab, pertuzumab, obinutuzumab, cabiralizumab, margetuximab, enoblituzumab, mogamulizumab, panitumumab, carlumab, bevacizumab, rituximab, or cetuximab.

In certain embodiments, the compounds or pharmaceutical compositions described herein can be administered in combination with an anti-cancer therapy including, but not limited to, surgery, radiation therapy, and transplantation (e.g., stem cell transplantation, bone marrow transplantation).

In certain embodiments, the compound or pharmaceutical composition is a solid. In certain embodiments, the compound or pharmaceutical composition is a powder. In certain embodiments, the compound or pharmaceutical composition can be dissolved in a liquid to make a solution. In certain embodiments, the compound or pharmaceutical composition is dissolved in water to make an aqueous solution. In certain embodiments, the pharmaceutical composition is a liquid for parental injection. In certain embodiments, the pharmaceutical composition is a liquid for oral administration (e.g., ingestion). In certain embodiments, the pharmaceutical composition is a liquid (e.g., aqueous solution) for intravenous injection. In certain embodiments, the pharmaceutical composition is a liquid (e.g., aqueous solution) for subcutaneous injection.

After formulation with an appropriate pharmaceutically acceptable excipient in a desired dosage, the pharmaceutical compositions of the present disclosure can be administered to humans and other animals orally, parenterally, intracisternally, intraperitoneally, topically, bucally, or the like, depending on the disease or condition being treated.

In certain embodiments, a pharmaceutical composition comprising a compound of Formula I is administered, orally or parenterally, at dosage levels of each pharmaceutical composition sufficient to deliver from about 0.001 mg/kg to about 200 mg/kg in one or more dose administrations for one or several days (depending on the mode of administration). In certain embodiments, the effective amount per dose varies from about 0.001 mg/kg to about 200 mg/kg, about 0.001 mg/kg to about 100 mg/kg, about 0.01 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, of subject body weight per day, one or more times a day, to obtain the desired therapeutic and/or prophylactic effect. In certain embodiments, the compounds described herein may be at dosage levels sufficient to deliver from about 0.001 mg/kg to about 200 mg/kg, from about 0.001 mg/kg to about 100 mg/kg, from about 0.01 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic and/or prophylactic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations). In certain embodiments, the composition described herein is administered at a dose that is below the dose at which the agent causes non-specific effects.

In certain embodiments, the pharmaceutical composition is administered at a dose of about 0.001 mg to about 1000 mg per unit dose. In certain embodiments, the pharmaceutical composition is administered at a dose of about 0.01 mg to about 200 mg per unit dose. In certain embodiments, the pharmaceutical composition is administered at a dose of about 0.01 mg to about 100 mg per unit dose. In certain embodiments, pharmaceutical composition is administered at a dose of about 0.01 mg to about 50 mg per unit dose. In certain embodiments, the pharmaceutical composition is administered at a dose of about 0.01 mg to about 10 mg per unit dose. In certain embodiments, the pharmaceutical composition is administered at a dose of about 0.1 mg to about 10 mg per unit dose.

Pharmaceutical compositions described herein can be prepared by any method known in the art of pharmacology. In general, such preparatory methods include the steps of bringing the composition comprising a compound of Formula I into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite (aluminum silicate) and Veegum (magnesium aluminum silicate)), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g. polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g. Cremophor™) polyoxyethylene ethers, (e.g. polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F-68, Poloxamer-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazelnut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include, but are not limited to, pharmaceutically acceptable emulsions, microemulsions, solutions, suspensions, syrups, and elixirs. In addition to the active agents, the liquid dosage forms may contain inert diluents commonly used in the art such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can also include adjuvants such as wetting agents, emulsifying and suspending agents, sweetening, flavoring, and perfuming agents. In certain embodiments for parenteral administration, agents of the invention are mixed with solubilizing agents such CREMOPHOR EL® (polyethoxylated castor oil), alcohols, oils, modified oils, glycols, polysorbates, cyclodextrins, polymers, and combinations thereof.

Injectable preparations, for example, sterile injectable aqueous or oleaginous suspensions, may be formulated according to the known art using suitable dispersing or wetting agents and suspending agents. Sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Solid dosage forms for oral administration include capsules, tablets, pills, powders, and granules. In such solid dosage forms, the active agent is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active agents can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active agent may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets, and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Formulations suitable for topical administration include liquid or semi-liquid preparations such as liniments, lotions, gels, applicants, oil-in-water or water-in-oil emulsions such as creams, ointments, or pastes; or solutions or suspensions such as drops. Formulations for topical administration to the skin surface can be prepared by dispersing the drug with a dermatologically acceptable carrier such as a lotion, cream, ointment, or soap. Useful carriers are capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used. Ophthalmic formulation, ear drops, and eye drops are also contemplated as being within the scope of this invention. Additionally, the present disclosure contemplates the use of transdermal patches, which have the added advantage of providing controlled delivery of an agent to the body. Such dosage forms can be made by dissolving or dispensing the agent in the proper medium. Absorption enhancers can also be used to increase the flux of the agent across the skin. The rate can be controlled by either providing a rate controlling membrane or by dispersing the agent in a polymer matrix or gel.

Additionally, the carrier for a topical formulation can be in the form of a hydroalcoholic system (e.g., liquids and gels), an anhydrous oil or silicone based system, or an emulsion system, including, but not limited to, oil-in-water, water-in-oil, water-in-oil-in-water, and oil-in-water-in-silicone emulsions. The emulsions can cover a broad range of consistencies including thin lotions (which can also be suitable for spray or aerosol delivery), creamy lotions, light creams, heavy creams, and the like. The emulsions can also include microemulsion systems. Other suitable topical carriers include anhydrous solids and semisolids (such as gels and sticks); and aqueous based mousse systems.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound or pharmaceutical composition described herein. In certain embodiments, the kits are useful for treating a disease (e.g., proliferative disease, hematological cancer, autoimmune disease, inflammatory disease) in a subject in need thereof. In certain embodiments, the kits are useful for preventing a disease (e.g., proliferative disease, hematological cancer, autoimmune disease, inflammatory disease) in a subject in need thereof. In certain embodiments, the kits are useful for reducing the risk of developing a disease (e.g., proliferative disease, hematological cancer, autoimmune disease, inflammatory disease) in a subject in need thereof. In certain embodiments, the kits are useful for inhibiting the activity (e.g., aberrant activity, such as increased activity) of MALT1 in a subject or cell.

In certain embodiments, a kit described herein further includes instructions for using the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease (e.g., proliferative disease, hematological cancer, autoimmune disease, inflammatory disease) in a subject in need thereof. In certain embodiments, the kits and instructions provide for preventing a disease (e.g., proliferative disease, hematological cancer, autoimmune disease, inflammatory disease) in a subject in need thereof. In certain embodiments, the kits and instructions provide for reducing the risk of developing a disease (e.g., proliferative disease, hematological cancer, autoimmune disease, inflammatory disease) in a subject in need thereof. In certain embodiments, the kits and instructions provide for inhibiting the activity (e.g., aberrant activity, such as increased activity) of MALT1 in a subject or cell. A kit described herein may include one or more additional pharmaceutical agents described herein as a separate composition.

Methods of Treatment

In addition to acting as a scaffold protein within the CBM complex, MALT1 also has proteolytic activity that is constitutively activated in certain cancers, such as ABC-DLBCL. MALT1 inhibitors are known to inhibit ABC-DLBCL viability, making MALT1 inhibition an attractive method for the treatment of ABC-DLBCL. In addition, some ABC-DLBCL cells carry CARD11 activating mutations. Cells with these mutations are particularly sensitive to MALT1 inhibitors, while they are resistant to inhibitors of kinases upstream in the pathway (e.g., BTK). Thus, treatment of these cancers with MALT1 inhibitors may be particularly effective.

Dysregulation of MALT1 activity may also have a role in the development of other diseases, such as inflammatory and autoimmune diseases. These include, but are not limited to, rheumatoid arthritis, multiple sclerosis, psoriasis, systemic lupus, Sjögren's syndrome, Hashimoto's thyroiditis, inflammatory bowel diseases (e.g., Crohn's disease, ulcerative colitis), lupus erythematosus, chronic obstructive pulmonary disease, and psoriatic arthritis.

The present disclosure provides methods for treating MALT1-related diseases and disorders. In certain embodiments, the application provides a method of treating inflammation.

In certain embodiments, the application provides a method of treating an inflammatory disease. In certain embodiments, the application provides a method of treating an autoimmune disease. In certain embodiments, the application provides a method of treating a proliferative disease. In certain embodiments, the application provides a method of treating cancer. In certain embodiments, the application provides a method of treating a hematological cancer. In certain embodiments, the application provides a method of treating a lymphoid malignancy. In certain embodiments, the application provides a method of treating a leukemia, a lymphoma, or multiple myeloma. In certain embodiments, the application provides a method of treating non-Hodgkin's lymphoma. In certain embodiments, the application provides a method of treating mantle cell lymphoma. In certain embodiments, the application provides a method of treating DLBCL. In certain embodiments, the application provides a method of treating ABC-DLBCL. In certain embodiments, the application provides a method of treating ABC-DLBCL with CARD11 activating mutations.

The present disclosure provides methods of inhibiting the activity of MALT1. In certain embodiments, the application provides a method of inhibiting the activity of MALT1 in vitro. In certain embodiments, the application provides a method of inhibiting the activity of MALT1 in vivo. In certain embodiments, the application provides a method of inhibiting the activity of MALT1 in a cell. In certain embodiments, the application provides a method of inhibiting the activity of MALT1 in a human cell.

In certain embodiments, the methods comprise administering to a subject in need thereof (e.g., a subject with a cancer) a compound that interacts with MALT1, for example, a compound that is an inhibitor of MALT1, a modulator of MALT1, a binder of MALT1, or a compound that modifies MALT1. The compound may interact, inhibit, modulate, and/or modify MALT1 by binding to an allosteric site of MALT1. In certain embodiments, the methods comprise administering a compound of Formula I, or a pharmaceutically acceptable salt, co-crystal, tautomer, stereoisomer, solvate, hydrate, polymorph, isotopically enriched derivative, or prodrug, or composition thereof, to a subject in need thereof. In some embodiments, the method comprises administering a pharmaceutical composition comprising a compound of Formula I, or a pharmaceutically acceptable salt, co-crystal, tautomer, stereoisomer, solvate, hydrate, polymorph, isotopically enriched derivative, or prodrug, or composition thereof, to a subject in need thereof.

The present disclosure also provides a compound of Formula I, or a pharmaceutically acceptable salt, co-crystal, tautomer, stereoisomer, solvate, hydrate, polymorph, isotopically enriched derivative, or prodrug, or composition thereof, for use in the treatment of a cancer. In certain embodiments, the cancer is a hematological cancer. In certain embodiments, the cancer is a lymphoid malignancy. In certain embodiments, the cancer is a leukemia, a lymphoma, or multiple myeloma. In certain embodiments, the cancer is a non-Hodgkin's lymphoma. In certain embodiments, the cancer is a mantle cell lymphoma. In certain embodiments, the cancer DLBCL. In certain embodiments, the cancer is ABC-DLBCL. In certain embodiments, the cancer is ABC-DLBCL with CARD11 activating mutations.

The present disclosure also provides uses of a compound of Formula I, or a pharmaceutically acceptable salt, co-crystal, tautomer, stereoisomer, solvate, hydrate, polymorph, isotopically enriched derivative, or prodrug, or composition thereof, in the manufacture of a medicament for the treatment of a cancer. In certain embodiments, the cancer is a hematological cancer. In certain embodiments, the cancer is a lymphoid malignancy. In certain embodiments, the cancer is a leukemia, a lymphoma, or multiple myeloma. In certain embodiments, the cancer is a non-Hodgkin's lymphoma. In certain embodiments, the cancer is a mantle cell lymphoma. In certain embodiments, the cancer is DLBCL. In certain embodiments, the cancer is ABC-DLBCL. In certain embodiments, the cancer is ABC-DLBCL with CARD11 activating mutations.

In certain embodiments, the methods disclosed herein comprise administering to the subject an effective amount of a compound of Formula I, or a pharmaceutically acceptable salt, co-crystal, tautomer, stereoisomer, solvate, hydrate, polymorph, isotopically enriched derivative, or prodrug, or composition thereof. In some embodiments, the effective amount is a therapeutically effective amount. In some embodiments, the effective amount is a prophylactically effective amount.

In certain embodiments, the subject being treated is an animal. The animal may be of either sex and may be at any stage of development. In certain embodiments, the subject is a mammal. In certain embodiments, the subject being treated is a human. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the animal is a genetically engineered animal. In certain embodiments, the animal is a transgenic animal.

Certain methods described herein may comprise administering one or more additional pharmaceutical agent(s) in combination with the compounds described herein. The additional pharmaceutical agent(s) may be administered at the same time as the compound of Formula I, or at different times than the compound of Formula I. For example, the compound of Formula I and any additional pharmaceutical agent(s) may be on the same dosing schedule or different dosing schedules. All or some doses of the compound of Formula I may be administered before all or some doses of an additional pharmaceutical agent, after all or some does an additional pharmaceutical agent, within a dosing schedule of an additional pharmaceutical agent, or a combination thereof. The timing of administration of the compound of Formula I and additional pharmaceutical agents may be different for different additional pharmaceutical agents.

In certain embodiments, the additional pharmaceutical agent comprises an agent useful in the treatment of a proliferative disease. In certain embodiments, the additional pharmaceutical agent comprises an agent useful in the treatment of cancer. In certain embodiments, the additional pharmaceutical agent is useful in the treatment of a hematological cancer. In certain embodiments, the additional pharmaceutical agent cancer is is useful in the treatment of a lymphoid malignancy. In certain embodiments, the additional pharmaceutical agent is useful in the treatment of a leukemia, a lymphoma, or multiple myeloma. In certain embodiments, the additional pharmaceutical agent is useful in the treatment of a non-Hodgkin's lymphoma. In certain embodiments, the additional pharmaceutical agent is useful in the treatment of mantle cell lymphoma. In certain embodiments, the additional pharmaceutical agent is useful in the treatment of DLBCL. In certain embodiments, the additional pharmaceutical agent is useful in the treatment of ABC-DLBCL. In certain embodiments, the additional pharmaceutical agent is an anti-cancer agent. In certain embodiments, the additional pharmaceutical agent is any anti-cancer agent recited herein. In certain embodiments, the additional pharmaceutical agent is an immunotherapy. In certain embodiments, the additional pharmaceutical agent is any immunotherapy recited herein.

EXAMPLES

In order that the invention described herein may be more fully understood, the following examples are set forth. The examples described in this application are offered to illustrate the compounds, pharmaceutical compositions, and methods provided herein and are not to be construed in any way as limiting their scope.

Compounds of Formula I were prepared using the synthetic schemes and procedures described in detail below.

Preparation of Synthetic Intermediates

4-Bromo-6-chloroquinolin-3-amine (E)

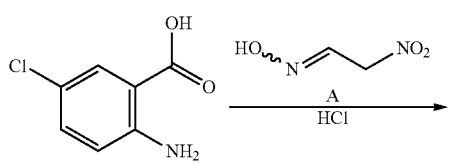

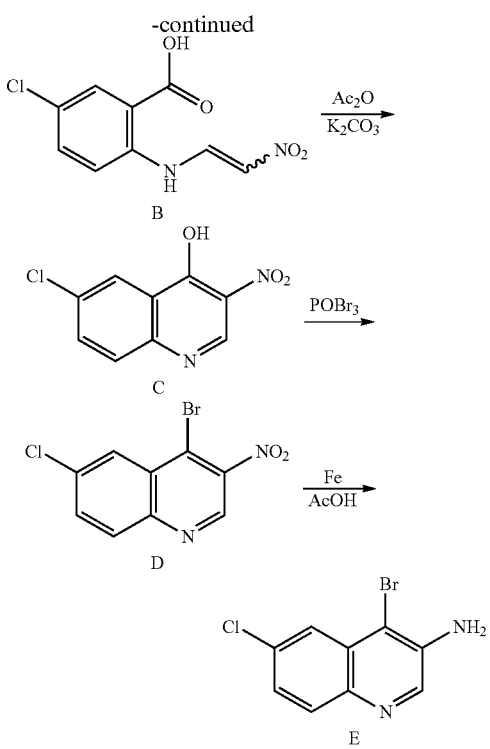

5-Chloro-2-(2-nitrovinylamino)benzoic Acid (B)

Nitromethane (26.8 g, 440 mmol) was added dropwise to a solution of NaOH (26.8 g, 670 mmol) in water (60 mL) while keeping the temperature at 20-30° C. The resulting mixture was then warmed to 40° C. and stirred for 10 min. The mixture was cooled to 20-30° C. and another portion of nitromethane (13.4 g, 220 mmol) was added. After complete addition, the reaction was stirred for 1 hour at 45° C. The red solution was then heated to 50-55° C. and cooled to 30° C. immediately to give oxime A as a solution, which was used directly in the next step.

The solution of oxime A was acidified with conc. HCl (60 mL), and added to a suspension of 2-amino-5-chloro-benzoic acid (34.3 g, 200 mmol) in conc. HCl (85 mL) and water (860 mL). The reaction mixture was stirred for 18 hours at room temperature, and the yellow precipitate collected by filtration, washed with water (2×100 mL) and dried to give the title compound (48.0 g, 99% yield). $^1$H NMR (400 MHz, CDCl$_3$): δ 14.15 (bs, 1H), 12.98 (d, 1H), 8.06 (dd, 1H), 7.96 (s, 1H), 7.80 (d, 1H), 7.76 (d, 1H), 6.78 (d, 1H)

6-Chloro-3-nitroquinolin-4-ol (C)

Potassium carbonate (11.3 g, 82 mmol) and 5-chloro-2-(2-nitrovinylamino)benzoic acid (6.6 g, 27.2 mmol) were suspended in acetic anhydride (70 mL). The resulting mixture was heated at 90° C. for 1 hour. After cooling, a yellow precipitate formed, which was collected by filtration, washed with acetic acid and water, dried to give the title compound (3.4 g, 56% yield). $^1$H NMR (400 MHz, DMSO-d$_6$): δ 13.19 (bs, 1H), 9.24 (s, 1H), 8.18 (d, 1H), 7.85 (dd, 1H), 7.76 (d, 1H). MS m/z 225.38 [M+H]$^+$.

4-Bromo-6-chloro-3-nitroquinoline (D)

POBr$_3$ (7.0 g, 25 mmol) and DIPEA (4.3 g, 33 mmol) were added to a suspension of 6-chloro-3-nitroquinolin-4-ol (3.7 g, 16.5 mmol) in acetonitrile (50 mL). The resulting solution was heated under reflux for 1 hour. The solvents were removed under reduced pressure, and the residue was purified by silica chromatography (hexane:EtOAc=5:1 to 1:1) to give the title compound (3.3 g, 70% yield). $^1$H NMR (400 MHz, CDCl$_3$): δ 9.17 (s, 1H), 8.44 (d, 1H), 8.28 (d, 1H), 7.92 (dd, 1H). MS m/z 287.31 [M+H]$^+$.

4-Bromo-6-chloroquinolin-3-amine (E)

Iron powder (5.24 g, 94 mmol) was added to the suspension of 4-bromo-6-chloro-3-nitroquinoline (2.7 g, 9.4 mmol) in acetic acid (50 mL). The mixture was stirred and heated at 60° C. for 3 hours. The mixture was diluted with EtOAc (100 mL), filtered through a Celite pad, and washed with EtOAc. The combined filtrates were concentrated and the residue was purified by silica chromatography (hexane:EtOAc=2:1 to 1:1) to give the title compound (2.0 g, 83% yield). $^1$H NMR (400 MHz, DMSO-d$_6$): δ 8.51 (s, 1H), 7.87 (d, 1H), 7.79 (d, 1H), 7.44 (dd, 1H), 6.30 (bs, 2H).

Quinoline amines F, G, and H were prepared with methods analogous to that used for preparing quinoline amine E, from the corresponding aminobenzoic acids as indicated in the table below.

| Quinoline amine | Structure/Name | m/z [M + 1]$^+$ | Starting material |
|---|---|---|---|
| F | 4-Bromo-6-fluoroquinolin-3-amine | 242.72 | 2-amino-5-fluorobenzoic acid |
| G | 4-Bromo-6-methoxyquinolin-3-amine | 254.74 | 2-amino-5-methoxybenzoic acid |
| H | 4-Bromo-6-methylquinolin-3-amine | 238.6 | 2-amino-5-methylbenzoic acid |

4-(2-Methoxypropan-2-yl)quinolin-3-amine (L)

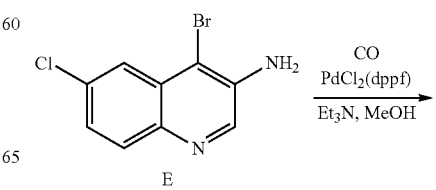

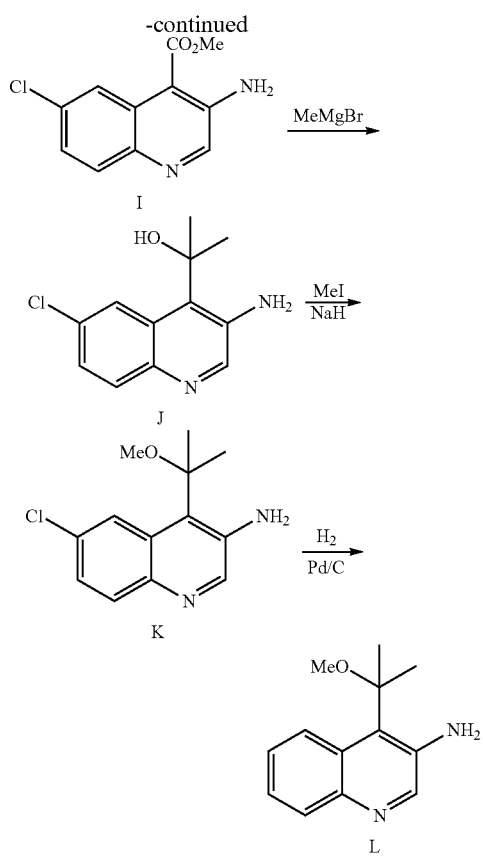

Methyl 3-amino-6-chloro-quinoline-4-carboxylate (I)

A mixture of 4-bromo-6-chloroquinolin-3-amine (7.60 g, 29.5 mmol), triethylamine (3.28 g, 32.5 mmol) and PdCl$_2$ (dppf) (4.31 g, 5.9 mmol) was suspended in a mixture of MeOH (300 mL) and THF (30 mL) in an autoclave. The mixture was stirred under 30 atm CO for 18 hours at 100° C. then cooled to room temperature and concentrated. The residue was purified by silica chromatography (DCM: MeOH=100:1 to 50:1) to give the title compound (6.05 g, 86% yield). $^1$H NMR (400 MHz, DMSO-d$_6$): δ 8.63 (s, 1H), 8.44 (d, 1H), 7.82 (d, 1H), 7.39 (m, 1H), 7.21 (bs, 2H), 3.94 (s, 3H).

2-(3-Amino-6-chloro-4-quinolyl)propan-2-ol (J)

Methylmagnesium bromide (3M in ethyl ether, 22.6 mL, 67.6 mmol, 10 eq) was added dropwise to a solution of methyl 3-amino-6-chloro-quinoline-4-carboxylate (1.60 g, 6.7 mmol) in THF (50 mL) at 0° C. After complete addition, the resulting mixture was stirred overnight at room temperature, then quenched with saturated NH$_4$Cl solution (50 mL). The mixture was extracted with EtOAc (2×50 mL). The combined organic phases were combined, washed with brine, dried (Na$_2$SO$_4$) and concentrated. The residue was purified by silica chromatography (DCM:MeOH=100:1 to 20:1) to give the title compound (750 mg, 47% yield). $^1$H NMR (400 MHz, DMSO-d$_6$): δ 8.37 (s, 1H), 8.12 (d, 1H), 7.76 (d, 1H), 7.28 (dd, 1H), 6.30 (bs, 2H), 1.74 (s, 6H).

6-Chloro-4-(2-methoxypropan-2-yl)quinolin-3-amine (K)

NaH (60% suspension in oil, 152 mg, 6.3 mmol) was added to the solution of 2-(3-amino-6-chloro-4-quinolyl)propan-2-ol (750 mg, 3.2 mmol) in THF (20 mL) at 0° C. under N$_2$ and stirred for 30 min. Iodomethane (675 mg, 4.8 mmol) was added and the resulting mixture was stirred overnight at room temperature, then quenched with saturated NH$_4$Cl solution (50 mL). The mixture was extracted with EtOAc (3×50 mL). The organics were combined, washed with brine, dried (Na$_2$SO$_4$) and concentrated. The residue was purified by silica chromatography (DCM:MeOH=100:1 to 30:1) to give the title compound (410 mg, 51% yield). $^1$H NMR (400 MHz, DMSO-d$_6$): δ 8.44 (s, 1H), 8.34 (d, 1H), 7.77 (d, 1H), 7.32 (dd, 1H), 5.92 (bs, 2H), 2.98 (s, 3H), 1.75 (s, 6H). MS m/z 251.4 [M+H]$^+$.

4-(2-Methoxypropan-2-yl)quinolin-3-amine (L)

10% Pd/C (50 mg) was added to a solution of 6-chloro-4-(2-methoxypropan-2-yl)quinolin-3-amine (K) (200 mg, 0.8 mmol) and triethylamine (161 mg, 1.6 mmol) in EtOH (20 mL). The reaction mixture was stirred under hydrogen atmosphere for 1.5 hours then filtered. The filtrate was concentrated under reduced pressure and the residue purified by silica chromatography (hexane:EtOAc=3:1 to 1:1) to give the title compound (160 mg, 93% yield). $^1$H NMR (400 MHz, CDCl$_3$): δ 8.44 (s, 1H), 8.09 (m, 1H), 8.02 (m, 1H), 7.41 (m, 2H), 5.30 (br, 2H), 3.20 (s, 3H), 1.91 (s, 6H). MS m/z 217.22 [M+H]$^+$.

Quinoline amines M and N were prepared with methods analogous to that used for preparing quinoline amine K, from the corresponding quinoline amines as indicated in the table below.

| Quinoline amine | Structure/Name | m/z [M + 1]$^+$ | Starting material |
|---|---|---|---|
| M | ![structure] 6-Fluoro-4-(2-methoxypropan-2-yl)quinolin-3-amine | 235.1 | 4-Bromo-6-fluoroquinolin-3-amine (F) |
| N | ![structure] 4-(2-Methoxypropan-2-yl)-6-methylquinolin-3-amine | 231.2 | 4-Bromo-6-methylquinolin-3-amine (H) |

4-Bromo-7-chloroquinolin-3-amine (Q)

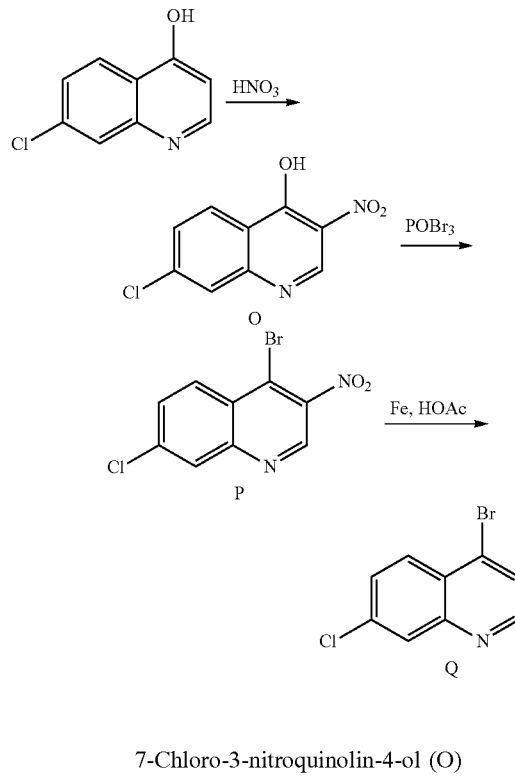

7-Chloro-3-nitroquinolin-4-ol (O)

Conc. nitric acid (66%, 3.6 mL) was added dropwise to a solution of 7-chloro-quinolin-4-ol (2.55 g, 14.3 mmol) in propionic acid (26 mL) at 90° C. The mixture was stirred and heated under reflux for 3 hours. The reaction mixture was cooled, filtered, and the precipitate was washed with water (3×10 mL) and dried to give the title compound (2.40 g, 74% yield) as a yellow solid. $^1$H NMR (400 MHz, DMSO-$d_6$): δ 13.03 (bs, 1H), 9.27 (s, 1H), 8.25 (d, 1H), 7.77 (d, 1H), 7.56 (dd, 1H).

4-Bromo-7-chloro-3-nitroquinoline (P)

POBr$_3$ (2.3 g, 8 mmol) and DIPEA (1.4 g, 10.7 mmol) were added to a suspension of 7-chloro-3-nitroquinolin-4-ol (1.2 g, 5.4 mmol) in acetonitrile (25 mL). The resulting solution was heated under reflux for 1 hour. The solvent was removed under reduced pressure, and the residue was purified by silica chromatography (hexane:EtOAc=5:1 to 1:1) to give the title compound (590 mg, 38% yield). $^1$H NMR (400 MHz, DMSO-$d_6$): δ 9.33 (s, 1H), 8.42 (d, 1H), 8.33 (d, 1H), 8.00 (dd, 1H).

4-Bromo-7-chloroquinolin-3-amine (Q)

Iron powder (2.3 g, 4.2 mmol) was added to the suspension of 4-bromo-7-chloro-3-nitroquinoline (1.2 g, 4.2 mmol) in acetic acid (20 mL), The mixture was stirred and heated at 60° C. for 3 hours then diluted with EtOAc (100 mL), filtered through a Celite pad, and washed with EtOAc. The combined filtrates were concentrated and the residue was purified by silica chromatography (hexane:EtOAc=2:1 to 1:1) to give the title compound (440 mg, 41% yield). MS m/z 257.07 [M+H]$^+$.

4-Bromo-7-methoxyquinolin-3-amine (R)

4-Bromo-7-methoxyquinolin-3-amine (R) was prepared from 7-methoxy-quinolin-4-ol with a method analogous to that used for preparing 4-bromo-7-chloroquinolin-3-amine (Q). MS m/z 252.90 [M+H]$^+$.

4-Isopropylquinolin-3-amine (U)

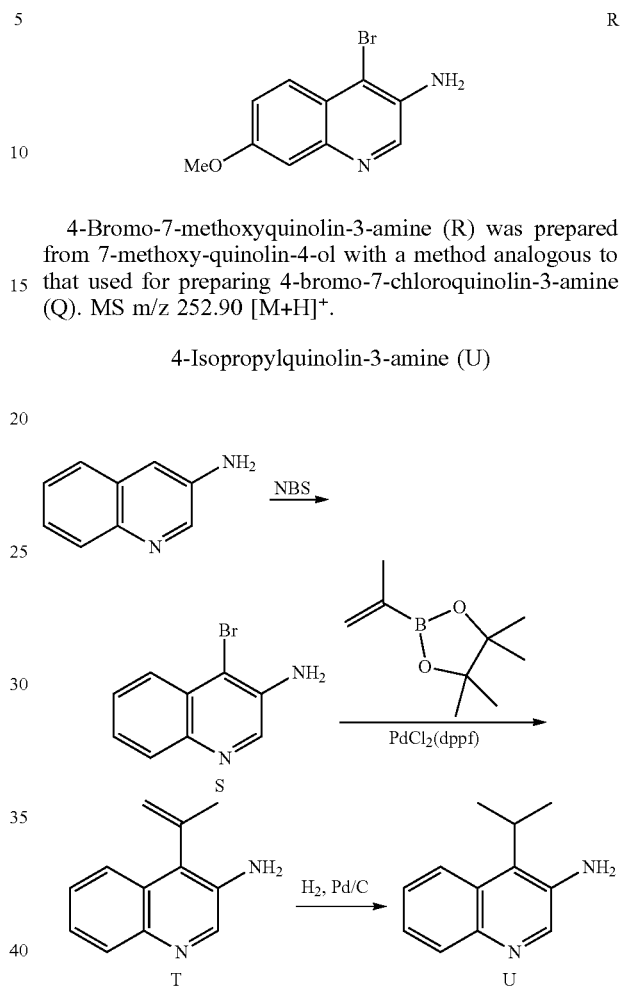

4-Bromoquinolin-3-amine (S)

NBS (4.62 g, 26 mmol) was added to a solution of quinolin-3-amine (3.40 g, 23.5 mmol) in DMF (20 mL) and the mixture stirred for 1 hour, then quenched with water (100 mL). The resulting mixture was extracted with EtOAc (3×100 mL) and the combined organic layers washed with brine, dried (Na$_2$SO$_4$) and concentrated under reduced pressure. The residue was purified by silica chromatography (hexane:EtOAc=10:1) to give the title compound (3.80 g, 72% yield) as a brown solid. $^1$H NMR (400 MHz, DMSO-$d_6$): δ 8.54 (s, 1H), 7.83 (m, 2H), 7.56 (m, 1H), 7.44 (m, 1H), 6.06 (bs, 2H).

4-(Prop-1-en-2-yl)quinolin-3-amine (T)

2-Isopropenyl-4,4,5,5-tetramethyl-1,3,2-dioxaborolane (564 mg, 3 mmol), Cs$_2$CO$_3$ (1.46 g, 4.5 mmol) and PdCl$_2$(dppf) (163 mg) were added to a solution of 4-bromoquinolin-3-amine (500 mg, 2.2 mmol) in dioxane (20 mL) and water (5 mL). The reaction mixture was stirred at 80° C. for 4 hours under a N$_2$ atmosphere. After cooling, the mixture was diluted with water (100 mL), extracted with EtOAc (3×200 mL) and the combined organic phases washed with aq. HCl (1N), saturated NaHCO$_3$ solution and brine. The organic phase was dried (Na$_2$SO$_4$), concentrated and the residue was purified by silica chromatography (hexane: EtOAc=30:1 to 10:1) to give the title compound (430 g, ~100% yield, contained dppf) as a yellow oil. MS m/z 185.34 [M+H]$^+$.

4-Isopropylquinolin-3-amine (U)

Pd/C (10%, 150 mg) was added to a solution of 4-(prop-1-en-2-yl)quinolin-3-amine (180 mg, 1 mmol) in EtOH (10 mL) and stirred for 4 hours under a hydrogen atmosphere. The reaction mixture was filtered and concentrated to give the title compound (65 mg, 37% yield) as a clear yellow oil. MS m/z 187.23 [M+H]$^+$.

4-Cyclopentylquinolin-3-amine (W)

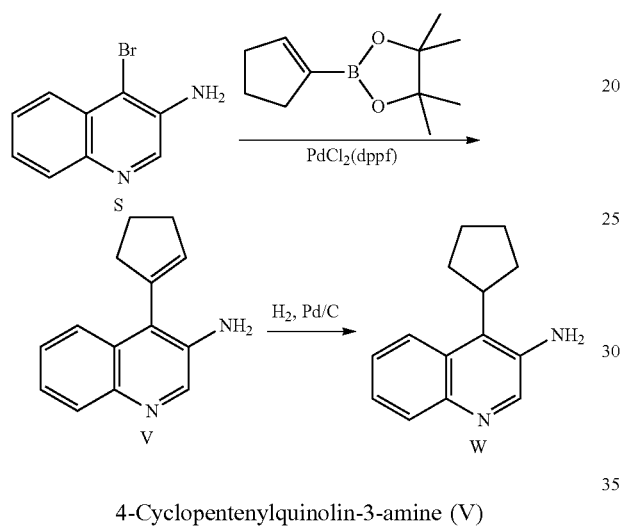

4-Cyclopentenylquinolin-3-amine (V)

4-Cyclopentenylquinolin-3-amine was prepared in a similar manner to 4-(prop-1-en-2-yl)quinolin-3-amine (T) from 4-bromoquinolin-3-amine (S) and 2-cyclopentenyl-4,4,5,5-tetramethyl-1,3,2-dioxaborolane. $^1$H NMR (400 MHz, CDCl$_3$): δ 8.55 (s, 1H), 7.99 (m, 1H), 7.64 (m, 1H), 7.45 (m, 2H), 5.92 (m, 1H), 3.90 (bs, 2H), 2.75 (m, 4H), 2.15 (m, 2H). MS m/z 211.24 [M+H]$^+$.

4-Cyclopentylquinolin-3-amine (W)

4-Cyclopentylquinolin-3-amine was prepared with a method analogous to that used for preparing 4-isopropylquinolin-3-amine (U) from 4-cyclopentenylquinolin-3-amine (V). MS m/z 213.22 [M+H]$^+$.

Quinoline amines X-EE in the table below were prepared by methods analogous to those used for preparing 4-(prop-1-en-2-yl)quinolin-3-amine (T) from the indicated bromoquinoline and boronic acid in the table below.

| Quinoline amine | Structure/Name | m/z [M + 1]$^+$ | Starting material |
|---|---|---|---|
| X | 4-cyclopropylquinolin-3-amine | — | 4-Bromoquinolin-3-amine/ cyclopropylboronic acid |
| Y | 4-Cyclopropyl-6-fluoroquinolin-3-amine | 203.27 | 4-Bromo-6-fluoroquinolin-3-amine/ cyclopropylboronic acid |
| Z | 6-Chloro-4-cyclopropylquinolin-3-amine | 218.92 | 4-Bromo-6-chloroquinolin-3-amine/ cyclopropylboronic acid |
| AA | 7-Chloro-4-cyclopropylquinolin-3-amine | 218.86 | 7-Chloro-4-bromoquinolin-3-amine/ cyclopropylboronic acid |
| BB | 4-Cyclopropyl-6-methoxyquinolin-3-amine | 215.24 | 4-Bromo-6-methoxyquinolin-3-amine/ cyclopropylboronic acid |
| CC | 4-Cyclopropyl-7-methoxyquinolin-3-amine | 214.99 | 4-Bromo-7-methoxyquinolin-3-amine/ cyclopropylboronic acid |
| DD | 4-(Thiazol-5-yl)quinolin-3-amine | — | 4-Bromoquinolin-3-amine/ thiazol-5-ylboronic acid |

| Quinoline amine | Structure/Name | m/z [M + 1]+ | Starting material |
|---|---|---|---|
| EE | 4-(Furan-2-yl)quinolin-3-amine | — | 4-Bromoquinolin-3-amine/ furan-2-ylboronic acid |

4-(Trifluoromethyl)quinoline-3-carboxylic acid (II)

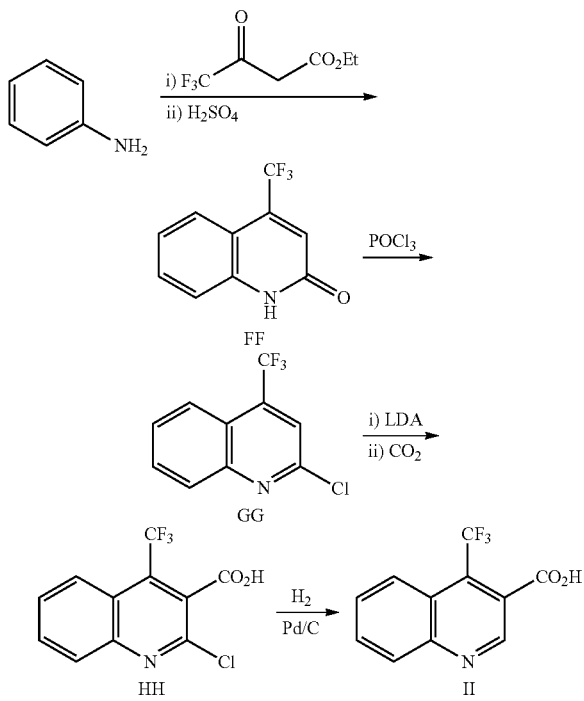

4-(Trifluoromethyl)quinolin-2(1H)-one (FF)

A mixture of aniline (9.30 g, 100 mmol) and ethyl 4,4,4-trifluoro-3-oxobutanoate (36.8 g, 200 mmol) was stirred at 110° C. for 1 hour. The reaction mixture was concentrated under reduced pressure, and then diluted with water (20 mL). Conc. $H_2SO_4$ (110 g, 1.13 mol) was added carefully and the mixture stirred at 90° C. for 1 hour, then cooled to room temperature and poured into ice water (500 mL). The precipitate was collected by filtration, and then recrystallised from ethanol (50 mL) to give the title compound (9.90 g, 46.5% yield) as a white solid. $^1$H NMR (400 MHz, DMSO-$d_6$): δ 12.34 (bs, 1H), 7.75 (m, 2H), 7.45 (d, 1H), 7.32 (m, 1H), 6.99 (s, 1H). MS m/z 214.20 [M+H]+.

2-Chloro-4-(trifluoromethyl)-1,2-dihydroquinoline (GG)

A mixture of 4-(trifluoromethyl)quinolin-2(1H)-one (4.40 g, 20.6 mmol) and POCl$_3$ (6.33 g, 41.3 mmol) was heated under reflux for 2 hours, cooled and poured into ice water (100 mL). The mixture was extracted with ethyl acetate (3×100 mL) and the combined organic layers were washed with water, saturated NaHCO$_3$ solution and brine, dried (Na$_2$SO$_4$) and concentrated to give the title compound (4.80 g, ~100% yield), which was used without further purification. $^1$H NMR (400 MHz, DMSO-$d_6$): δ 8.12 (m, 2H), 8.00 (m, 1H), 7.87 (m, 1H). MS m/z 232.15 [M+H]+.

2-Chloro-4-(trifluoromethyl)quinoline-3-carboxylic acid (HH)

LDA (1N, 13 mL, 13 mmol) was added dropwise to a solution of 2-chloro-4-(trifluoromethyl)-1,2-dihydroquinoline (2.00 g, 8.6 mmol) in dry THF (50 mL) at −78° C. The mixture was stirred at −78° C. for 1 hour then dry ice was added. The mixture was then allowed to warm to room temperature, quenched with water (100 mL) and acidified (pH 3~4) with 1 N HCl. The mixture was extracted with ethyl acetate (3×100 m) and the combined organic layers washed with brine, dried (Na$_2$SO$_4$) and concentrated to give the title compound (2.20 g, 92% yield) as a brown solid which was used without further purification. $^1$H NMR (400 MHz, DMSO-$d_6$): δ 8.18 (m, 2H), 8.05 (m, 1H), 7.92 (m, 1H). MS m/z 276.01 [M+H]+.

4-(Trifluoromethyl)quinoline-3-carboxylic acid (II)

Pd/C (10%, 0.5 g) and triethylamine (600 mg, 6 mmol) were added to a solution of 2-chloro-4-(trifluoromethyl) quinoline-3-carboxylic acid (1.10 g, 4 mmol) in ethanol (100 mL). The mixture was stirred for 4 hours under 1 atm H$_2$ then filtered, and the filtrate was concentrated to give the title compound (890 mg, 92% yield). MS m/z 240.16 [M+H]+.

4-Methylquinoline-3-carboxylic acid (KK)

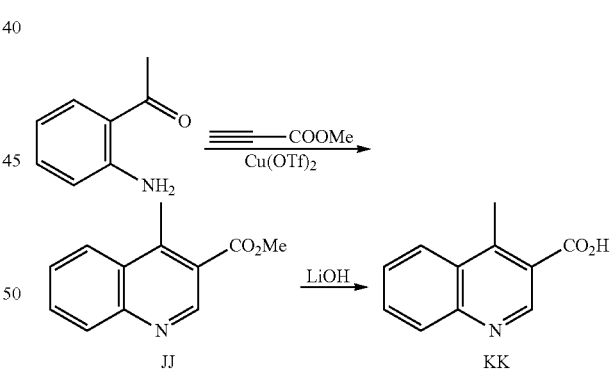

Methyl 4-methylquinoline-3-carboxylate (JJ)

Copper (II) trifluoromethanesulfonate (700 mg, 21 mmol) was added to a solution of 1-(2-aminophenyl)ethanone (2.90 g, 21 mmol) and methyl prop-2-ynoate (1.80 g, 21 mmol) in toluene (50 mL), and the reaction mixture was heated under reflux for 2 hours under nitrogen. After cooling, the solvent was removed under reduced pressure and the residue was purified by silica chromatography to give the title compound (380 mg, 9% yield). $^1$H NMR (400 MHz, DMSO-$d_6$): δ 9.11 (s, 1H), 8.32 (d, 1H), 8.07 (d, 1H), 7.90 (m, 1H), 7.74 (m, 1H), 3.97 (s, 3H), 2.93 (s, 3H). MS m/z 202.04 [M+H]+.

4-Methylquinoline-3-carboxylic acid (KK)

A solution of lithium hydroxide hydrate (200 mg, 4.8 mmol) in water (5 mL) was added to a solution of methyl 4-methylquinoline-3-carboxylate (400 mg, 2.0 mmol) in THF (10 mL). The reaction mixture was stirred at room temperature for 2 hours then diluted with water (20 mL). The mixture was washed with hexane/EtOAc (1:1, 3×20 mL) and the aqueous phase acidified (pH 4-5) with 1 N aq. HCl and extracted with ethyl acetate (6×50 mL). The combined organic layers were washed with brine, dried ($Na_2SO_4$) and concentrated to give the title compound (270 mg, 73% yield) as a yellow solid. MS m/z 188.30 $[M+H]^+$.

4-Cyclopropyl-7-fluoroquinoline-3-carboxylicacid (OO)

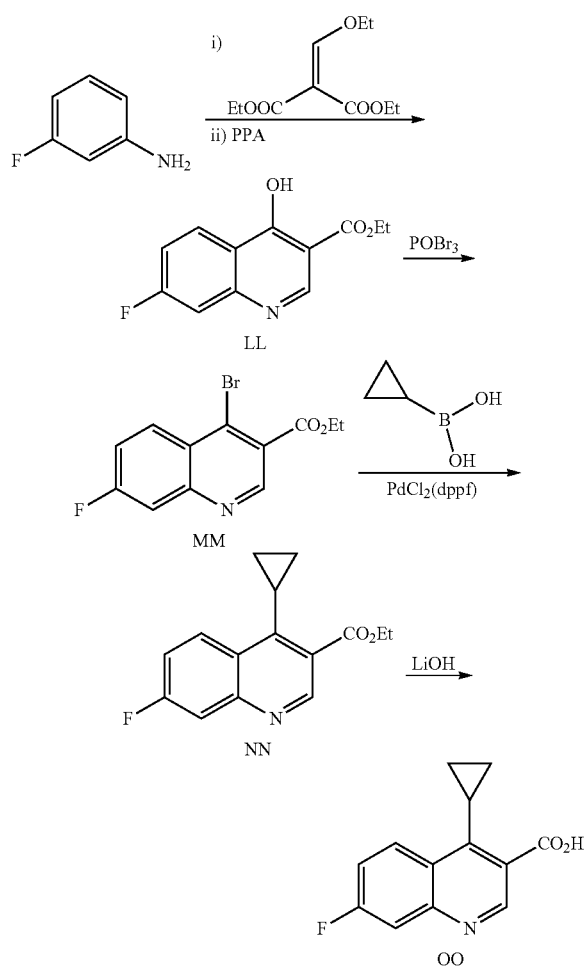

Ethyl 7-fluoro-4-hydroxyquinoline-3-carboxylate (LL)

3-Fluoroaniline (10.0 g, 90 mmol) and diethyl ethoxymethylene malonate (21.6 g, 100 mmol) were dissolved in EtOH (500 mL), the mixture was heated under reflux for 3 hours, cooled and allowed to stand at room temperature overnight. The solid precipitate was collected by filtration, dried under vacuum, and suspended in polyphosphoric acid (40 mL). $POCl_3$ (2.0 g, 12.9 mmol) was added and the mixture was stirred at 75° C. for 8 hours. After cooling, the mixture was poured into ice-water (500 mL), extracted with EtOAc (3×300 mL), and the combined organic layers washed with brine, dried ($Na_2SO_4$) and concentrated. The residue was purified by silica chromatography (DCM:MeOH=100:1 to 30:1) to give the title compound (3.8 g, 18% yield). $^1$H NMR (400 MHz, DMSO-$d_6$): δ 12.33 (bs, 1H), 8.59 (s, 1H), 8.20 (m, 1H), 7.42 (m, 1H), 6.95 (m, 1H), 4.22 (q, 2H), 1.28 (t, 3H). MS m/z 235.79 $[M+H]^+$.

Ethyl 4-bromo-7-fluoroquinoline-3-carboxylate (MM)

$POBr_3$ (6.88 g, 24 mmol) was added to a suspension of ethyl 7-fluoro-4-hydroxyquinoline-3-carboxylate (3.8 g, 16 mmol) and DIPEA (4.1 g, 32 mmol) in acetonitrile (50 mL). The resulting solution was heated under reflux for 2 hours. The solvent was removed under reduced pressure, and the residue was purified by silica chromatography (hexane:EtOAc=20:1 to 10:1) to give the title compound (3.5 g, 73% yield). $^1$H NMR (400 MHz, $CDCl_3$): δ 9.10 (s, 1H), 8.44 (m, 1H), 7.77 (m, 1H), 7.49 (m, 1H), 4.52 (q, 2H), 1.47 (t, 3H).

Ethyl 4-cyclopropyl-7-fluoroquinoline-3-carboxylate (NN)

Cyclopropylboronic acid (580 mg, 6.75 mmol), $Cs_2CO_3$ (2.2 g, 6.70 mmol) and $PdCl_2$(dppf) (120 mg) were added to a solution of ethyl 4-bromo-7-fluoroquinoline-3-carboxylate (1.0 g, 3.35 mmol) in dioxane (100 mL) and water (20 mL). The reaction mixture was stirred at 80° C. for 4 hours under a $N_2$ atmosphere then cooled to room temperature, diluted with water (100 mL) and extracted with EtOAc (3×200 mL). The combined organic phases were washed with aq. HCl (1N), saturated $NaHCO_3$ solution and brine, dried ($Na_2SO_4$), and concentrated. The residue was purified by silica chromatography (hexane:EtOAc=30:1 to 10:1) to give the title compound (480 mg, 54% yield). $^1$H NMR (400 MHz, DMSO-$d_6$): δ 8.95 (s, 1H), 8.65 (m, 1H), 7.84 (m, 1H), 7.68 (m, 1H), 4.40 (q, 2H), 2.45 (m, 1H), 1.38 (t, 3H), 1.20 (m, 2H), 0.52 (m, 2H).

4-Cyclopropyl-7-fluoroquinoline-3-carboxylic acid (OO)

A solution of $LiOH.H_2O$ (180 mg, 4.3 mmol) in water (5 mL) was added to a solution of ethyl 4-cyclopropyl-7-fluoroquinoline-3-carboxylate (470 mg, 1.8 mmol) in THF (100 mL). The mixture was stirred at 50° C. for 3 hours, the mixture was adjusted to pH 5 with 1N aq. HCl then concentrated to give the title compound (500 mg, ~100% yield, contained LiCl), which was used without further purification. $^1$H NMR (400 MHz, DMSO-$d_6$): δ 13.51 (bs, 1H), 8.95 (s, 1H), 8.64 (m, 1H), 7.82 (m, 1H), 7.68 (m, 1H), 2.45 (m, 1H), 1.23 (m, 2H), 0.56 (m, 2H).

4-Acetylquinoline-3-carboxylic acid (RR)

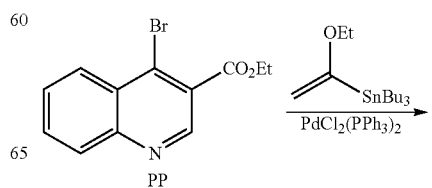

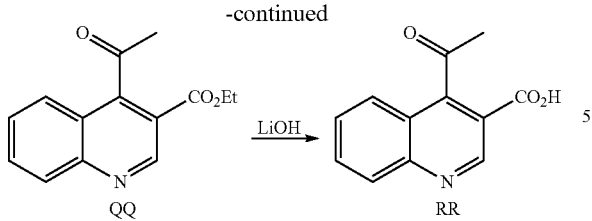

Ethyl 4-bromoquinoline-3-carboxylate (PP)

Ethyl 4-bromoquinoline-3-carboxylate was prepared from aniline with a method analogous to that used to prepare ethyl 4-bromo-7-fluoroquinoline-3-carboxylate (MM). $^1$H NMR (400 MHz, CDCl$_3$): δ 9.10 (s, 1H), 8.44 (m, 1H), 8.17 (m, 1H), 7.87 (m, 1H), 7.75 (m, 1H), 4.52 (q, 2H), 1.48 (t, 3H).

Ethyl 4-acetylquinoline-3-carboxylate (QQ)

PdCl$_2$(PPh$_3$)$_2$ (100 mg) was added to a solution of ethyl 4-bromoquinoline-3-carboxylate (411 mg, 1.47 mmol) and tributyl (1-ethoxyvinyl) stannane (1.22 g, 2.51 mmol) in DMF (30 mL) under nitrogen. After completion of the reaction (by TLC), the resulting mixture was quenched with water and extracted (EtOAc). The combined organic layers were washed with sat. NaHCO$_3$ solution, brine, dried over anhydrous sodium sulfate and concentrated. The residue was treated with aq. 2N HCl: dioxane (40 mL, 1:1) overnight, then concentrated and purified by silica chromatography (hexane:EtOAc=20:1 to 3:1) to give the title compound (310 mg). $^1$H NMR (400 MHz, CDCl$_3$): δ 9.50 (s, 1H), 8.38 (m, 1H), 7.95 (m, 1H), 7.80 (m, 1H), 7.75 (m, 1H), 4.48 (q, 2H), 2.72 (s, 3H), 1.46 (t, 3H).

4-Acetylquinoline-3-carboxylic acid (RR)

4-Acetylquinoline-3-carboxylic acid was prepared from ethyl 4-acetylquinoline-3-carboxylate (300 mg, 1.23 mmol) with a method analogous to that used for preparing 4-methylquinoline-3-carboxylic acid (KK), to give the title compound (230 mg, 67% yield), used without further purification.

4-(1-Methoxyethyl)quinoline-3-carboxylic acid (WW)

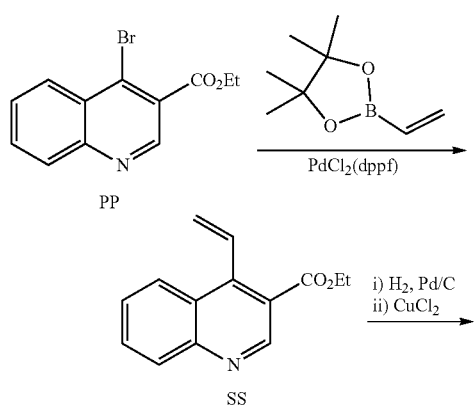

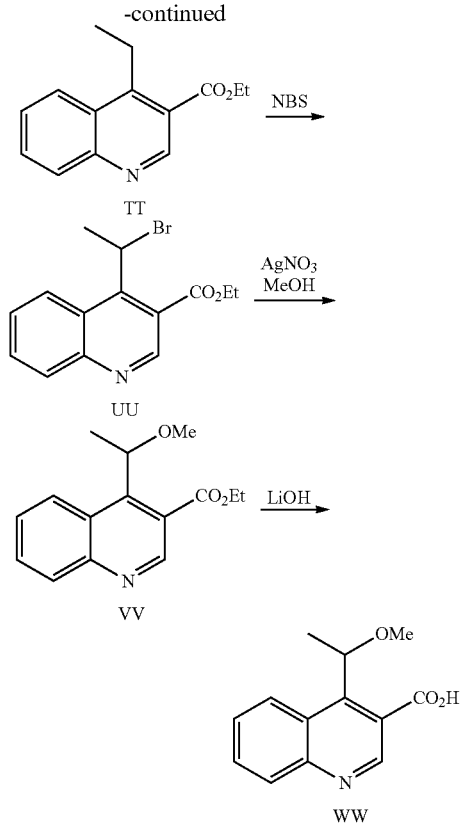

Ethyl 4-vinylquinoline-3-carboxylate (SS)

4,4,5,5-Tetramethyl-2-vinyl-1,3,2-dioxaborolane (2.40 g, 15.5 mmol), Cs$_2$CO$_3$ (6.75 g, 20.7 mmol) and PdCl$_2$(dppf) (378 mg) were added to a solution of ethyl 4-bromoquinoline-3-carboxylate (2.90 g, 10.3 mmol) in dioxane (100 mL) and water (20 mL). The reaction mixture was stirred under nitrogen at 80° C. for 4 hours then cooled, diluted with water (100 mL) and extracted with EtOAc (3×200 mL). The combined organic phases were washed with aq 1N HCl, saturated NaHCO$_3$ and brine, dried over anhydrous sodium sulfate and concentrated. The residue was purified by silica chromatography (hexane:EtOAc=30:1 to 10:1) to give the title compound (1.70 g, 72% yield). $^1$H NMR (400 MHz, CDCl$_3$): δ 9.31 (s, 1H), 8.31 (d, 1H), 8.16 (d, 1H), 7.82 (m, 1H), 7.61 (m, 1H), 7.39 (dd, 1H), 5.89 (d, 1H), 5.52 (d, 1H), 4.44 (q, 2H), 1.44 (m, 3H).

Ethyl 4-ethylquinoline-3-carboxylate (TT)

Pd/C (10%, 150 mg) was added to a solution of ethyl 4-vinylquinoline-3-carboxylate (700 mg, 3.1 mmol) in EtOH (50 mL). The reaction mixture was stirred under hydrogen for 1 hour. LC-MS analysis indicated over-reduction. The reaction mixture was filtered, concentrated and the residue dissolved in dichloroethane (50 mL). Triethylamine (1.3 mL, 9 mmol) and CuCl$_2$ (43 mg, 0.3 mmol) were added and the mixture was stirred at 60° C. under oxygen for 4 hours. The reaction mixture was concentrated, purified by silica chromatography (hexane:EtOAc=30:1 to 10:1) to give the title compound (700 mg, 99% yield). $^1$H NMR (400 MHz, CDCl$_3$): δ 9.26 (s, 1H), 8.22 (m, 2H), 7.82 (m, 1H), 7.65 (m, 1H), 4.47 (q, 2H), 3.49 (q, 2H), 1.45 (m, 6H).

Ethyl 4-(1-bromoethyl)quinoline-3-carboxylate (UU)

NBS (240 mg, 1.37 mmol) and AIBN (11.2 mg, 0.068 mmol) were added to a solution of ethyl 4-ethylquinoline-3-carboxylate (100 mg, 0.46 mmol) in carbon tetrachloride (10 mL) under nitrogen. The reaction mixture was stirred overnight at 80° C. under illumination. The solvent was removed under reduced pressure and the residue purified by preparative-TLC (hexane:ethyl acetate=5:1) to give the title compound (52 mg, 38% yield). $^1$H NMR (400 MHz, CDCl$_3$): δ 9.21 (s, 1H), 8.87 (d, 1H), 8.32 (d, 1H), 7.85 (m, 1H), 7.72 (m, 1H), 6.59 (m, 1H), 4.50 (m, 2H), 2.29 (d, 3H), 1.73 (s, 1H), 1.48 (t, 3H).

Ethyl 4-(1-methoxyethyl)quinoline-3-carboxylate (VV)

AgNO$_3$ (770 mg, 4.5 mmol) was added to a solution of ethyl 4-(1-bromoethyl)quinoline-3-carboxylate (920 mg, 3 mmol) in MeOH (60 mL). The reaction mixture was stirred at RT for 48 hours, then concentrated under reduced pressure and purified by silica chromatography (petroleum ether:EtOAc=10:1 to 3:1) to give the title compound (60 mg, 9% yield). $^1$H NMR (400 MHz, CDCl$_3$): δ 9.08 (s, 1H), 8.59 (d, 1H), 8.16 (d, 1H), 7.78 (m, 1H), 7.62 (m, 1H), 5.36 (m, 1H), 4.48 (q, 2H), 3.23 (s, 3H), 1.76 (d, 3H), 1.46 (t, 3H).

4-(1-Methoxyethyl)quinoline-3-carboxylic acid (WW)

4-(1-Methoxyethyl)quinoline-3-carboxylic acid was prepared from ethyl 4-(1-methoxyethyl)quinoline-3-carboxylate (VV) (60 mg) with a method analogous to that used for preparing 4-methylquinoline-3-carboxylic acid (KK).

4-(1-Azidoethyl)quinoline-3-carboxylic acid (YY)

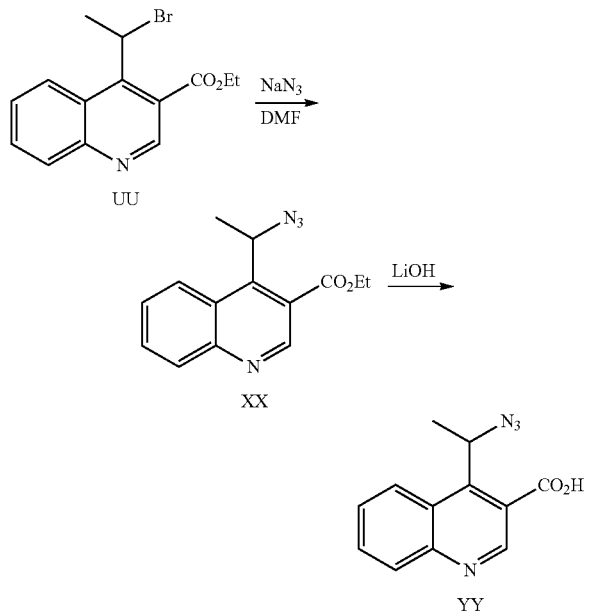

Ethyl 4-(1-azidoethyl)quinoline-3-carboxylate (XX)

Sodium azide (25 mg, 0.39 mmol) was added to a solution of ethyl 4-(1-bromoethyl)quinoline-3-carboxylate (40 mg, 0.13 mmol) in DMF (5 mL). The reaction mixture was heated to 60° C. and stirred overnight. The resulting mixture was diluted with water and extracted (EtOAc). The combined organic layers were washed with sat. NaHCO$_3$ solution, brine, dried over anhydrous sodium sulfate and concentrated under reduced pressure to give the title compound (25 mg), used without further purification. $^1$H NMR (400 MHz, CDCl$_3$): δ 9.19 (s, 1H), 8.57 (d, 1H), 8.29 (d, 1H), 7.86 (m, 1H), 7.69 (m, 1H), 6.05 (m, 1H), 4.53 (m, 2H), 1.82 (d, 3H), 1.48 (t, 3H).

4-(1-Azidoethyl)quinoline-3-carboxylic acid (YY)

4-(1-Azidoethyl)quinoline-3-carboxylic acid was prepared from ethyl 4-(1-azidoethyl)quinoline-3-carboxylate (25 mg) with a method analogous to that used for preparing 4-methylquinoline-3-carboxylic acid (KK), to give 20 mg of the title compound, used without further purification.

6-Fluoro-4-(1-methoxyethyl)quinolin-3-amine (BBB)

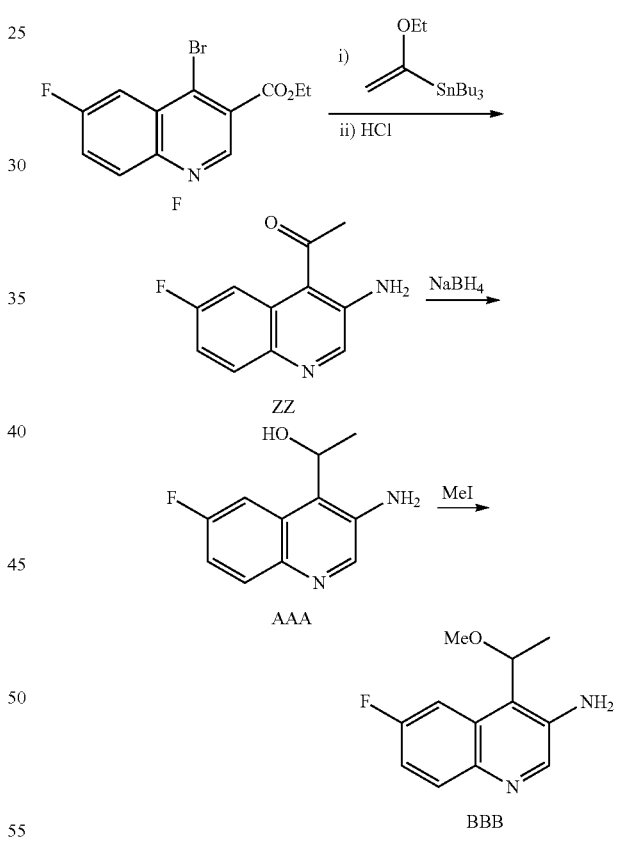

1-(3-Amino-6-fluoroquinolin-4-yl)ethan-1-one (ZZ)

Pd(PPh$_3$)$_4$ (0.3 g) was added to a solution of 4-bromo-6-fluoroquinolin-3-amine (1 g, 4.1 mmol) and tributyl(1-ethoxyvinyl)stannane (2.2 g, 6.1 mmol) in dioxane (20 mL) under a nitrogen atmosphere. The reaction was heated at 90° C. overnight, then cooled, filtered, and washed with ethyl acetate (100 mL). The filtrate was washed with brine, dried (Na$_2$SO$_4$), and concentrated. The residue was purified by silica chromatography (petroleum ether/EtOAc=10:1) to give a yellow solid (810 mg), which was treated with 2 N HCl/dioxane (5.2 mL/10 mL) for 16 hours. The solution was poured into ice-cold sat. NaHCO₃ solution (50 mL) and extracted with EtOAc (3×50 mL). The organic extracts were combined, washed with brine, dried (Na₂SO₄), and concentrated to give the title compound (650 mg, 77% yield), which was used without further purification.

1-(3-Amino-6-fluoroquinolin-4-yl)ethan-1-ol (AAA)

NaBH₄ (182 mg, 4.8 mmol) was added to a solution of 1-(3-amino-6-fluoroquinolin-4-yl)ethan-1-one (650 mg, 3.2 mmol) in anhydrous methanol (10 mL) and the reaction mixture stirred for 1 hour at rt. The reaction was quenched with sat. NH₄Cl solution (30 mL) and extracted with EtOAc (3×30 mL). The organic extracts were combined, washed with brine, dried (Na₂SO₄), and concentrated. The residue was washed with DCM/petroleum ether (10 mL, 2:1) to give the title compound (503 mg, 77% yield) as a grey solid.

6-Fluoro-4-(1-methoxyethyl)quinolin-3-amine (BBB)

1-(3-Amino-6-fluoroquinolin-4-yl)ethan-1-ol (250 mg, 1.2 mmol) was dissolved in THF (10 mL) and cooled to 0° C. Sodium hydride (97 mg, 1.2 mmol, 60% in mineral oil) was added and the reaction was stirred for 1 hour at 0° C. Iodomethane (207 mg, 1.5 mmol) was then added and the reaction was stirred for another 1 hour at rt. The reaction was quenched with sat. NH₄Cl (20 mL) and then extracted with ethyl acetate (3×20 mL). The organic extracts were combined, washed with brine, dried (Na₂SO₄), and concentrated. The residue was purified by silica chromatography (petroleum ether/EtOAc=5:1) to give the title compound (240 mg, 90% yield) as a yellow solid. MS m/z 221.3 [M+H]⁺.

4-(1-Methoxyethyl)-6-methylquinolin-3-amine (CCC)

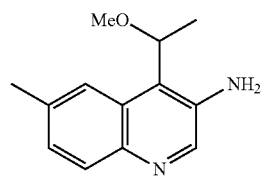

CCC 4-(1-Methoxyethyl)-6-methylquinolin-3-amine (CCC) was prepared from 4-bromo-6-methylquinolin-3-amine (H) with a method analogous to that used for preparing 6-fluoro-4-(1-methoxyethyl)quinolin-3-amine (BBB). ¹H NMR (400 MHz, CDCl₃): δ 8.44 (s, 1H), 7.94 (d, 1H), 7.56 (s, 1H), 7.30 (m, 1H), 5.28 (q, 1H), 4.99 (br, 2H), 3.33 (s, 3H), 2.53 (s, 3H), 1.59 (d, 3H).

4-(1-Ethoxyethyl)-6-fluoroquinolin-3-amine (DDD)

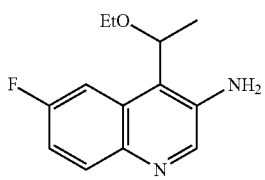

DDD 4-(1-Ethoxyethyl)-6-methylquinolin-3-amine (DDD) was prepared from 1-(3-amino-6-fluoroquinolin-4-yl)ethan-1-ol (AAA) and iodoethane with a method analogous to that used for preparing 6-fluoro-4-(1-methoxyethyl)quinolin-3-amine (BBB).

4-(1-Ethoxyethyl)quinolin-3-amine (EEE)

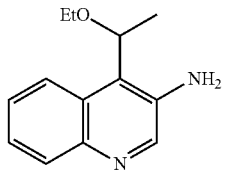

EEE 4-(1-Ethoxyethyl)quinolin-3-amine (EEE) was prepared from 4-bromoquinolin-3-amine (S) with a method analogous to that used for preparing 6-fluoro-4-(1-methoxyethyl)quinolin-3-amine (BBB). MS m/z 218.3[M+H]⁺.

3-Chloro-5-isocyanato-2-(2H-1,2,3-triazol-2-yl)pyridine (III)

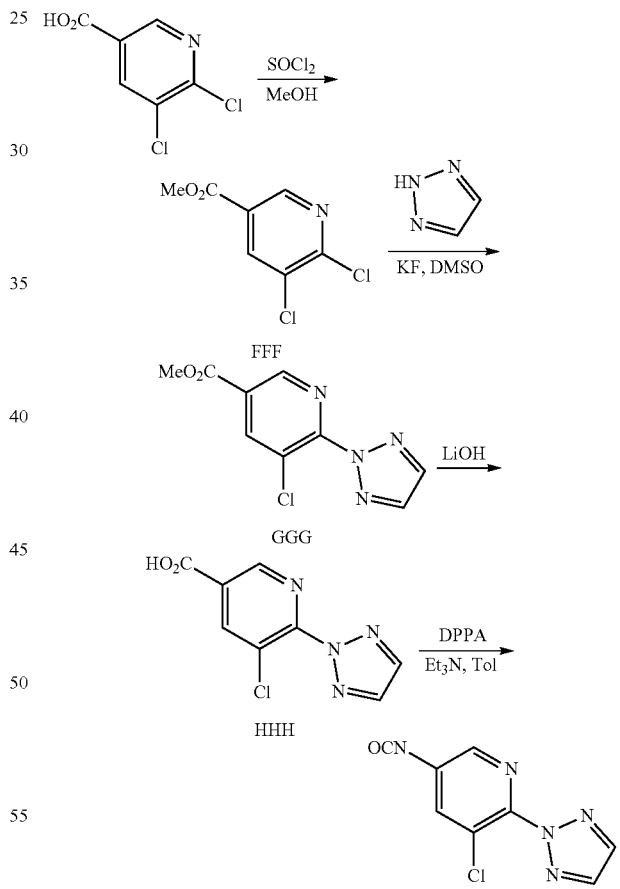

Methyl 5,6-dichloropyridine-3-carboxylate (FFF)

Thionyl chloride (27.9 g, 234 mmol) was added dropwise to the solution of 5,6-dichloropyridine-3-carboxylic acid (18.0 g, 94 mmol) in MeOH (300 mL) at 0° C. The resulting mixture was heated under reflux for 3 hours, cooled and concentrated under reduced pressure. The residue was purified by silica chromatography (hexane:EtOAc=5:1 to 3:1) to give the title compound (6.7 g, 34.7% yield) as a white solid. MS m/z 226.08 [M+H]$^+$.

Methyl 5-chloro-6-(triazol-2-yl)pyridine-3-carboxylate (GGG)

2H-1,2,3-Triazole (2.03 g, 29.4 mmol) and cesium fluoride (4.47 g, 29.4 mmol) were added to a solution of methyl 5,6-dichloropyridine-3-carboxylate (3.03 g, 14.7 mmol) in DMSO (50 mL). The resulting mixture was heated at 100° C. for 2 hours. After cooling, the mixture was diluted with EtOAc (200 mL), washed with saturated NaHCO$_3$ solution, water and brine. The organic phase was dried (Na$_2$SO$_4$) and concentrated, and the residue purified by silica chromatography (DCM:MeOH=100:1 to give the title compound (880 mg, 25% yield). $^1$H NMR (400 MHz, CDCl$_3$): δ 9.10 (s, 1H), 8.58 (d, 1H), 7.99 (s, 2H), 4.02 (s, 3H).

5-Chloro-6-(triazol-2-yl)pyridine-3-carboxylic acid (HHH)

Lithium hydroxide hydrate (633 mg, 15 mmol) in water (5 mL) was added to a solution of methyl 5-chloro-6-(triazol-2-yl)pyridine-3-carboxylate (900 mg, 3.8 mmol) in MeOH (10 mL) at 0° C., and the mixture was stirred for 2 hours and then concentrated. The residue was dissolved in water (10 mL) and washed with hexane:EtOAc (5:1, 2×10 mL). The aqueous phase was acidified (pH 3-4) with 1 N aq. HCl, then concentrated to give the title compound (1.1 g, ~100% yield, contained LiCl), used without further purification. MS m/z 224.01 [M+H]$^+$.

3-Chloro-5-isocyanato-2-(2H-1,2,3-triazol-2-yl)pyridine (III)

Diphenylphosphoryl azide (632 mg, 2.3 mmol) was added to a solution of 5-chloro-6-(triazol-2-yl)pyridine-3-carboxylic acid (430 mg, 1.9 mmol) and triethylamine (580 mg, 5.7 mmol) in toluene (20 mL). The mixture was stirred for 1 hour then heated to 80° C. for 2 hours to give the title compound as a toluene solution, used directly in the next step.

Isocyanates JJJ and KKK were prepared with methods analogous to that used for preparing 3-chloro-5-isocyanato-2-(2H-1,2,3-triazol-2-yl)pyridine (III) from the corresponding azole and methyl 5,6-dichloropyridine-3-carboxylate (FFF) as indicated in the table below.

| Isocyanate | Structure/Name | m/z [M + 1]$^+$ | Starting material |
|---|---|---|---|
| JJJ | 3-Chloro-5-isocyanato-2-(1H-pyrazol-1-yl)pyridine | — | 1H-Pyrazole |
| KKK | 3-Chloro-5-isocyanato-2-(1H-1,2,4-triazol-1-yl)pyridine | — | 1H-1,2,4-Triazole |

4-Isocyanato-2-(trifluoromethyl)pyridine (LLL)

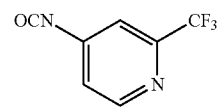

4-Isocyanato-2-(trifluoromethyl)pyridine (LLL) was prepared with a method analogous to that used for preparing 3-chloro-5-isocyanato-2-(2H-1,2,3-triazol-2-yl)pyridine (III) from 2-(trifluoromethyl)isonicotinic acid, and used directly in the subsequent step.

5-Chloro-6-(triazol-2-yl)pyridin-3-amine (NNN)

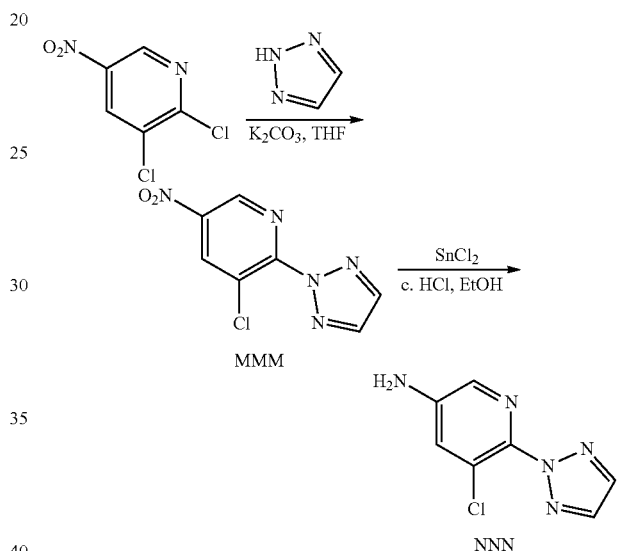

3-Chloro-5-nitro-2-(triazol-2-yl)pyridine (MMM)

2H-1,2,3-Triazole (760 mg, 11 mmol) was added to a suspension of 2,3-dichloro-5-nitro-pyridine (965 mg, 5 mmol) and anhydrous potassium carbonate (1.03 g, 7.5 mmol) in THF (50 mL), and the mixture was stirred overnight at room temperature. The mixture was diluted with EtOAc (100 mL), washed with water and brine, and the organic phase was dried over anhydrous sodium sulfate, filtered and concentrated. The residue was purified by silica chromatography (hexane:EtOAc=5:1 to 1:1) to give the title compound (505 mg, 44%). $^1$H NMR (400 MHz, DMSO-d$_6$): δ 9.39 (d, 1H), 9.15 (d, 1H), 8.34 (s, 2H).

5-Chloro-6-(triazol-2-yl)pyridin-3-amine (NNN)

Tin (II) chloride dihydrate (4.75 g, 21 mmol) was added in portions to a suspension of 3-chloro-5-nitro-2-(triazol-2-yl)pyridine (950 mg, 4.2 mmol) in conc. HCl (25 mL) and EtOH (100 mL) at room temperature, then the mixture was stirred overnight. The solvent was removed under reduced pressure, and the residue was diluted with water (100 mL), basicified with 3 N aq. NaOH solution to pH 9, then extracted with EtOAc (2×100 mL). The combined organic layers were washed with brine, dried over anhydrous sodium sulfate, filtered and concentrated to give the title compound (795 mg, 97%) as a yellow solid. $^1$H NMR (400 MHz, DMSO-d$_6$): δ 8.05 (s, 2H), 7.82 (d, 1H), 7.20 (d, 1H), 6.21 (bs, 2H). MS m/z 195.95 [M+H]$^+$.

tert-Butyl (7-cyclopropyl-2-methylthiazolo[5,4-b]pyridin-6-yl)carbamate (TTT)

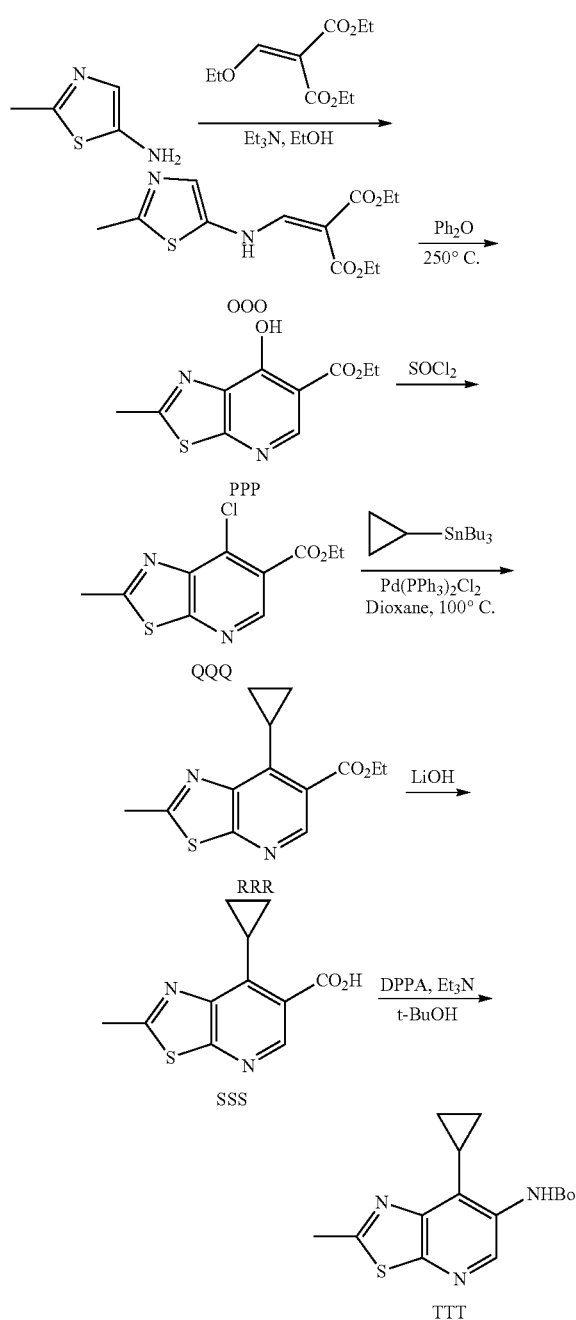

Diethyl 2-(((2-methylthiazol-5-yl)amino)methylene)malonate (OOO)

2-Methylthiazol-5-amine (4.5 g, 39.41 mmol) was dissolved in EtOH (150 mL). Diethyl 2-(ethoxymethylene)malonate (7.97 mL, 39.41 mmol) was added and the mixture stirred at 90° C. for 3 hours. The mixture was cooled to 0° C. and stirred for 1 hour, and the resulting solid was filtered, washed with EtOH and dried to give the title compound (3.62 g, 32% yield). $^1$H NMR (500 MHz, DMSO-d$_6$): δ 10.74 (d, 1H), 7.94 (d, 1H), 7.53 (s, 1H), 4.19 (q, 2H), 4.11 (q, 2H), 2.58 (s, 3H), 1.24 (m, 6H); MS m/z: 285.06 [M+H]$^+$.

Ethyl 7-hydroxy-2-methylthiazolo[5,4-b]pyridine-6-carboxylate (PPP)

Diethyl 2-(((2-methylthiazol-5-yl)amino)methylene)malonate (3.62 g, 12.73 mmol) was suspended in diphenyl ether (75 mL) and heated to 250° C. for 45 minutes. The mixture was cooled to room temperature, diluted with hexanes (250 mL) then stirred at 0° C. for 1 hour. The resulting solid was filtered, washed with hexanes and dried to give the title compound (3 g, 98% yield). $^1$H NMR (500 MHz, DMSO-d$_6$): δ 11.97 (s, 1H), 8.76 (s, 1H), 4.38 (q, 2H), 2.82 (s, 3H), 1.35 (t, 3H); MS m/z: 238.69 [M+H]$^+$.

Ethyl 7-chloro-2-methylthiazolo[5,4-b]pyridine-6-carboxylate (QQQ)

SOCl$_2$ (3 mL, 42 mmol) and DMF (5 drops) were added to a solution of ethyl 7-hydroxy-2-methylthiazolo[5,4-b]pyridine-6-carboxylate (1 g, 4.20 mmol) in CHCl$_3$ (100 mL). The mixture was stirred at reflux for 3 hours, and then concentrated. The residue was suspended in toluene (50 mL) and the solvent removed to give the title compound (685 mg, 64% yield), used without further purification. MS m/z: 258.93 [M+H]$^+$.

Ethyl 7-cyclopropyl-2-methylthiazolo[5,4-b]pyridine-6-carboxylate (RRR)

Ethyl 7-chloro-2-methylthiazolo[5,4-b]pyridine-6-carboxylate (500 mg, 1.95 mmol) and tributyl(cyclopropyl)stannane (708 mg, 2.14 mmol) were dissolved in 1,4-dioxane (5 mL) and thoroughly degassed. Pd(PPh$_3$)Cl$_2$ (137 mg, 0.195 mmol) was added and the reaction mixture was stirred under nitrogen at 100° C. for 24 hours. The reaction was diluted with water and extracted with EtOAc (3×50 mL). The combined organic extracts were washed with brine, dried over MgSO$_4$ and concentrated. The residue was purified by silica chromatography (10 to 60% EtOAc in hexanes) to give the title compound (200 mg, 39% yield). MS m/z: 262.64 [M+H]$^+$.

7-Cyclopropyl-2-methylthiazolo[5,4-b]pyridine-6-carboxylic acid (SSS)

Ethyl 7-cyclopropyl-2-methylthiazolo[5,4-b]pyridine-6-carboxylate (200 mg, 0.76 mmol) was dissolved in THF (5 mL) and MeOH (3 mL). LiGH (65 mg, 1.53 mmol) was added and the mixture stirred at 60° C. for 2 hours. The mixture was diluted with water and extracted with EtOAc (2×50 mL). The aqueous layer was acidified using 3M HCl and extracted with EtOAc (3×50 mL). The combined organic layer was washed with brine, dried over MgSO$_4$ and concentrated to give the title compound (100 mg, 59% yield), used without further purification. $^1$H NMR (500 MHz, DMSO-d$_6$): δ 13.53 (s, 1H), 8.73 (s, 1H), 2.89 (m, 1H), 2.81 (s, 3H), 1.74 (m, 2H), 1.16 (m, 2H); MS m/z: 234.76 [M+H]$^+$.

tert-Butyl (7-cyclopropyl-2-methylthiazolo[5,4-b]pyridin-6-yl)carbamate (TTT)

DPPA (97 µL, 0.45 mmol) and Et$_3$N (68 µL, 0.49 mmol) were added to a solution of 7-cyclopropyl-2-methylthiazolo[5,4-b]pyridine-6-carboxylic acid (95 mg, 0.41 mmol) in t-butanol (10 mL). The mixture was stirred at room temperature for 30 minutes and then at 100° C. for 1 hour. The mixture was cooled to room temperature, quenched with sat. aq. NaHCO$_3$ solution and extracted with EtOAc (3×50 mL). The combined organic layer was washed with brine, dried over MgSO$_4$ and concentrated. The residue was purified by silica chromatography (10 to 80% EtOAc in hexanes) to give the title compound (35 mg, 28% yield). MS m/z: 306.21 [M+H]$^+$.

7-(1-Ethoxyethyl)-2-methylthiazolo[5,4-b]pyridine-6-carboxylic acid (WWW)

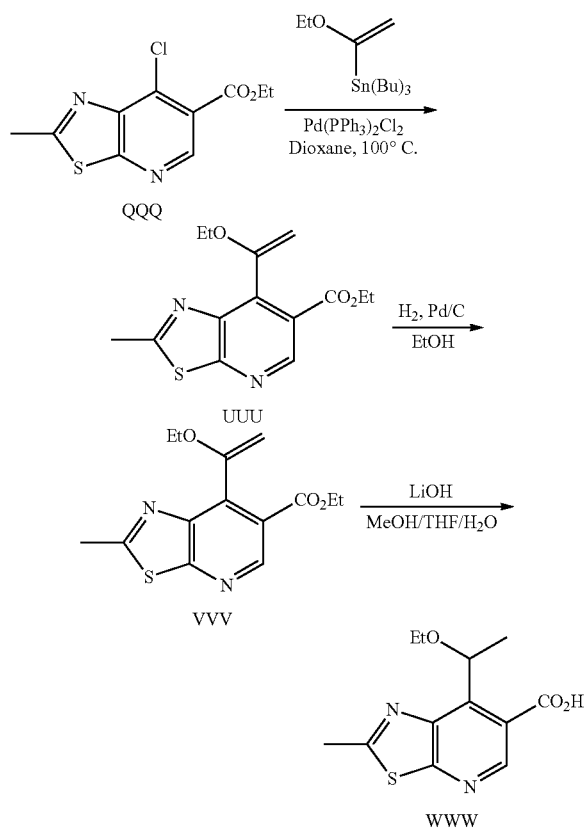

QQQ

UUU

VVV

WWW

Ethyl 7-(1-ethoxyvinyl)-2-methylthiazolo[5,4-b]pyridine-6-carboxylate (UUU)

Ethyl 7-chloro-2-methylthiazolo[5,4-b]pyridine-6-carboxylate (500 mg, 1.95 mmol) and tributyl(1-ethoxyvinyl)stannane (708 µL, 2.10 mmol) were dissolved in 1,4-dioxane (5 mL) and thoroughly degassed. Pd(PPh$_3$)Cl$_2$ (134 mg, 0.191 mmol) was added and the flask was flushed with N$_2$, then stirred at 100° C. for 24 hours. The reaction was diluted with water and extracted with EtOAc (3×50 mL). The combined organic extracts were washed with brine, dried over MgSO$_4$ and condensed to give a brown oil that was filtered through a plug of silica gel eluting with 30% EtOAc in hexanes to give the title compound (347 mg, 62% yield) as a yellow oil that was used without further purification. MS m/z: 293.05 [M+H]$^+$.

Ethyl 7-(1-ethoxyethyl)-2-methylthiazolo[5,4-b]pyridine-6-carboxylate (VVV)

Pd, 10% on carbon (55 mg, 0.05 mmol) was added to a solution of ethyl 7-(1-ethoxyvinyl)-2-methylthiazolo[5,4-b]pyridine-6-carboxylate (150 mg, 0.51 mmol) in EtOH (10 mL). The reaction was stirred under H$_2$ for 6 hours, further Pd, 10% on carbon (165 mg, 0.15 mmol) was added and the mixture stirred under H$_2$ for 14 hours. The mixture was filtered over Celite, washing with EtOH (100 mL) and the filtrate concentrated to give the title compound (150 mg, 99% yield) as a brown oil that was used without further purification. MS m/z: 295.24 [M+H]$^+$.

7-(1-Ethoxyethyl)-2-methylthiazolo[5,4-b]pyridine-6-carboxylic acid (WWW)

7-(1-Ethoxyethyl)-2-methylthiazolo[5,4-b]pyridine-6-carboxylic acid was prepared from ethyl 7-(1-ethoxyethyl)-2-methylthiazolo[5,4-b]pyridine-6-carboxylate using the procedure described for SSS, to give the title compound (100 mg, 74% yield) as a yellow solid. $^1$H NMR (500 MHz, DMSO-d$_6$): δ 8.60 (s, 1H), 5.39 (q, 1H), 4.36 (q, 2H), 2.87 (s, 3H), 1.61 (d, 3H), 1.07 (t, 3H); MS m/z: 267.01 [M+H]$^+$.

Thiazolopyridine acids XXX and YYY were prepared from ethyl 7-chlorothiazolo[5,4-b]pyridine-6-carboxylate (ZZZ) with methods analogous to that used for preparing thiazolopyridine SSS or WWW. Ethyl 7-chlorothiazolo[5,4-b]pyridine-6-carboxylate (ZZZ) was prepared from thiazol-5-amine in a manner analogous to that used for preparing QQQ.

| Thiazolo-pyridine acid | Structure/Name | m/z [M + 1]$^+$ | $^1$H NMR (500 MHz, DMSO-d$_6$) |
|---|---|---|---|
| XXX | 7-Cyclopropylthiazolo[5,4-b]pyridine-6-carboxylic acid | 220.76 | 13.40 (br, 1H), 9.53 (s, 1H), 8.86 (s, 1H), 2.98 (m, 1H), 1.79 (m, 2H), 1.21 (m, 2H) |
| YYY | 7-(1-Ethoxyethyl)thiazolo[5,4-b]pyridine-6-carboxylic acid | 253.21 | 9.63 (s, 1H), 8.73 (s, 1H), 5.48 (q, 1H), 3.23 (q, 2H), 1.63 (d, 3H), 1.07 (t, 3H) |

7-(Dimethylamino)thiazolo[5,4-b]pyridine-6-carboxylic acid (AAAA)

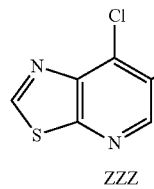

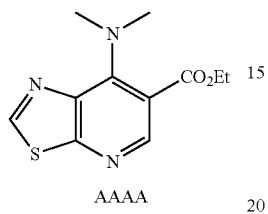

Ethyl 7-(dimethylamino)thiazolo[5,4-b]pyridine-6-carboxylate

A solution of ethyl 7-chlorothiazolo[5,4-b]pyridine-6-carboxylate (ZZZ, 200 mg, 0.82 mmol), dimethylamine 2M in THF (0.51 mL, 0.99 mmol) and DIEA (440 µL, 1.65 mmol) in DMF (5 mL) was stirred at 60° C. for 3 hours. The reaction was quenched with $H_2O$ and extracted with EtOAc. The combined organic layer was washed with brine, dried over $MgSO_4$ and concentrated to give a brown oil that was used without further purification. MS m/z: 251.93 $[M+H]^+$.

7-(Dimethylamino)thiazolo[5,4-b]pyridine-6-carboxylic acid (AAAA)

7-(Dimethylamino)thiazolo[5,4-b]pyridine-6-carboxylic acid was prepared from ethyl 7-(dimethylamino)thiazolo[5,4-b]pyridine-6-carboxylate using the procedure described for SSS except the aqueous layer was acidified, concentrated and purified by reverse phase HPLC using a gradient of 0-60% ACN in $H_2O$ to give the title compound (138 mg, 75% yield) as a yellow solid. $^1$H NMR (500 MHz, DMSO-$d_6$): δ 9.27 (s, 1H), 8.47 (s, 1H), 3.27 (s, 6H); MS m/z: 224.64 [M+H]+.

Thiazolopyridine acids BBBB-DDDD were prepared from ethyl 7-chlorothiazolo[5,4-b]pyridine-6-carboxylate (ZZZ) using analogous methods to those described for 7-(dimethylamino)thiazolo[5,4-b]pyridine-6-carboxylic acid (AAAA).

| Thiazolo-pyridine acid | Structure/Name | m/z [M + 1]$^+$ | $^1$H NMR (500 MHz, DMSO-$d_6$) |
|---|---|---|---|
| BBBB | ![structure] 7-((2-Methoxyethyl)(methyl)amino)thiazolo[5,4-b]pyridine-6-carboxylic acid | 268.04 | 9.28 (s, 1H), 8.45 (s, 1H), 4.16 (t, 2H), 3.62 (t, 2H), 3.21 (s, 3H), 3.10 (s, 3H) |
| CCCC | ![structure] 7-((1-Methoxypropan-2-yl)(methyl)amino)thiazolo[5,4-b]pyridine-6-carboxylic acid | 282.26 | 9.31 (s, 1H), 8.45 (s, 1H), 5.19 (m, 1H), 3.62 (m, 1H), 3.47 (m, 1H), 3.22 (s, 3H), 2.87 (s, 3H), 1.30 (d, 3H) |
| DDDD | ![structure] 7-(Azetidin-1-yl)thiazolo[5,4-b]pyridine-6-carboxylic acid | 235.98 | — |

Preparation of Example Compounds

1-(6-Chloro-4-(2-methoxypropan-2-yl)quinolin-3-yl)-3-(5-chloro-6-(2H-1,2,3-triazol-2-yl)pyridin-3-yl)urea (1)

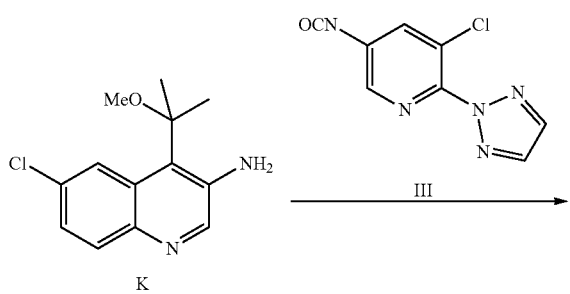

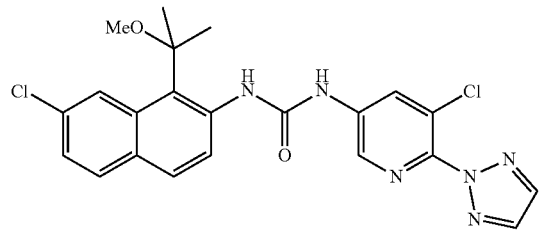

1-(6-Chloro-4-(2-methoxypropan-2-yl)quinolin-3-yl)-3-(5-chloro-6-(2H-1,2,3-triazol-2-yl)pyridin-3-yl)urea (1)

6-Chloro-4-(2-methoxypropan-2-yl)quinolin-3-amine (K) (100 mg, 0.4 mmol) was added to a freshly prepared toluene solution of 3-chloro-5-isocyanato-2-(2H-1,2,3-triazol-2-yl)pyridine (III) (1.6 mmol, 4 eq), stirred at room temperature for 30 mins, and then at 100° C. for 10 hours. After cooling, the mixture was diluted with water (50 mL) and extracted with EtOAc (3×30 mL). The combined organic phases were washed with saturated $NaHCO_3$ solution (3×50 mL) and brine, and then concentrated. The residue was purified by prep-HPLC to give the title compound (20 mg, 11% yield). $^1$H NMR (400 MHz, MeOD-d4): δ 8.94 (m, 2H), 8.55 (m, 2H), 8.03 (m, 3H), 7.70 (m, 1H), 3.12 (s, 3H), 1.95 (s, 6H). MS m/z 472.4 [M+H]$^+$.

Compounds 2-23 were prepared in an analogous manner, employing the indicated starting materials below.

| Example | Structure/Name | $^1$H NMR (400 MHz, DMSO-d$_6$) | m/z [M + 1]$^+$ | Starting materials |
|---|---|---|---|---|
| 2 | 1-(6-Chloro-4-(2-methoxypropan-2-yl)quinolin-3-yl)-3-(2-(trifluoromethyl)pyridin-4-yl)urea | 9.99 (s, 1H), 8.97 (d, 1H), 8.80 (s, 1H), 8.75 (s, 1H), 8.54 (d, 1H), 8.07 (m, 2H), 7.77 (m, 1H), 7.66 (m, 1H), 2.93 (s, 3H), 1.81 (s, 6H) | 439.98 | (K) + (LLL) |
| 3 | 1-(4-(2-Methoxypropan-2-yl)quinolin-3-yl)-3-(2-(trifluoromethyl)pyridin-4-yl)urea | 10.00 (s, 1H), 8.89 (d, 1H), 8.78 (s, 2H), 8.54 (d, 1H), 8.04 (d, 1H), 8.02 (d, 1H), 7.73 (m, 1H), 7.67 (m, 1H), 7.60 (m, 1H), 2.93 (s, 3H), 1.81 (s, 6H) | 404.99 | (L) + (LLL) |
| 4 | 1-(5-Chloro-6-(2H-1,2,3-triazol-2-yl)pyridin-3-yl)-3-(4-cyclopropylquinolin-3-yl)urea | 10.04 (s, 1H), 9.13 (s, 1H), 8.83 (s, 1H), 8.58 (d, 1H), 8.53 (d, 1H), 8.45 (m, 1H), 8.16 (s, 2H), 8.01 (d, 1H), 7.66 (m, 2H), 2.06 (m, 1H), 1.30 (m, 2H), 0.64 (m, 2H) | 406.12 | (X) + (III) |
| 5 | 1-(5-Chloro-6-(2H-1,2,3-triazol-2-yl)pyridin-3-yl)-3-(4-isopropylquinolin-3-yl)urea | MeOD-d4 8.70 (s, 1H), 8.45 (m, 2H), 8.30 (d, 1H), 7.95 (m, 1H), 7.92 (s, 2H), 7.66 (m, 1H), 7.56 (m, 1H), 3.90 (m, 1H), 1.50 (d, 6H) | 408.45 | (U) + (III) |

-continued

| Example | Structure/Name | ¹H NMR (400 MHz, DMSO-d₆) | m/z [M + 1]⁺ | Starting materials |
|---|---|---|---|---|
| 6 | 1-(5-Chloro-6-(2H-1,2,3-triazol-2-yl)pyridin-3-yl)-3-(4-cyclopentylquinolin-3-yl)urea | MeOD-d4 8.83 (s, 1H), 8.52 (m, 2H), 8.29 (d, 1H), 8.06 (d, 1H), 8.04 (s, 2H), 7.77 (m, 1H), 7.65 (m, 1H), 4.03 (m, 1H), 2.19 (m, 6H), 1.95 (m, 2H) | 434.06 | (W) + (III) |
| 7 | 1-(7-Chloro-4-cyclopropylquinolin-3-yl)-3-(5-chloro-6-(2H-1,2,3-triazol-2-yl)pyridin-3-yl)urea | 10.10 (s, 1H), 9.20 (s, 1H), 8.91 (s, 1H), 8.58 (d, 1H), 8.53 (d, 1H), 8.46 (d, 1H), 8.17 (s, 2H), 8.05 (d, 1H), 7.70 (dd, 1H), 2.08 (m, 1H), 1.30 (m, 2H), 0.65 (m, 2H) | 440.0 | (AA) + (III) |
| 8 | 1-(6-Chloro-4-cyclopropylquinolin-3-yl)-3-(5-chloro-6-(2H-1,2,3-triazol-2-yl)pyridin-3-yl)urea | 10.10 (s, 1H), 9.21 (s, 1H), 8.94 (s, 1H), 8.58 (d, 1H), 8.53 (d, 1H), 8.42 (d, 1H), 8.17 (s, 2H), 8.03 (d, 1H), 7.69 (m, 1H), 2.08 (m, 1H), 1.30 (m, 2H), 0.65 (m, 2H) | 440.0 | (Z) + (III) |
| 9 | 1-(5-Chloro-6-(2H-1,2,3-triazol-2-yl)pyridin-3-yl)-3-(4-cyclopropyl-6-fluoroquinolin-3-yl)urea | 10.12 (s, 1H), 9.19 (s, 1H), 8.95 (s, 1H), 8.59 (d, 1H), 8.53 (d, 1H), 8.17 (s, 2H), 8.08 (m, 2H), 7.61 (m, 1H), 2.06 (m, 1H), 1.30 (m, 2H), 0.64 (m, 2H) | 424.0 | (Y) + (III) |

-continued

| Example | Structure/Name | $^1$H NMR (400 MHz, DMSO-$d_6$) | m/z [M + 1]$^+$ | Starting materials |
|---|---|---|---|---|
| 10 | 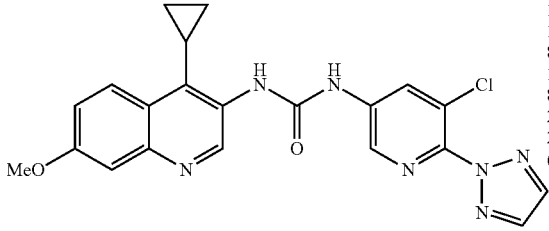 [SMILES: COc1ccc2c(C3CC3)c(NC(=O)Nc3cnc(-n4nccn4)c(Cl)c3)cnc2c1]<br>1-(5-Chloro-6-(2H-1,2,3-triazol-2-yl)pyridin-3-yl)-3-(4-cyclopropyl-7-methoxyquinolin-3-yl)urea | 10.13 (s, 1H), 9.19 (s, 1H), 8.92 (s, 1H), 8.60 (d, 1H), 8.52 (d, 1H), 8.44 (d, 1H), 8.17 (s, 2H), 7.42 (m, 2H), 3.95 (s, 3H), 2.14 (m, 1H), 1.32 (m, 2H), 0.65 (m, 2H) | 435.96 | (CC) + (III) |
| 11 | 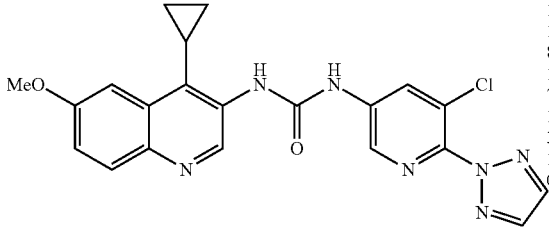 [SMILES: COc1ccc2ncc(NC(=O)Nc3cnc(-n4nccn4)c(Cl)c3)c(C3CC3)c2c1]<br>1-(5-Chloro-6-(2H-1,2,3-triazol-2-yl)pyridin-3-yl)-3-(4-cyclopropyl-6-methoxyquinolin-3-yl)urea | 10.11 (s, 1H), 9.11 (s, 1H), 8.92 (bs, 1H), 8.59 (d, 1H), 8.53 (d, 1H), 8.17 (s, 2H), 7.95 (d, 1H), 7.74 (s, 1H), 7.41 (m, 1H), 3.26 (s, 3H), 2.08 (m, 1H), 1.35 (m, 2H), 0.65 (m, 2H) | 436.0 | (BB) + (III) |
| 12 | 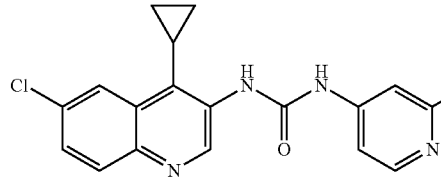<br>1-(6-Chloro-4-cyclopropylquinolin-3-yl)-3-(2-(trifluoromethyl)pyridin-4-yl)urea | 10.19 (s, 1H), 9.17 (s, 1H), 8.92 (s, 1H), 8.57 (d, 1H), 8.41 (d, 1H), 8.10 (d, 1H), 8.03 (d, 1H), 7.72 (m 1H), 7.64 (m, 1H). 2.05 (m, 1H), 1.28 (m, 2H), 0.63 (m, 2H) | 407.0 | (Z) + (LLL) |
| 13 | 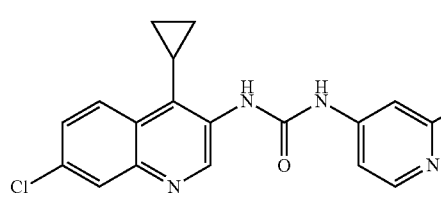<br>1-(7-Chloro-4-cyclopropylquinolin-3-yl)-3-(2-(trifluoromethyl)pyridin-4-yl)urea | 10.20 (s, 1H), 9.17 (s, 1H), 8.90 (s, 1H), 8.57 (d, 1H), 8.45 (d, 1H), 8.10 (d, 1H), 8.05 (d, 1H), 7.71 (m 1H), 7.64 (m, 1H). 2.07 (m, 1H), 1.28 (m, 2H), 0.62 (m, 2H) | 407.0 | (AA) + (LLL) |
| 14 | 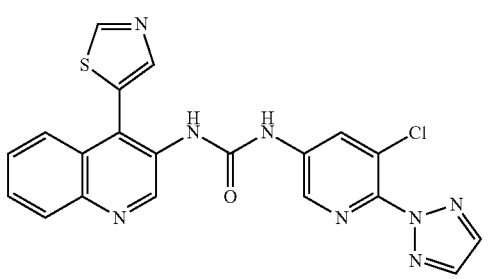 [SMILES: O=C(Nc1cnc(-n2nccn2)c(Cl)c1)Nc1cnc2ccccc2c1-c1cncs1]<br>1-(5-Chloro-6-(2H-1,2,3-triazol-2-yl)pyridin-3-yl)-3-(4-(thiazol-5-yl)quinolin-3-yl)urea | 9.85 (s, 1H), 9.51 (s, 1H), 9.48 (s,1H), 8.47 (s, 2H), 8.43 (s, 1H), 8.15 (m, 3H), 8.11 (d, 1H), 7.75 (m, 1H), 7.60 (m, 1H), 7.54 (m, 1H) | 448.7 | (DD) + (III) |

-continued

| Example | Structure/Name | ¹H NMR (400 MHz, DMSO-d₆) | m/z [M + 1]⁺ | Starting materials |
|---|---|---|---|---|
| 15 | 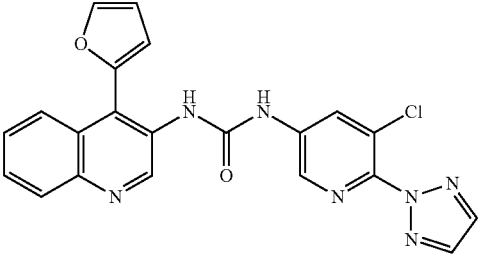 [SMILES: O=C(Nc1cnc(-n2nccn2)c(Cl)c1)Nc1cnc2ccccc2c1-c1ccco1]<br>1-(5-Chloro-6-(2H-1,2,3-triazol-2-yl)pyridin-3-yl)-3-(4-(furan-2-yl)quinolin-3-yl)urea | 9.99 (s, 1H), 9.40 (s, 1H), 8.65 (s, 1H), 8.50 (d, 2H), 8.16 (s, 2H), 8.10 (m, 2H), 7.87 (m, 1H), 7.76 (m, 1H), 7.65 (m, 1H), 7.05 (s, 1H), 6.86 (s, 1H) | 432.3 | (EE) + (III) |
| 16 | 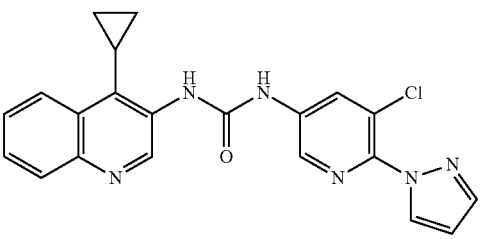 [SMILES: O=C(Nc1cnc(-n2cccn2)c(Cl)c1)Nc1cnc2ccccc2c1C1CC1]<br>1-(5-Chloro-6-(1H-pyrazol-1-yl)pyridin-3-yl)-3-(4-cyclopropylquinolin-3-yl)urea | 9.99 (s, 1H), 9.26 (s, 1H), 8.90 (s, 1H), 8.54 (s, 1H), 8.48 (m, 1H), 8.45 (s, 1H), 8.19 (s, 1H), 8.04 (m, 1H), 7.78 (s, 1H), 7.72 (m, 2H), 6.54 (s, 1H), 2.10 (m, 1H), 1.32 (m, 2H), 0.66 (m, 2H) | 405.3 | (X) + (JJJ) |
| 17 | 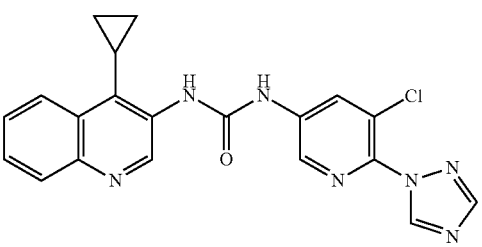 [SMILES: O=C(Nc1cnc(-n2cncn2)c(Cl)c1)Nc1cnc2ccccc2c1C1CC1]<br>1-(5-Chloro-6-(1H-1,2,4-triazol-1-yl)pyridin-3-yl)-3-(4-cyclopropylquinolin-3-yl)urea | 9.99 (s, 1H), 9.12 (s, 1H), 9.04 (s, 1H), 8.83 (s, 1H), 8.58 (d, 1H), 8.51 (d, 1H), 8.44 (m, 1H), 8.29 (s, 1H), 7.99 (m, 1H), 7.66 (m, 2H), 2.06 (m, 1H), 1.30 (m, 2H), 0.64 (m, 2H) | 406.3 | (X) + (KKK) |
| 18 | 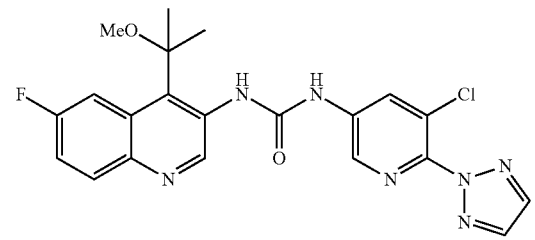 [SMILES: COC(C)(C)c1c(NC(=O)Nc2cnc(-n3nccn3)c(Cl)c2)cnc2ccc(F)cc12]<br>1-(5-Chloro-6-(1H-1,2,3-triazol-2-yl)pyridin-3-yl)-3-(6-fluoro-4-(2-methoxypropan-2-yl)quinolin-3-yl)urea | 9.88 (br, 1H), 8.77 (s, 2H), 8.64 (m, 1H), 8.59 (d, 1H), 8.50 (d, 1H), 8.16 (s, 2H), 8.11 (m, 1H), 7.67 (m, 1H), 2.95 (s, 3H), 1.83 (s, 6H) | 456.2 | (M) + (III) |

| Example | Structure/Name | ¹H NMR (400 MHz, DMSO-d₆) | m/z [M + 1]⁺ | Starting materials |
|---|---|---|---|---|
| 19 | 1-(5-Chloro-6-(1H-1,2,3-triazol-2-yl)pyridin-3-yl)-3-(4-(2-methoxypropan-2-yl)-6-methylquinolin-3-yl)urea | 9.89 (br, 1H), 8.78 (s, 1H), 8.73 (s, 1H), 8.67 (s, 1H), 8.58 (s, 1H), 8.50 (s, 1H), 8.16 (s, 2H), 7.92 (d, 1H), 7.55 (d, 1H), 2.95 (s, 3H), 2.52 (s, 3H), 1.40 (s, 6H) | 452.3 | (N) + (III) |
| 20 | 1-(5-Chloro-6-(1H-1,2,3-triazol-2-yl)pyridin-3-yl)-3-(6-fluoro-4-(1-methoxyethyl)quinolin-3-yl)urea | 10.36 (br, 1H), 9.25 (s, 1H), 9.05 (br, 1H), 8.57 (s, 1H), 8.52 (s, 1H), 8.16 (s, 2H) 8.11 (m, 2H), 7.63 (m, 1H), 5.36 (m, 1H), 3.26 (s, 3H), 1.56 (d, 3H) | 442.2 | (BBB) + (III) |
| 21 | 1-(5-Chloro-6-(1H-1,2,3-triazol-2-yl)pyridin-3-yl)-3-(4-(1-methoxyethyl)-6-methylquinolin-3-yl)urea | 10.36 (br, 1H), 9.16 (s, 1H), 8.98 (s, 1H), 8.56 (d, 1H), 8.52 (d, 1H), 8.16 (s, 2H), 8.14 (m, 1H), 7.92 (d, 1H), 7.55 (d, 1H), 5.43 (m, 1H), 3.26 (s, 3H), 2.53 (s, 3H), 1.57 (d, 3H) | 438.2 | (CCC) + (III) |
| 22 | 1-(5-Chloro-6-(1H-1,2,3-triazol-2-yl)pyridin-3-yl)-3-(4-(1-ethoxyethyl)-6-fluoroquinolin-3-yl)urea | 10.31 (br, 1H), 9.22 (s, 1H), 9.02 (s, 1H), 8.59 (d, 1H), 8.51 (d, 1H), 8.21 (m, 1H), 8.17 (s, 2H), 8.09 (m, 1H), 7.64 (m, 1H), 5.44 (m, 1H), 3.45 (m, 1H), 3.29 (m, 1H), 1.58 (d, 3H), 1.15 (t, 3H) | 456.2 | (DDD) + (III) |

| Example | Structure/Name | $^1$H NMR (400 MHz, DMSO-$d_6$) | m/z [M + 1]$^+$ | Starting materials |
|---|---|---|---|---|
| 23 | 1-(5-Chloro-6-(1H-1,2,3-triazol-2-yl)pyridin-3-yl)-3-(4-(1-ethoxyethyl)quinolin-3-yl)urea | 10.28 (br, 1H), 9.19 (s, 1H), 8.97 (s, 1H), 8.59 (d, 1H), 8.51 (d, 1H), 8.46 (m, 1H), 8.16 (s, 2H), 8.03 (d, 1H), 7.71 (m, 1H), 7.62 (m, 1H), 5.50 (m, 1H), 3.46 (m, 1H), 3.33 (m, 1H), 1.60 (d, 3H), 1.15 (t, 3H) | 438.2 | (EEE) + (III) |

1-(5-Chloro-6-(2H-1,2,3-triazol-2-yl)pyridin-3-yl)-3-(6-fluoro-4-(1-hydroxyethyl)quinolin-3-yl)urea (24)

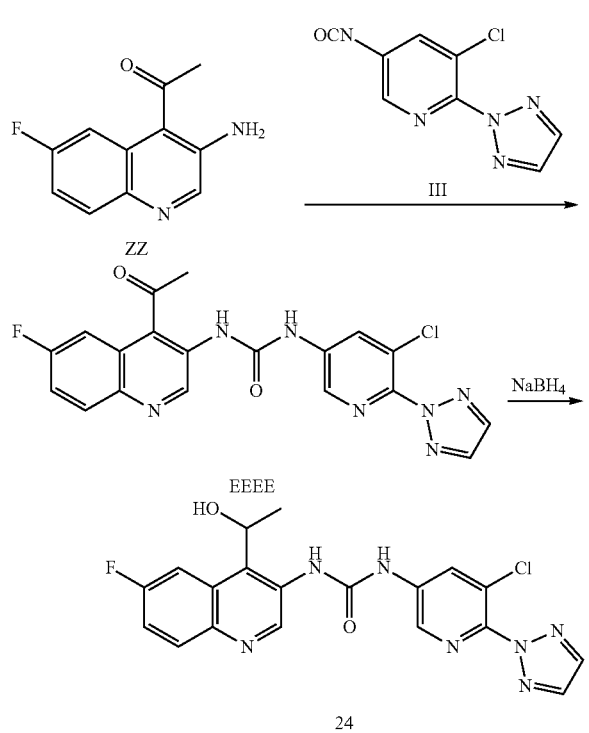

1-(4-Acetyl-6-fluoroquinolin-3-yl)-3-(5-chloro-6-(2H-1,2,3-triazol-2-yl)pyridin-3-yl)urea (EEEE)

1-(4-Acetyl-6-fluoroquinolin-3-yl)-3-(5-chloro-6-(2H-1,2,3-triazol-2-yl)pyridin-3-yl)urea (EEEE) was prepared from 1-(3-amino-6-fluoroquinolin-4-yl)ethan-1-one (ZZ) using an analogous method to that used for preparing Example 1. MS m/z 426.3 [M+H]$^+$.

1-(5-Chloro-6-(2H-1,2,3-triazol-2-yl)pyridin-3-yl)-3-(6-fluoro-4-(1-hydroxyethyl)quinolin-3-yl)urea (24)

NaBH$_4$ (5 mg, 0.1 mmol) was added to a solution of 1-(4-acetyl-6-fluoroquinolin-3-yl)-3-(5-chloro-6-(2H-1,2,3-triazol-2-yl)pyridin-3-yl)urea (EEEE; 35 mg, 0.1 mmol) in methanol (2 mL). The reaction mixture was stirred for 30 min at rt. The reaction was quenched with water (5 mL) and then extracted with EtOAc (3×5 mL). The organic extracts were combined, washed with brine, dried (Na$_2$SO$_4$), and concentrated. The residue was purified by prep-TLC (DCM/MeOH=20:1) to give the title compound (17 mg, 48% yield) as a light yellow solid. $^1$H NMR (400 MHz, DMSO-$d_6$): δ 10.54 (br, 1H), 9.63 (s, 1H), 9.29 (s, 1H), 8.58 (d, 1H), 8.52 (d, 1H), 8.17 (s, 2H), 8.07 (m, 2H), 7.59 (m, 1H), 6.52 (br, 1H), 5.72 (m, 1H), 1.51 (d, 3H). MS m/z: 426.3 [M–H]—.

1-(6-Bromo-4-methylquinolin-3-yl)-3-(5-chloro-6-(2H-1,2,3-triazol-2-yl)pyridin-3-yl)urea (25)

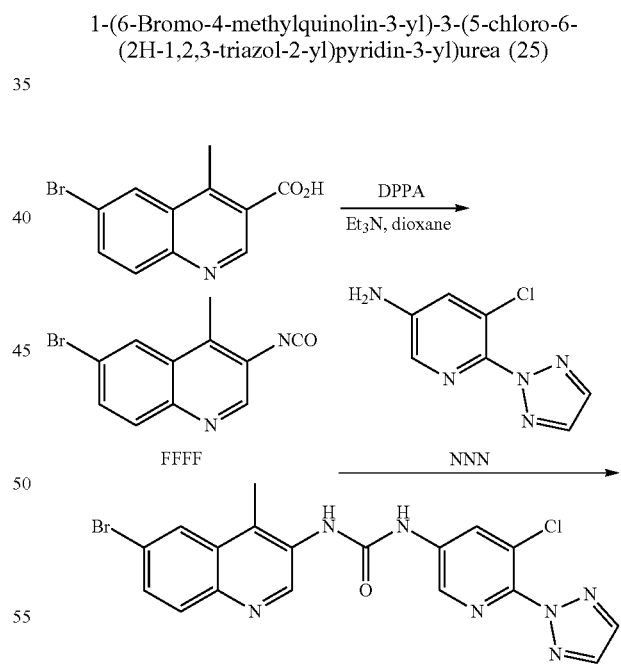

6-Bromo-3-isocyanato-4-methylquinoline (FFFF)

Diphenylphosphoryl azide (300 mg, 1.1 mmol) was added to a solution of 6-bromo-4-methylquinoline-3-carboxylic acid (290 mg, 1.1 mmol) and triethylamine (330 mg, 3.3 mmol) in dioxane (10 mL). The mixture was stirred at room temperature for 1 hour and then heated at 80° C. for 2 hours to give the isocyanate (FFFF), which was used directly in the next step.

1-(6-Bromo-4-methylquinolin-3-yl)-3-(5-chloro-6-(2H-1,2,3-triazol-2-yl)pyridin-3-yl)urea (25)

5-Chloro-6-(triazol-2-yl)pyridin-3-amine (NNN) (212 mg, 1.1 mmol) was added to a freshly prepared dioxane solution of 6-bromo-3-isocyanato-4-methylquinoline (1.1 mmol, 1 eq). The solution was stirred at room temperature for 30 min, and then heated at 100° C. for 10 hours. After cooling, the mixture was diluted with water (50 mL) and extracted with EtOAc (3×30 mL). The combined organic phases were washed with saturated NaHCO₃ solution (3×50 mL) and brine. After concentration, the residue was purified by prep-HPLC to give the title compound (45 mg, 9% yield). ¹H NMR (400 MHz, DMSO-d₆): 9.79 (s, 1H), 9.09 (s, 1H), 8.94 (s, 1H), 8.59 (d, 1H), 8.50 (d, 1H), 8.33 (d, 1H), 8.16 (s, 2H) 7.95 (d, 1H), 7.84 (m, 1H), 2.58 (s, 3H). MS m/z 460.5 [M+H]⁺.

Compounds 26-30 were prepared in an analogous manner, employing the indicated amine starting materials below.

| Example | Structure/Name | ¹H NMR (400 MHz, DMSO-d₆) | m/z [M + 1]⁺ | Starting materials |
|---|---|---|---|---|
| 26 | 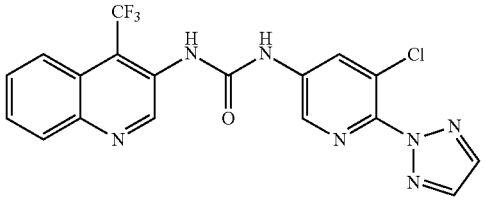 [SMILES: O=C(Nc1cnc(-n2nccn2)c(Cl)c1)Nc1cnc2ccccc2c1C(F)(F)F]<br>1-(5-Chloro-6-(2H-1,2,3-triazol-2-yl)pyridin-3-yl)-3-(4-(trifluoromethyl)quinolin-3-yl)urea | 10.05 (s, 1H), 9.29 (s, 1H), 9.12 (s, 1H), 8.60 (d, 1H), 8.48 (d, 1H), 8.18 (m, 3H), 8.12 (d, 1H), 7.85 (m, 2H) | 434.4 | (II) + (NNN) |
| 27 | 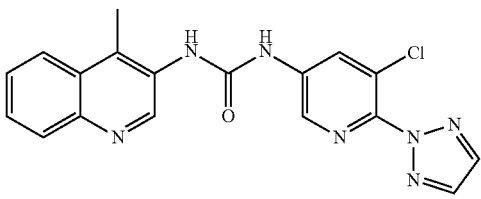 [SMILES: Cc1c(NC(=O)Nc2cnc(-n3nccn3)c(Cl)c2)cnc2ccccc12]<br>1-(5-Chloro-6-(2H-1,2,3-triazol-2-yl)pyridin-3-yl)-3-(4-methylquinolin-3-yl)urea | 9.92 (s, 1H), 9.100(s, 1H), 9.03 (s, 1H), 8.59 (d, 1H), 8.50 (d, 1H), 8.19 (m, 1H), 8.16 (s, 2H), 8.05 (d, 1H), 7.78 (m, 1H), 7.70 (m, 1H) | 380.32 | (KK) + (NNN) |
| 28 | 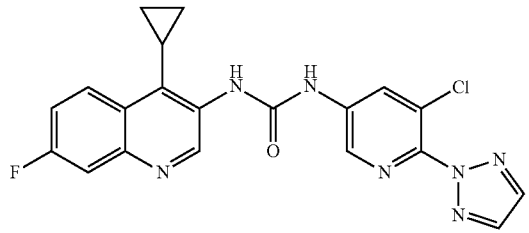 [SMILES: O=C(Nc1cnc(-n2nccn2)c(Cl)c1)Nc1cnc2cc(F)ccc2c1C1CC1]<br>1-(5-Chloro-6-(2H-1,2,3-triazol-2-yl)pyridin-3-yl)-3-(4-cyclopropyl-7-fluoroquinolin-3-yl)urea | 10.07 (s, 1H), 9.16 (s, 1H), 8.88 (s, 1H), 8.58 (d, 1H), 8.51 (m, 2H), 8.17 (s, 2H), 7.76 (m, 1H), 7.60 (m, 1H), 2.05 (m, 2H), 1.30 (m, 2H), 0.65 (m, 2H) | 424.0 | (OO) + (NNN) |
| 29 | 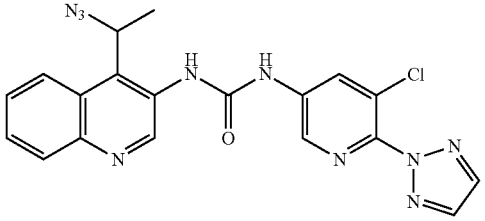 [SMILES: CC(N=[N+]=[N-])c1c(NC(=O)Nc2cnc(-n3nccn3)c(Cl)c2)cnc2ccccc12]<br>1-(4-(1-Azidoethyl)quinolin-3-yl)-3-(5-chloro-6-(2H-1,2,3-triazol-2-yl)pyridin-3-yl)urea | 10.01 (s, 1H), 8.99 (s, 1H), 8.94 (s, 1H), 8.59 (d, 1H), 8.49 (d, 1H), 8.43 (d, 1H), 8.16 (s, 2H), 8.08 (d, 1H), 7.78 (m, 1H), 7.68 (m, 1H), 5.87 (q, 1H), 1.65 (d, 3H) | [M − 1]⁻ 433.2 | (YY) + (NNN) |

-continued

| Example | Structure/Name | $^1$H NMR (400 MHz, DMSO-$d_6$) | m/z [M + 1]$^+$ | Starting materials |
|---|---|---|---|---|
| 30 | 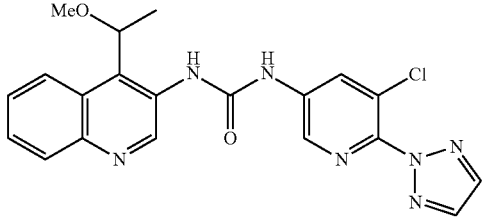 [SMILES: COC(C)c1c(NC(=O)Nc2cnc(-n3nccn3)c(Cl)c2)cnc2ccccc12]  1-(5-Chloro-6-(2H-1,2,3-triazol-2-yl)pyridin-3-yl)-3-(4-(1-methoxyethyl)quinolin-3-yl)urea | 10.33 (s, 1H), 9.25 (s, 1H), 9.02 (s, 1H), 8.57 (s, 1H), 8.52 (s, 1H), 8.40 (m, 1H), 8.15 (s, 2H), 8.03 (m, 1H), 7.73 (m, 1H), 7.64 (m, 1H), 5.43 (m, 1H), 3.26 (s, 3H), 1.59 (d, 3H) | 424.0 | (WW) + (NNN) |

1-(4-Bromoquinolin-3-yl)-3-(5-chloro-6-(2H-1,2,3-triazol-2-yl)pyridin-3-yl)urea (31)

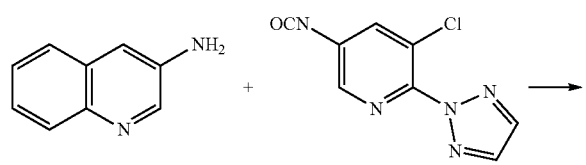

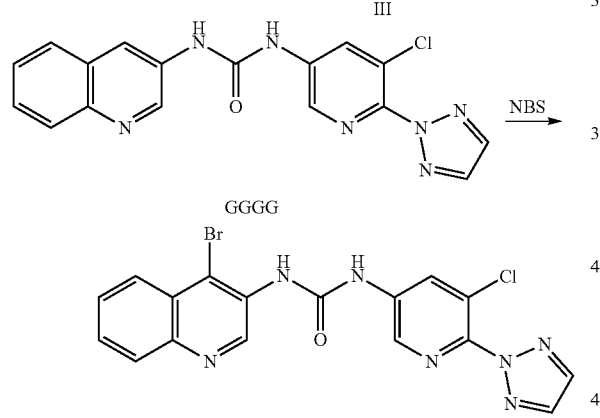

1-(5-Chloro-6-(2H-1,2,3-triazol-2-yl)pyridin-3-yl)-3-(quinolin-3-yl)urea (GGGG)

(5-Chloro-6-(2H-1,2,3-triazol-2-yl)pyridin-3-yl)-3-(quinolin-3-yl)urea (GGGG) was prepared with a method analogous to that used in preparing Compound 1, from quinolin-3-amine and 3-chloro-5-isocyanato-2-(2H-1,2,3-triazol-2-yl)pyridine (I). $^1$H NMR (400 MHz, DMSO-$d_6$): δ 9.70 (bs, 1H), 9.60 (s, 1H), 8.92 (s, 1H), 8.60 (s, 1H), 8.57 (m, 1H), 8.50 (m, 1H), 8.17 (s, 2H), 7.96 (m, 2H), 7.61 (m, 2H).

1-(4-Bromoquinolin-3-yl)-3-(5-chloro-6-(2H-1,2,3-triazol-2-yl)pyridin-3-yl)urea (31)

NBS (143 mg, 0.8 mmol) was added to a solution of (5-Chloro-6-(2H-1,2,3-triazol-2-yl)pyridin-3-yl)-3-(quinolin-3-yl)urea (245 mg, 0.67 mmol) in DMF (15 mL) at room temperature, the resulting mixture was stirred at 50° C. for 3 hours. After cooling, the mixture was diluted with EtOAc (100 mL), washed with saturated NaHCO$_3$ solution (3×50 mL) and brine, and concentrated. The residue was purified by prep-HPLC to give the title compound (60 mg, 20% yield). $^1$H NMR (400 MHz, DMSO-$d_6$): δ 10.20 (s, 1H), 9.34 (s, 1H), 8.98 (s, 1H), 8.58 (d, J=2.4 Hz, 1H), 8.52 (d, J=2.4 Hz, 1H), 8.16 (m, 2H), 8.09 (m, 1H), 7.79 (m, 2H). MS m/z 445.78 [M+H]$^+$.

1-(5-Chloro-6-(2H-1,2,3-triazol-2-yl)pyridin-3-yl)-3-(4-(1-hydroxyethyl)quinolin-3-yl)urea (32)

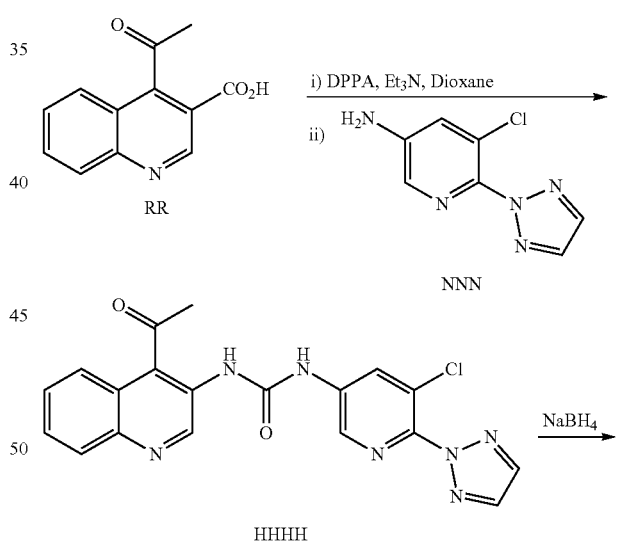

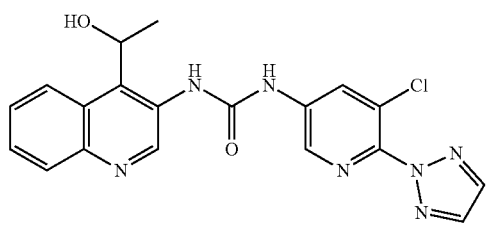

1-(4-Acetylquinolin-3-yl)-3-(5-chloro-6-(2H-1,2,3-triazol-2-yl)pyridin-3-yl)urea (HHHH)

1-(4-Acetylquinolin-3-yl)-3-(5-chloro-6-(2H-1,2,3-triazol-2-yl)pyridin-3-yl)urea (HHHH) was prepared with a method analogous to that used in preparing Compound 25, from 4-acetylquinoline-3-carboxylic acid (RR) and 5-chloro-6-(triazol-2-yl)pyridin-3-amine (NNN). $^1$H NMR (400 MHz, DMSO-$d_6$): δ 9.70 (bs, 1H), 9.60 (s, 1H), 8.92 (s, 1H), 8.60 (s, 1H), 8.57 (m, 1H), 8.50 (m, 1H), 8.17 (s, 2H), 7.96 (m, 2H), 7.61 (m, 2H).

1-(5-Chloro-6-(2H-1,2,3-triazol-2-yl)pyridin-3-yl)-3-(4-(1-hydroxyethyl)quinolin-3-yl)urea (32)

Sodium borohydride (9.3 mg, 0.24 mmol) was added to a solution of 1-(4-acetylquinolin-3-yl)-3-(5-chloro-6-(2H-1,2,3-triazol-2-yl)pyridin-3-yl)urea (HHHH; 50 mg, 0.12 mmol) in anhydrous methanol (10 mL) at −10° C. The reaction mixture was allowed to warm to room temperature with stirring overnight. The resulting mixture was diluted with water and extracted (EtOAc). The combined organic layers were washed with saturated NaHCO$_3$ solution and brine, concentrated and the residue was purified by HPLC to give the title compound (21 mg). $^1$H NMR (400 MHz, DMSO-$d_6$): δ 10.56 (s, 1H), 9.67 (s, 1H), 9.36 (s, 1H), 8.59 (d, 1H), 8.52 (d, 1H), 8.35 (d, 1H), 8.16 (s, 2H), 8.02 (d, 1H), 7.74 (m, 1H), 7.66 (m, 1H), 5.86 (m, 1H), 1.54 (d, 1H). MS m/z 410.2 [M+H]$^+$.

1-(7-Cyclopropyl-2-methylthiazolo[5,4-b]pyridin-6-yl)-3-(2-(trifluoromethyl)pyridin-4-yl)urea (33)

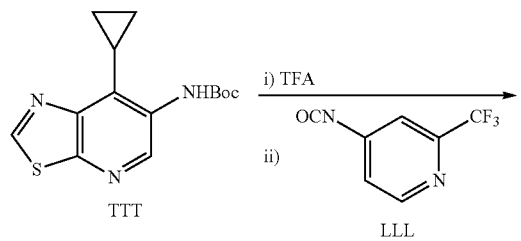

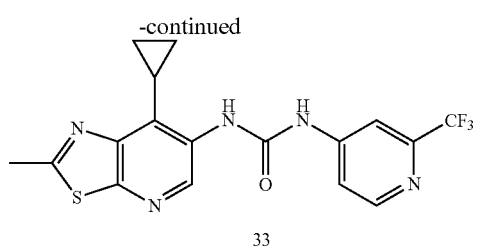

33

1-(7-Cyclopropyl-2-methylthiazolo[5,4-b]pyridin-6-yl)-3-(2-(trifluoromethyl)pyridin-4-yl)urea (33)

tert-Butyl (7-cyclopropyl-2-methylthiazolo[5,4-b]pyridin-6-yl)carbamate (TTT) (35 mg, 0.12 mmol) was dissolved in DCM (10 mL). TFA (1 mL) was added and the mixture stirred for 1 hour. The solvent was removed and the residue dissolved in 1,4-dioxane (2 mL). This solution was added to a solution of 2-(trifluoromethyl)isonicotinic acid (LLL; 20 mg, 0.10 mmol) in 1,4-dioxane (2 mL) that had been stirring for 30 minutes at room temperature with DPPA (27 μL, 0.13 mmol) and Et$_3$N (72 μL, 0.52 mmol). The mixture was stirred at 100° C. for 1 hour, quenched with sat. aq. NaHCO$_3$ solution and extracted with EtOAc (3×50 mL). The combined organic layer was washed with brine, dried over MgSO$_4$ and concentrated. The residue was purified by reversed-phase HPLC (1 to 70% ACN in H$_2$O) to give the title compound (15 mg, 33% yield). $^1$H NMR (500 MHz, DMSO-$d_6$): δ 9.93 (s, 1H), 8.77 (s, 1H), 8.57 (s, 1H), 8.54 (d, 1H), 8.07 (s, 1H), 7.63 (m, 1H), 2.80 (s, 3H), 2.19 (m, 1H), 1.55 (m, 2H), 1.78 (m, 2H); MS m/z: 394.25 [M+H]$^+$.

Compound 34 was prepared in an analogous manner, employing the indicated amine starting materials below.

| Example | Structure/Name | $^1$H NMR (500 MHz, DMSO-$d_6$) | m/z [M + 1]$^+$ | Starting materials |
|---|---|---|---|---|
| 34 | 1-(5-Chloro-6-(2H-1,2,3-triazol-2-yl)pyridin-3-yl)-3-(7-cyclopropyl-2-methylthiazolo[5,4-b]pyridin-6-yl)urea | δ 9.82 (s, 1H), 8.79 (s, 1H), 8.60 (s, 1H), 8.57 (d, 1H), 8.48 (d, 1H), 8.15 (s, 2H), 2.81 (s, 3H), 2.22 (m, 1H), 1.57 (m, 2H), 1.16 (m, 2H) | 427.17 | (TTT) + (III) |

1-(5-Chloro-6-(2H-1,2,3-triazol-2-yl)pyridin-3-yl)-3-(7-(1-ethoxyethyl)-2-methylthiazolo[5,4-b]pyridin-6-yl)urea (35)

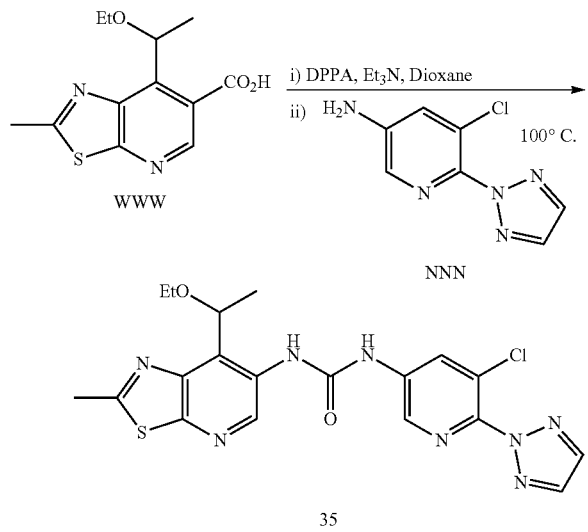

Et₃N (261 µL, 1.88 mmol) and DPPA (97 µL, 0.45 mmol) were added to a stirred solution of 7-(1-ethoxyethyl)-2-methylthiazolo[5,4-b]pyridine-6-carboxylic acid (100 mg, 0.38 mmol) in 1,4-dioxane (3 mL) and the reaction stirred for 30 minutes at rt. 5-Chloro-6-(2H-1,2,3-triazol-2-yl)pyridin-3-amine (NNN, 146 mg, 0.75 mmol) was added and the mixture heated to 100° C. for 1 hour, quenched with sat. aqueous NaHCO₃ solution and extracted with EtOAc (3×50 mL). The combined organic layer was washed with brine, dried over MgSO₄, concentrated and purified by reversed-phase chromatography using a gradient of 1 to 70% ACN in H₂O to give the title compound (51 mg, 30% yield) as a white solid. ¹H NMR (500 MHz, DMSO-d₆): δ 10.51 (s, 1H), 9.12 (s, 1H), 8.70 (s, 1H), 8.57 (d, 1H), 8.51 (d, 1H), 8.16 (s, 2H), 5.62 (q, 1H), 3.50 (q, 2H), 2.85 (s, 3H), 1.57 (d, 3H), 1.18 (t, 3H); MS m/z: 459.16 [M+H]⁺.

Compounds 36-41 were prepared in an analogous manner, employing the starting materials indicated below.

| Example | Structure/Name | ¹H NMR (500 MHz, DMSO-d₆) | m/z [M + 1]⁺ | Starting materials |
|---|---|---|---|---|
| 36 | 1-(5-Chloro-6-(2H-1,2,3-triazol-2-yl)pyridin-3-yl)-3-(7-cyclopropylthiazolo[5,4-b]pyridin-6-yl)urea | 9.82 (s, 1H), 9.46 (s, 1H), 8.83 (s, 1H), 8.71 (s, 1H), 8.58 (d, 1H), 8.48 (d, 1H), 8.15 (s, 2H), 2.27 (m, 1H), 1.62 (m, 2H), 1.19 (m, 2H) | 413.07 | (XXX) + (NNN) |
| 37 | 1-(5-Chloro-6-(2H-1,2,3-triazol-2-yl)pyridin-3-yl)-3-(7-(1-ethoxyethyl)thiazolo[5,4-b]pyridin-6-yl)urea | 10.53 (s, 1H), 9.55 (s, 1H), 9.22 (s, 1H), 8.74 (s, 1H), 8.57 (d, 1H), 8.51 (d, 1H), 8.16 (s, 2H), 5.68 (q, 1H), 3.52 (q, 2H), 1.59 (d, 3H), 1.18 (t, 3H) | 445.17 | (YYY) + (NNN) |

| Example | Structure/Name | ¹H NMR (500 MHz, DMSO-d₆) | m/z [M + 1]⁺ | Starting materials |
|---|---|---|---|---|
| 38 | 1-(5-Chloro-6-(2H-1,2,3-triazol-2-yl)pyridin-3-yl)-3-(7-(dimethylamino)thiazolo[5,4-b]pyridin-6-yl)urea | 9.96 (s, 1H), 9.37 (s, 1H), 8.78 (s, 1H), 8.67 (s, 1H), 8.56 (d, 1H), 8.49 (d, 1H), 8.16 (s, 2H), 3.18 (s, 6H) | 416.11 | (AAAA) + (NNN) |
| 39 | 1-(5-Chloro-6-(2H-1,2,3-triazol-2-yl)pyridin-3-yl)-3-(7-((2-methoxyethyl)(methyl)amino)thiazolo[5,4-b]pyridin-6-yl)urea | δ 10.06 (s, 1H), 9.41 (s, 1H), 8.91 (s, 1H), 8.62 (s, 1H), 8.56 (d, 1H), 8.51 (d, 1H), 8.15 (s, 2H), 3.68 (t, 2H), 3.49 (t, 2H), 3.16 (s, 3H), 3.14 (s, 3H) | 460.12 | (BBBB) + (NNN) |
| 40 | 1-(5-Chloro-6-(2H-1,2,3-triazol-2-yl)pyridin-3-yl)-3-(7-((1-methoxypropan-2-yl)(methyl)amino)thiazolol[5,4-b]pyridin-6-yl)urea | 10.26 (s, 1H), 9.40 (s, 1H), 8.81 (s, 1H), 8.59 (d, 1H), 8.56 (s, 1H), 8.49 (d, 1H), 8.15 (s 2H) 4.08 (m, 1H), 3.62 (m, 1H), 3.37 (m, 1H), 3.21 (s, 3H), 3.06 (s, 3H), 1.23 (d, 3H) | 474.11 | (CCCC) + (NNN) |
| 41 | 1-(7-(Azetidin-1-yl)thiazolo[5,4-b]pyridin-6-yl)-3-(5-chloro-6-(2H-1,2,3-triazol-2-yl)pyridin-3-yl)urea | 9.82 (hr s, 1H), 9.19 (s, 1H), 8.59 (d, 1H), 8.46 (d, 1H), 8.44 (s, 1H), 8.15 (m, 3H), 4.68 (m, 4H), 2.39 (m, 2H) | 428.07 | (DDDD) + (NNN) |

MALT1 Inhibition Assay

Table 1 provides the results of cell assay data showing MALT1 inhibition data ($IC_{50}$) and cell proliferation inhibition data ($GI_{50}$) for the example compounds. MALT1 inhibition was demonstrated by use of a MALT1 inhibition reporter system, and the cell proliferation inhibition was demonstrated by use of an OCI-LY3 lymphoma cell line. The results show that the compounds of the present disclosure are potent MALT1 inhibitors in cells, and the inhibition of MALT1 results in significant growth inhibition of cancer cells.

TABLE 1

| Example | MALT1 $IC_{50}$ (µM) | OCI-LY3 $GI_{50}$ 96 h (µM) |
|---|---|---|
| 1 | 0.057 | 1.13 |
| 2 | 0.076 | 2.19 |
| 3 | 0.448 | 8.94 |
| 4 | 0.007 | 1.58 |
| 5 | 0.078 | 2.41 |
| 6 | 0.451 | — |
| 7 | 0.432 | — |
| 8 | 0.002 | 1.16 |
| 9 | 0.006 | 0.72 |
| 10 | >20.0 | — |
| 11 | 0.013 | 1.58 |
| 12 | 0.330 | 4.41 |
| 13 | 8.670 | — |
| 14 | 0.093 | 1.49 |
| 15 | 0.141 | 8.3 |
| 16 | 0.179 | 10.4 |
| 17 | 2.660 | — |
| 18 | 0.035 | 0.41 |
| 19 | 0.130 | 0.7 |
| 20 | 0.018 | 0.27 |
| 21 | 0.045 | 3.49 |
| 22 | 0.023 | 0.62 |
| 23 | 0.053 | 1.62 |
| 24 | 0.007 | 0.56 |
| 25 | 0.158 | — |
| 26 | 0.041 | — |
| 27 | 0.237 | — |
| 28 | 0.092 | — |
| 29 | 0.045 | 1.23 |
| 30 | 0.033 | 0.62 |
| 31 | 0.033 | 2.28 |
| 32 | 0.028 | 0.72 |
| 33 | 0.243 | — |
| 34 | 0.046 | 1.38 |
| 35 | 0.036 | 0.37 |
| 36 | 0.033 | 1.01 |
| 37 | 0.024 | 0.79 |
| 38 | 0.040 | 1.16 |
| 39 | 0.098 | 1.78 |
| 40 | 0.473 | 9.18 |
| 41 | 0.927 | 8.69 |

In Cell MALT1 Inhibition Reporter System for High Throughput Screening (HTS) Method for MALT1 Protease Inhibitors The reporter system utilized split luciferase technology (Promega GloSensor™) where a firefly luciferase enzyme is separated into two components by a cAMP-binding protein moiety. Binding of cAMP induces a conformational change that triggers light output. A MALT1 cleavage signal based on the RelB cleavage site was engineered so that the conformational change required for cAMP binding occurred only after MALT1 mediated cleavage. To control for luciferase activity interference independent of MALT1 cleavage, Renilla luciferase was used. A stable Raji reporter cell line where B-cell receptor signaling is activated with 12-phorbol 13-myristate acetate (PMA) and ionomycin to trigger MALT1 protease activity was generated. Raji MALT1-reporter cells were pre-treated for 30 min with inhibitors and then with PMA/ionomycin for 1 h and $IC_{50}$ was used to rank compounds.

The assay was performed in 384-well plates. 5 µL of 10×3-fold serial compound dilutions prepared in cell culture media was added to the plate using liquid handling robotics (Microlab STAR, Hamilton). Compound start concentration was 2 µM and final vehicle concentration was 0.2% DMSO in all wells unless otherwise noted. Raji GloSensor cells were resuspended in complete media at $1.33*10^6$/ml and 2% GloSensor Reagent was added to cell suspension. 45 µl of cell mix was then added to the plate and incubated for 30 minutes at 37° C. and 5% $CO_2$. Next, 2 µL per well of a 26×PMA/IO solution (final concentration PMA=0.2 µg/mL, IO=1 µM) was added to the plate using liquid handling robotics (MultifloFX, Biotek). The plate was incubated for an additional 1 hour and 45 minutes at 37° C. and 5% $CO_2$, and the luminescence output was read.

Cell Proliferation Inhibition Assay

Compounds were plated in 5 µL, then 2,000 cells/well were plated in 45 µL in 384-well white/clear plates (BD 353963). Cells were grown at 37° C. for 96 hours.

1. Cells were counted to confirm a sufficient number were present in the assay. Cells were centrifuged (300×g 5 min) and resuspended at 4.44×10∝cells/mL with fresh media.
2. Dilutions of compounds were prepared: working dilutions were 10× the highest concentration tested and were prepared in a 96-well V-bottom plate for serial dilution. All compounds tested in each assay had the same concentration of DMSO, as well as all the serial dilutions.
3. Compounds were plated in triplicate: 5 µL/well. (Included 12 wells of control for standard curve (3 blank, 9 standard- and three wells of z-VRPR-fnk at 50 µM as positive control).
4. Cells were plated at a concentration of 45 µL/well. For blank, three control wells were utilized (5 µL vehicle) with an added 45 µL of media, instead of cells.
5. The plates were briefly spun down to ensure there were no bubbles. The plates were then incubated at 37° C. for 48 hours, then steps 2-5 were repeated.
6. Logarithmic growth of control cells was assessed by Trypan blue counting of vehicle-treated cells.
7. 50 µL of CTGlo (Promega) was added, followed by rocking for 2 min, then incubated 10 min at RT. Luminescence was measured.

Data Processing:

Cell count was evaluated as a measure of how well cells performed in the assay. The blank was substracted from all measurements, and growth inhibition was calculated relative to vehicle treated cells (0% inhibition) and no cells (100% inhibition) wells. The average, standard deviation and coefficient of variation was calculated for each triplicate. The coefficient of variation was less than 12%. Three independent experiments were averaged, and the growth inhibition values and concentration were used to construct dose-response curves in CDD (Collaborative Dug Discovery vault) and calculate $GI_{50}$.

Equivalents and Scope

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:
1. A compound of Formula I:

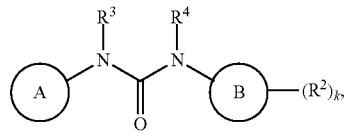

or a pharmaceutically acceptable salt thereof, wherein:
A is

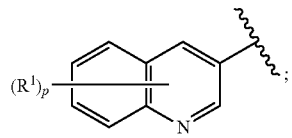

B is

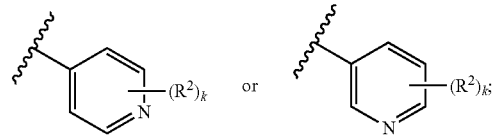

each occurrence of $R^1$ is, independently, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted heteroaryl, substituted or unsubstituted heteroalkyl, $OR^A$, $N(R^A)_2$, $-SR^A$, $-CN$, $-SCN$, $-C(=NR^A)R^A$, $-C(=NR^A)OR^A$, $-C(=NR^A)N(R^A)_2$, $-C(=O)R^A$, $-C(=O)OR^A$, $-C(=O)N(R^A)_2$, $-S(=O)R^A$, $-S(=O)_2R^A$, $-NO_2$, $-NR^AC(=O)R^A$, $-NR^AC(=O)OR^A$, $-NR^AC(=O)N(R^A)_2$, $-NR^AS(=O)R^A$, $-NR^AS(=O)_2R^A$, $-S(=O)N(R^A)_2$, $-S(=O)_2N(R^A)_2$, $-OC(=O)R^A$, $-OC(=O)OR^A$, or $-OC(=O)N(R^A)_2$;

each occurrence of $R^2$ is, independently, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted heteroalkyl, $-OR^A$, $-N(R^A)_2$, $-SR^A$, $-CN$, $-SCN$, $-C(=NR^A)R^A$, $-C(=NR^A)OR^A$, $-C(=NR^A)N(R^A)_2$, $-C(=O)R^A$, $-C(=O)OR^A$, $-C(=O)N(R^A)_2$, $-S(=O)R^A$, $-S(=O)_2R^A$, $-NO_2$, $-NR^AC(=O)R^A$, $-NR^AC(=O)OR^A$, $-NR^AC(=O)N(R^A)_2$, $-NR^AS(=O)R^A$, $-NR^AS(=O)_2R^A$, $-S(=O)N(R^A)_2$, $-S(=O)_2N(R^A)_2$, $-OC(=O)R^A$, $-OC(=O)OR^A$, or $-OC(=O)N(R^A)_2$;

each occurrence of $R^3$ and $R^4$ is, independently, hydrogen, substituted or unsubstituted alkyl, or a nitrogen protecting group;

each occurrence of $R^A$ is, independently, hydrogen, substituted or unsubstituted acyl, substituted or unsubstituted alkyl, substituted or unsubstituted alkenyl, substituted or unsubstituted alkynyl, substituted or unsubstituted heteroalkyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^A$ groups are joined to form a substituted or unsubstituted heterocyclic ring;

k is 1, 2, 3, or 4; and p is 1, 2, 3, or 4.

2. The compound of claim 1, or a pharmaceutically acceptable salt thereof, wherein:

A is

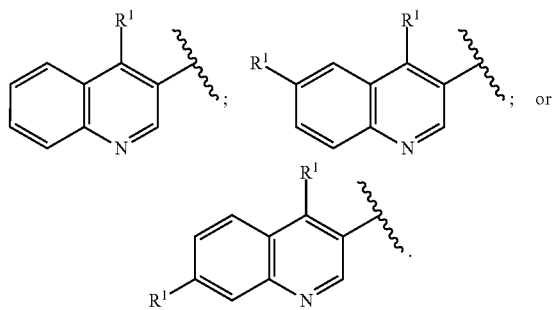

3. The compound of claim 1, or a pharmaceutically acceptable salt thereof, wherein:

B is

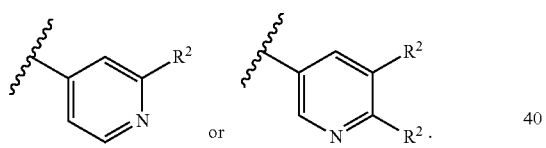

4. The compound of claim 1, or a pharmaceutically acceptable salt thereof, wherein each occurrence of $R^1$ is, independently, halogen, substituted or unsubstituted alkyl, substituted or unsubstituted alkenyl, substituted or unsubstituted alkynyl, substituted or unsubstituted heterocyclyl, substituted or unsubstituted carbocyclyl, substituted or unsubstituted heteroaryl, substituted or unsubstituted heteroalkyl, or —$OR^A$.

5. The compound of claim 1, or a pharmaceutically acceptable salt thereof, wherein each occurrence of $R^1$ is, independently, halogen, substituted or unsubstituted alkyl, substituted or unsubstituted carbocyclyl, substituted or unsubstituted heteroaryl, substituted or unsubstituted heteroalkyl, or —$OR^A$.

6. The compound of claim 1, or a pharmaceutically acceptable salt thereof, wherein each occurrence of $R^1$ is, independently, halogen, unsubstituted $C_{1-6}$ alkyl, $C_{1-6}$ alkoxyalkyl, $C_{1-6}$ hydroxyalkyl, $C_{1-6}$ azidoalkyl, $C_{1-6}$ haloalkyl, unsubstituted 5 or 6-membered monocyclic heteroaryl, unsubstituted $C_{3-6}$ cycloalkyl, or —$OC_{1-6}$ alkyl.

7. The compound of claim 1, or a pharmaceutically acceptable salt thereof, wherein each occurrence of $R^2$ is, independently, halogen, substituted or unsubstituted alkyl, substituted or unsubstituted alkenyl, substituted or unsubstituted alkynyl, substituted or unsubstituted heterocyclyl, substituted or unsubstituted carbocyclyl, substituted or unsubstituted aryl, substituted or unsubstituted heteroaryl, substituted or unsubstituted heteroalkyl, or —$OR^A$.

8. The compound of claim 1, or a pharmaceutically acceptable salt thereof, wherein each occurrence of $R^2$ is, independently, halogen, substituted or unsubstituted alkyl, or substituted or unsubstituted heteroaryl.

9. The compound of claim 1, or a pharmaceutically acceptable salt thereof, wherein $R^3$ is hydrogen; and $R^4$ is hydrogen.

10. The compound of claim 1, or a pharmaceutically acceptable salt thereof, wherein k is 1 or 2.

11. The compound of claim 1, or a pharmaceutically acceptable salt thereof, wherein p is 1 or 2.

12. The compound of claim 1, wherein the compound is of Formula I-c or I-d:

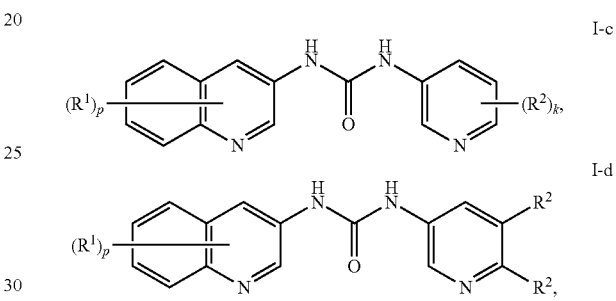

or a pharmaceutically acceptable salt thereof.

13. The compound of claim 1, wherein the compound is of Formula I-e or I-f:

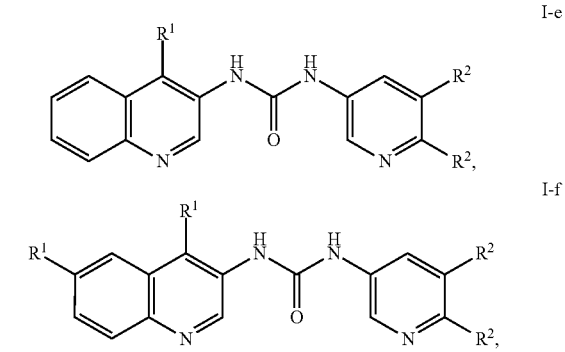

or a pharmaceutically acceptable salt thereof.

14. The compound of claim 1, wherein the compound is of Formula I-g or I-h:

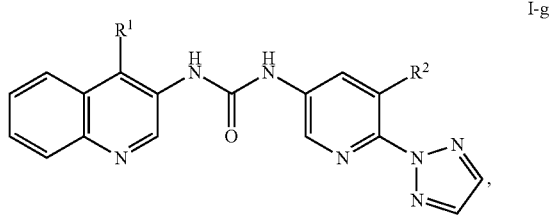

I-h
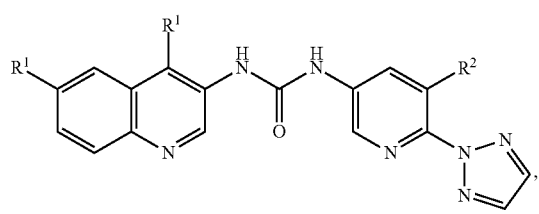
or a pharmaceutically acceptable salt thereof.
15. The compound of claim 1, wherein the compound is
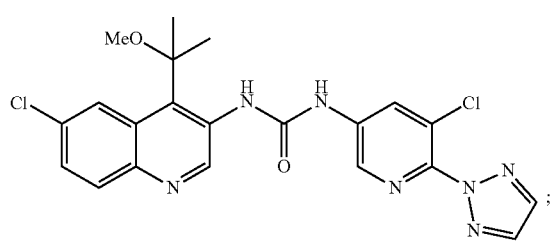
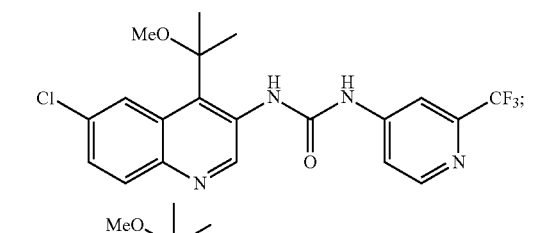
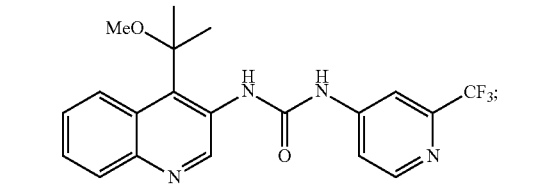
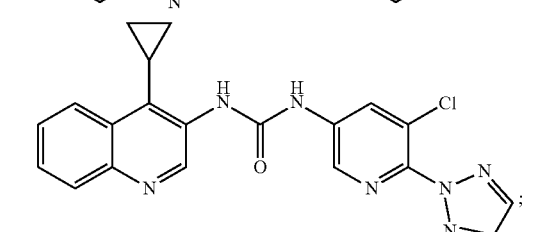
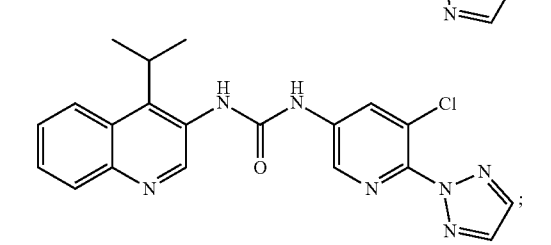
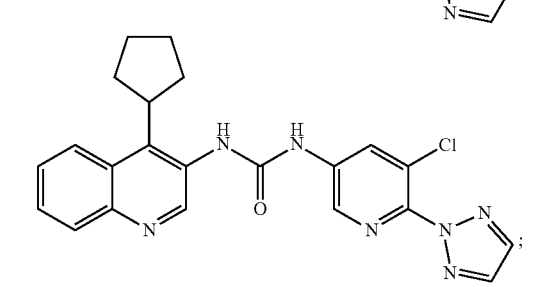
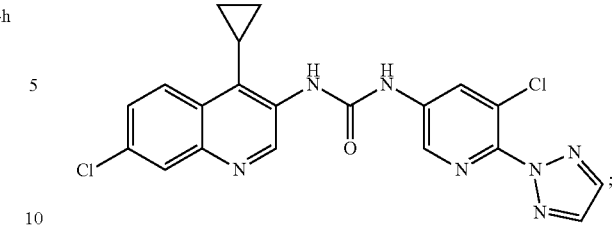
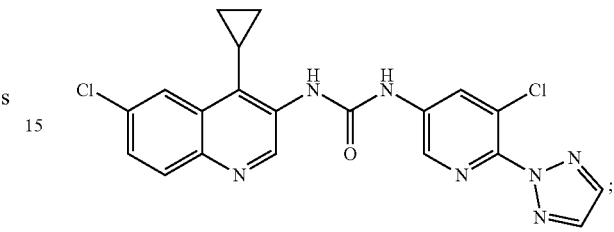
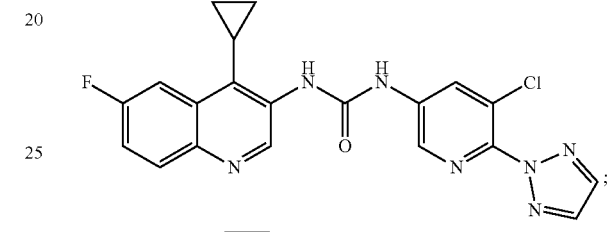
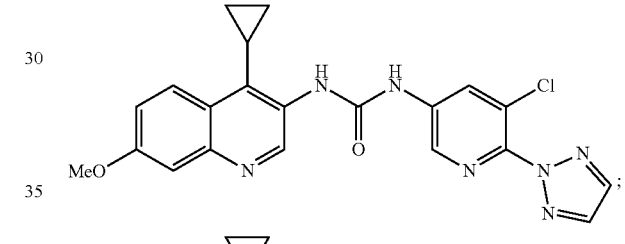
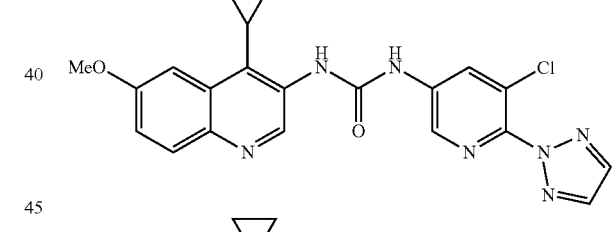
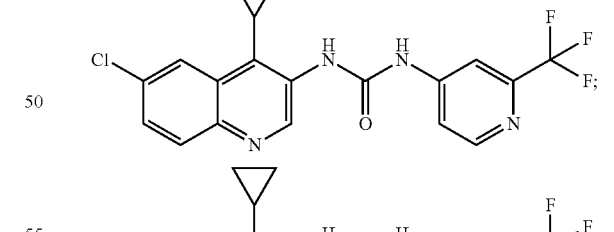
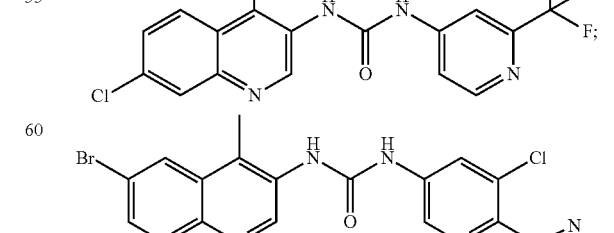

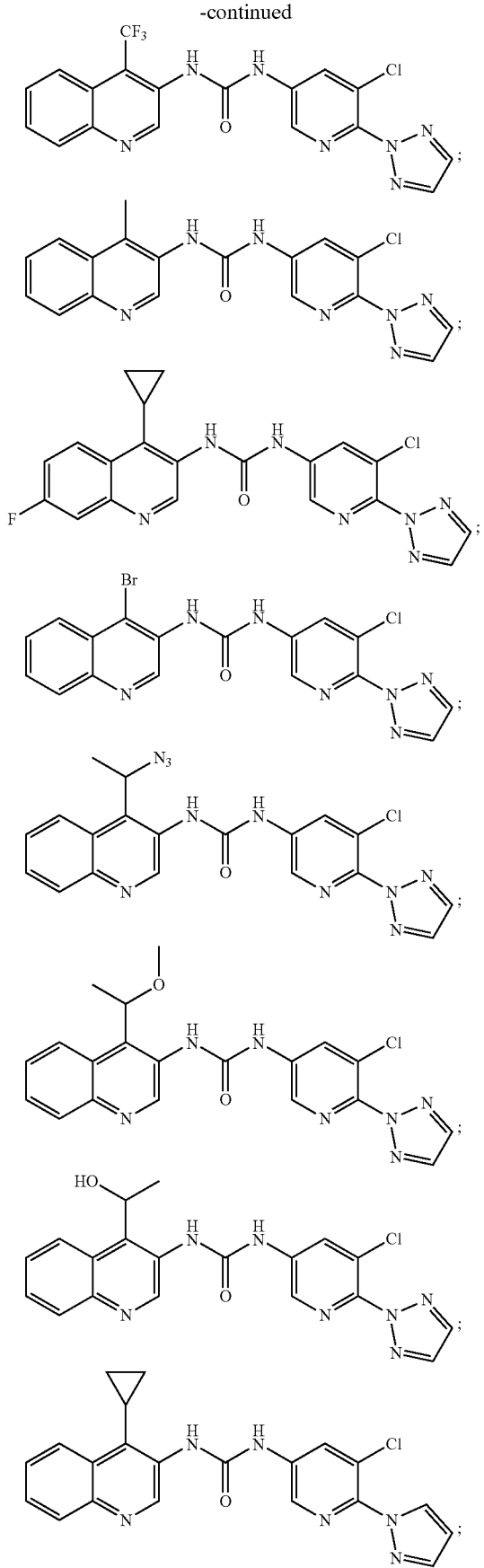
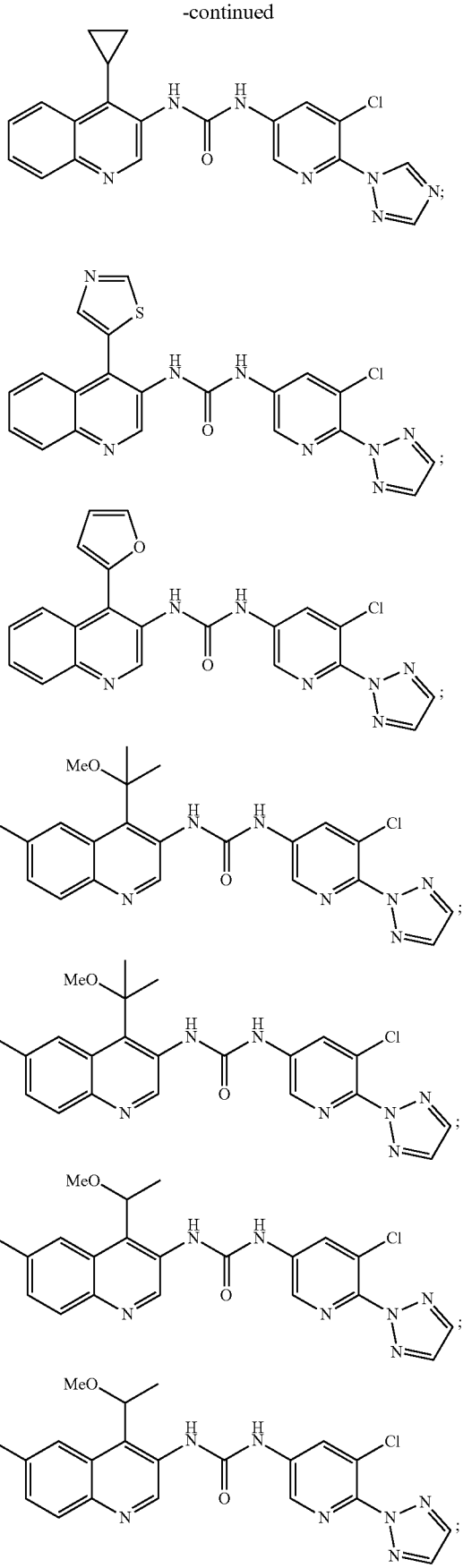

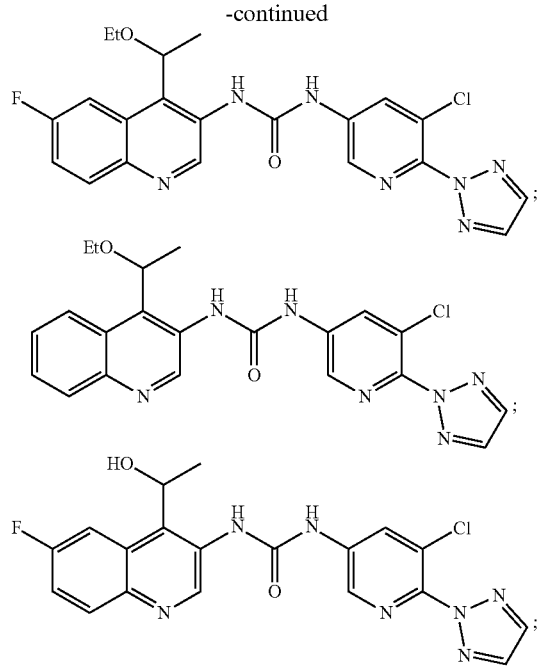

or a pharmaceutically acceptable salt thereof.
16. A compound of the formula:

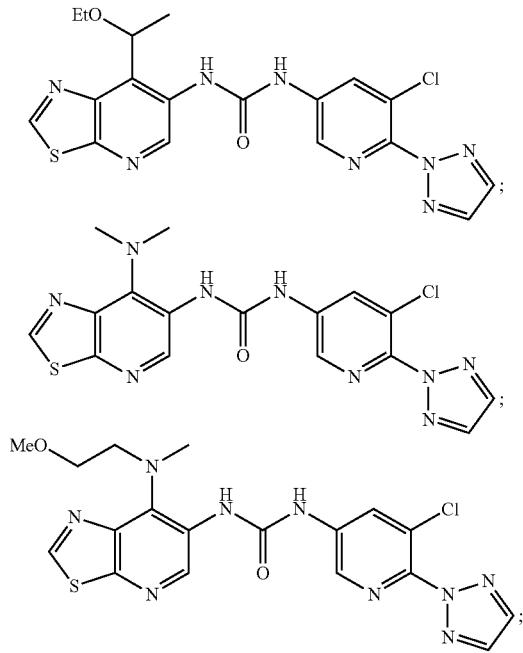

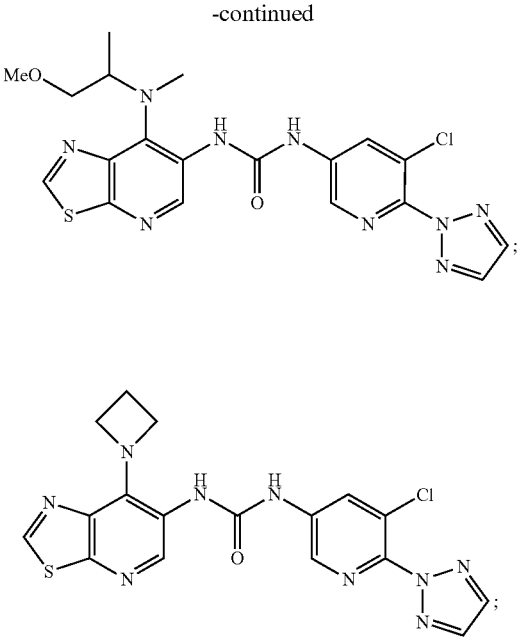

or a pharmaceutically acceptable salt thereof.

17. A pharmaceutical composition comprising a compound of claim 1, or a pharmaceutically acceptable salt thereof, and a pharmaceutically acceptable excipient.

18. A method of inhibiting the activity of MALT1, the method comprising contacting a compound of claim 1 with MALT1.

19. A method of treating a hematological cancer in a subject in need thereof, the method comprising administering a compound of claim 1, or a pharmaceutically acceptable salt thereof, to the subject.

20. The compound of claim 1, or a pharmaceutically acceptable salt thereof, wherein each occurrence of $R^2$ is, independently, halogen, $C_{1-6}$ haloalkyl, or unsubstituted 5-membered monocyclic heteroaryl.

* * * * *

UNITED STATES PATENT AND TRADEMARK OFFICE
CERTIFICATE OF CORRECTION

PATENT NO. : 11,248,007 B2  
APPLICATION NO. : 16/492066  
DATED : February 15, 2022  
INVENTOR(S) : Nathanael S. Gray et al.

Page 1 of 1

It is certified that error appears in the above-identified patent and that said Letters Patent is hereby corrected as shown below:

In the Claims

In Claim 1, at Column 150, Line 38, the text:
"$OR^A$, $N(R^A)_2$,"
Should be replaced with:
-- $-OR^A$, $-N(R^A)_2$, --.

In Claim 1, at Column 150, Line 59, the text:
"$-S(=O)_2 N(R^A)_2$,"
Should be replaced with:
-- $-S(=O)_2N(R^A)_2$, --.

Signed and Sealed this  
Twenty-fourth Day of September, 2024

Katherine Kelly Vidal  
*Director of the United States Patent and Trademark Office*